US010597710B2

(12) United States Patent
Lohman et al.

(10) Patent No.: US 10,597,710 B2
(45) Date of Patent: *Mar. 24, 2020

(54) LIGASE ACTIVITY

(71) Applicant: New England Biolabs, Inc., Ipswich, MA (US)

(72) Inventors: Gregory Lohman, Cambridge, MA (US); Thomas C. Evans, Jr., Topsfield, MA (US); Larry A. McReynolds, Beverly, MA (US)

(73) Assignee: New England Biolabs, Inc., Ipswich, MA (US)

( * ) Notice: Subject to any disclaimer, the term of this patent is extended or adjusted under 35 U.S.C. 154(b) by 628 days.

This patent is subject to a terminal disclaimer.

(21) Appl. No.: 14/839,433

(22) Filed: Aug. 28, 2015

(65) Prior Publication Data

US 2016/0002716 A1 Jan. 7, 2016

Related U.S. Application Data

(63) Continuation-in-part of application No. 13/829,489, filed on Mar. 14, 2013.

(60) Provisional application No. 62/192,623, filed on Jul. 15, 2015, provisional application No. 62/174,257, filed on Jun. 11, 2015, provisional application No. 62/045,214, filed on Sep. 3, 2014, provisional application No. 61/745,244, filed on Dec. 21, 2012.

(51) Int. Cl.
| *C12Q 1/68* | (2018.01) |
| *C12Q 1/6862* | (2018.01) |
| *C12Q 1/6853* | (2018.01) |
| *C12N 9/00* | (2006.01) |

(52) U.S. Cl.
CPC ............ *C12Q 1/6862* (2013.01); *C12N 9/93* (2013.01); *C12Q 1/6853* (2013.01); *C12Y 605/01003* (2013.01); *G01N 2333/9015* (2013.01)

(58) Field of Classification Search
None
See application file for complete search history.

(56) References Cited

U.S. PATENT DOCUMENTS

| 5,429,807 | A | 7/1995 | Matson et al. |
| 5,599,695 | A | 2/1997 | Pease et al. |
| 5,654,413 | A | 8/1997 | Brenner et al. |
| 5,871,928 | A | 6/1999 | Fodor et al. |
| 6,368,801 | B1 | 4/2002 | Faruqi |
| 7,361,488 | B2 | 4/2008 | Fan et al. |
| 7,888,015 | B2 | 2/2011 | Toumazou et al. |
| 2010/0184618 | A1* | 7/2010 | Namsaraev ......... C12Q 1/6837 506/9 |
| 2011/0092375 | A1 | 4/2011 | Zamore et al. |

FOREIGN PATENT DOCUMENTS

WO   WO0179420   8/1998

OTHER PUBLICATIONS

Lohman et al., Nucleic Acids Research, 2013 (online), vol. 42, pp. 1831-1844.*
Nilsson et al., Nucleic Acids Research, 2001, vol. 29, No. 2, pp. 578-581.*
Nilsson et al., Nature Biotechnology, 2000, vo. 18, pp. 791-793.*
Ho et al., Journal of Virology, 1997, vol. 71, pp. 1931-1937.*
Sriskanda et al., Nucleic Acids REsearch, 1998, vol. 26 pp. 3536-3541.*
Odell, et al, J. Biol. Chem., 274, 14032-14039, 1999.
Nilsson, et al, Nucleic Acids Research, 29, 2, 578-581, 2001.
Lohman, et al, Nucleic Acids Research, 42, 3, 1831-1844, 2014.
International Search Report for International Application No. PCT/US2013/076684, dated Mar. 19, 2014.
Yeakley, et al., Nat Biotechnol., 20(4):353-8 (2002).
Bullard and Bowater, Biochem. J., 398(1):135-44 (2006).
Li, et al., Curr Protoc Mol Biol. Apr; Chapter 4: Unit 4.13.1-9 (2012).
Li, et. al., Anal. Chem., 81 (12):4906-4913 (2009).
Absalan and Ronaghi, Methods in Molecular Biology, 396:315-330 (2007).
Nilsson, et al., Nature Biotechnology, 18:791-793 (2000).
Nilsson, et al., Science, 265, 2085-2088 (1994).
Nilsson, et al., Nat Genet. 16:252-255 (1997).
Barany, PCR Methods Appl., 1:5-16 (1991).
Landegren, Bioessays 15:761-765 (1993).
Wiedmann, et al., PCR Methods Appl. 3:S51-64 (1994).
Baner, et al., Nucleic Acids Res. 26:5073-5078 (1998).
Hardenbol, et al., Nature Biotechnol. 21:673-678 (2003).
Landegren, Methods Cell Biol. 75:787-797 (2004).
Sriskandas, et al., Nucleic Acid Research, 26:3536-3541 (1998).
Ho, et al., J. Virol., 71(3):1931 (1997).
Nair, et al., Nat. Struct. Mol. Biol., 14:770-778 (2007).
Nandakumar, Mol. Cell, 26:257-271 (2007).
Pascal, et al., Nature, 432:473-478 (2004).
Pease, et al., Proc. Natl. Acad. Sci. USA, 91(11):5022-5026 (1994).
Khrapko, et al., Mol Biol (Mosk) (USSR) 25:718-730 (1991).
Stimpson, et al., Proc. Natl. Acad. Sci. USA, 92:6379-6383 (1995).
Guo, et al., Nucleic Acids Res. 22:5456-5465 (1994).
Peng, et al., Anal Chem., 82(23):9727-35 (2010).
Syvanen, Nat Genet., 37 Suppl:S5-10, (2005).
Lu, et al., Biocimica et Biophysica Acta, 1701:37-48 (2004).
Notomi, et al., Nucleic Acids Research, 28(12):e63 (2000).
Mori, et al. Biochem. Biophys. res. Commun., 289:150-154 (2001).
Tomita, et al., Nat. Protocols, 3(5):877-82 (2008).
Goto, et al., BioTechniques, 46(3):167-71 (2009).
Gandelman, et al., PLoS One, 5:e14155 (2010).
Pourmand, et al., PNAS, 103(17):6466-70 (2006).

(Continued)

Primary Examiner — Mindy G Brown
(74) Attorney, Agent, or Firm — New England Biolabs, Inc; Harriet M. Strimpel

(57) ABSTRACT

Compositions and methods are provided for ligating polynucleotides having a length that is greater than 8 nucleotides on an RNA splint. The ligation reaction provides consistent results in high or low ATP concentrations. The reaction can occur rapidly and is generally at least 10 fold more efficient than T4DNA ligase under optimal conditions for T4DNA ligase and the reaction time is less than 6 hours for example, less than 1 hour.

16 Claims, 31 Drawing Sheets

Specification includes a Sequence Listing.

(56) References Cited

OTHER PUBLICATIONS http://www.ncbi.nlm.nih.gov/projects/genome/probe/doc/TechMIP.shtml.
Lohman et al, Nucleic Acids Res. 2014 42:1831-44.
Odell et al, Nucleic Acids Res. 2003 31: 5090-100.
Sriskanda et al, Nucleic Acids Res. 2002 30: 903-11.
Sriskanda et al, J Biol Chem. 2002 277: 9661-7.
Odell et al, Mol Cell. 2000 6: 1183-93.
Sriskanda et al, Nucleic Acids Res. 1999 27: 3953-63.
Sriskanda et al, Nucleic Acids Res. 1998 26: 4618-25.
Sriskanda et al, Nucleic Acids Res. 1998 26: 3536-41.
Sriskanda Nucleic Acids Res. 1998 26:505-31.
Doherty, et al., Structural and mechanistic conservation in DNA ligases, Nucleic Acids Research 28 :4051-4058 (2000).
Martin, et al., ATP-dependent DNA ligases, Genome Biol. 3: 3005.1-3005.7 (2002).
Ellenberger, et al., Eukaryotic DNA Ligases: Structural and Functional Insights, Annu Rev Biochem. 77: 313-338 (2008).
Schneider, et al., Efficient in situ detection of mRNAs using the Chlorella virus DNA ligase for padlock probe ligation RNA 2017 23:250-256 (see the entire paper).
Roy, et al., Assessing long-distance RNA sequence connectivity via RNA-templated DNA-DNA ligation eLife. 2015 4: e03700 (see Fig. 2, supplement 1).
Jin, et al., Sensitive and specific miRNA detection method using SplintR Ligase Nucleic Acids Res. 2016 44: e116 (see the entire paper).
Deng, et al., Highly specific imaging of mRNA in single cells by target RNA-initiated rolling circle amplification Chem. Sci., 2017, published online Mar. 7, 2017 (see the entire paper).

* cited by examiner

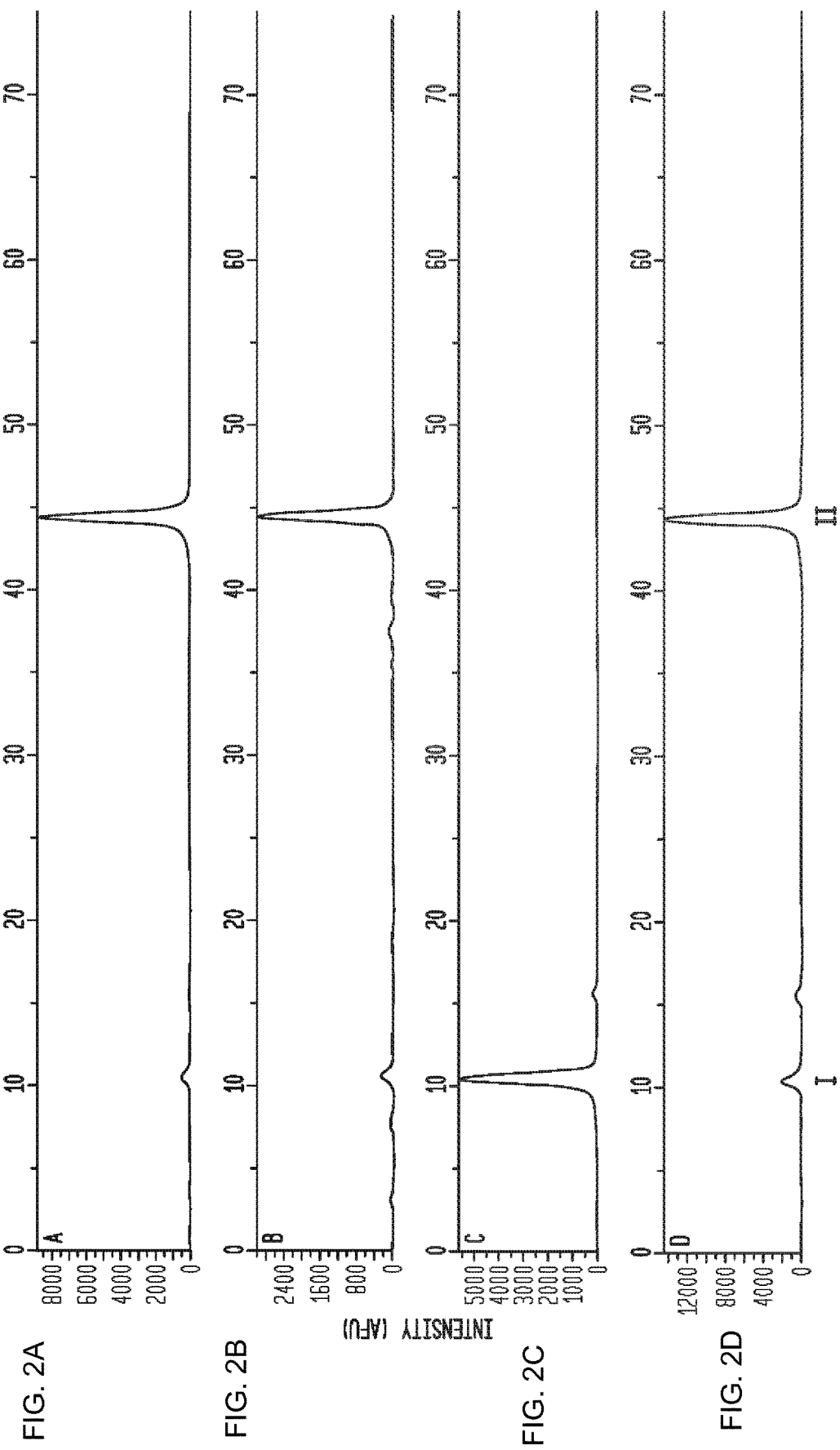

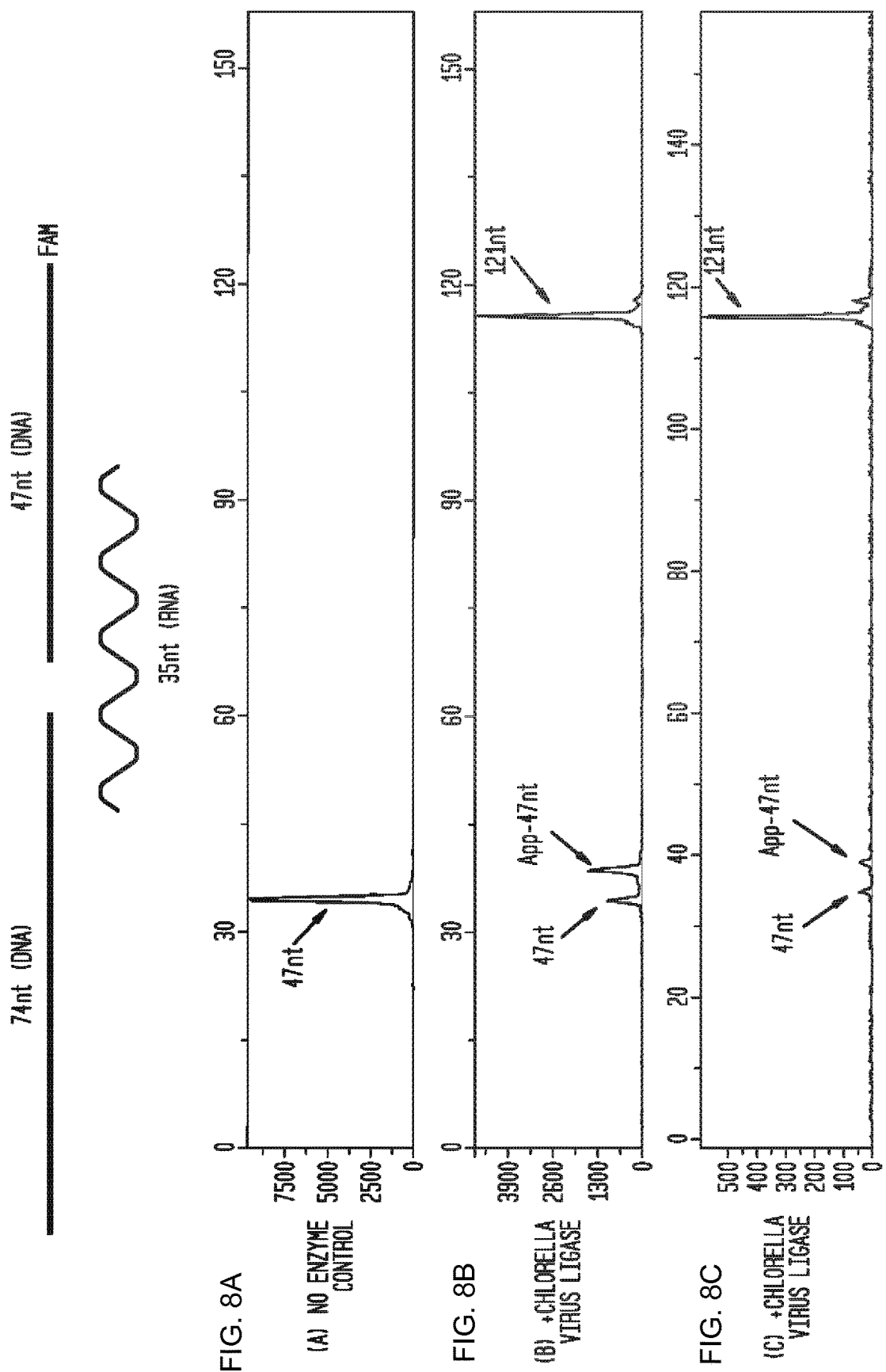

FIG. 9

MAITKPLLAATLENIEDVQFPCLATPKIDGIRSVKQTQMLSRTFKPIRNSVNNALLTELLPEGSDGEISIEGATFQDTTSAVMTGH
KMYNAKFSYYWFDYVTDDPLKKYIDRVEDMKNYITVHPHILEHAQVKIIPLIPVEINNITELLQYERDVLSKGFEGVMIRKPDGKY
KFGRSTLKEGILLKMKQFKDAEATIISMTALFKNTNTKTKONFGYSKRSTHKSGKVEEDVMGSIEVDYDGVVFSIGTGFDADXRRD
FWQMKESYIGKMVKFKYFEMGSKDCPAFPVFIGIRHEEDR (SEQ ID NO: 1)

5'-TATAACTTTACTTCTATTGC (SEQ ID NO: 2)

pTGATGGGACCTACAATGTACCAGAAGCGTC-FAM (SEQ ID NO: 3)

5'GACGCUUCUGGUACAUUGUAGGUCCCAUCAGCAAUAGAAGUAAAGUUAUA (SEQ ID NO: 4)

|   | A | B | C | D |
|---|---|---|---|---|
| 1 | 2747519 | CAAACACCATTGTCACACTCCACTAG | miR-122 | |
| 2 | 1920107 | CATCACCTTCCTTCTCCTCCACTAGC | miR-765 | |
| 3 | 805920 | ACCCCTATCACGATTAGCATTAACTA | miR-155-5p | |
| 4 | 768197 | CCTCCAGTCCTTGCACCGAGACCTAG | miR-678 | |
| 5 | 768065 | AGAGCTACAGTGCTTCATCTCACTAG | miR-143 | |
| 6 | 484269 | CCTGGCACACAGTAGGACCTTCACTA | miR-493-3p | |
| 7 | 472639 | ACGCTCAAATGTCGCAGCACTTTCTA | miR-372-3p | |
| 8 | 462981 | CTACCTGCACTGTAAGCACTTTGCTA | miR-17-5p | |
| 9 | 315662 | CGTACGCTATACGGTCTACTACTAGC | miR-411-5p | |
| 10 | 311028 | CCTACGTTCCATAGTCTACCACTAGC | miR-379-5p | |
| 11 | 193170 | CACAAGTTCGGATCTACGGGTTCTAG | miR-100-5p | |
| 12 | 186006 | TCTACGGGTTCTAGCAGCCTGACATC | no match | |
| 13 | 161376 | TTCCCATGCCCTATACCTCTCTAGCA | miR-202-3p | |
| 14 | 115034 | CTGTTCCTGCTGAACTGAGCCACTAG | miR-24-3p | |
| 15 | 96902 | ACCAGGTTCCACCCCAGCAGGCCTAG | mir-370 | |
| 16 | 83354 | TTGTCTAACCAGTCACCTGTTCTAGC | mir-522 | |
| 17 | 75582 | CAGCTATGCCAGCATCTTGCCTCTAG | miR-31-5p | |
| 18 | 57253 | TCAACATCAGTCTGATAAGCTACTAG | miR-21-5p | |
| 19 | 43130 | GCTCTAAGAAAGCCACACTCTAGCAG | miR-644a-3p | |
| 20 | 42389 | ACACTCTAAAGGGAA | miR-522-3p | |
| 21 | 30447 | AAGAACAATGCCTTACTGAGTACTAG | miR-201-5p | |
| 22 | 29157 | CCTGTCACACAGTAGGACCTTCACTA | miR-493-3p | 1 mismatch |
| 23 | 28263 | TCACAGGTTAAAGGGTCTCAGGGACT | miR-125-5p | |
| 24 | 26908 | CTACCTGCACTGTAAGCACTTTTCTA | miR-106a-5p | |
| 25 | 26170 | CGCCAATATTTACGTGCTGCTACTAG | miR-16-5p | |
| 26 | 22766 | ACAGAGAGCTTGCCCTTGTATACTAG | miR-381-3p | |
| 27 | 22335 | TCCATCATCAAAACAAATGGAGTCTA | miR-136-5p | |
| 28 | 17010 | AAGAACAATGCCTTTGTGTGATCTAG | miR-377-3p | half site |
| 29 | 16608 | CCTGGCACACAGTATGACCTTCACTA | miR-493-3p | |
| 30 | 16478 | ACAATCCTAGCCTTCACTAGCAGCCT | no match | |
| 31 | 16320 | AACACTGATTTCAAATGGTGCTACTA | miR-29b-3p | |
| 32 | 13253 | AAAGAGACCGGTTCACTGTGACTAGC | miR-128-3p | |
| 33 | 12260 | CCTCCAGTCTAGCCACACTCTAGCAG | no match | |
| 34 | 11292 | CACAAGTTCGGATCTACGTGTTCTAG | miR-100-5p | 1 mismatch |
| 35 | 10912 | ACCGACCGACCGATCGACCGACTAGC | miR-341-3p | |
| 36 | 10644 | TCATCATTACCAGGCAGTATTACTAG | miR-200b-3p | |
| 37 | 10340 | GAGGGAGGGCTGATAAGCTACTAGCA | no match | |
| 38 | 8227 | ACGCTCAAGATGTGCTGCTACTAGCA | miR-15b-5p | 5 nt short |
| 39 | 7873 | ACAAAAGTTGCCTTTGTGTGATCTAG | miR-377-3p | |
| 40 | 6921 | TTCCCATTCCCTATACCTCTCTAGCA | miR-202-3p | 1 mismatch |

*FIG. 13C*

| | Probe B | | | | | | | | | | | Probe A | |
|---|---|---|---|---|---|---|---|---|---|---|---|---|---|
| | | 5' ug | ga | gu | gu | ga | ca | au | gg | ug | uu | ug | |
| | | | | | | | | | | | | | |
| 3' | GGGACGCGCACAGAGGCTGAGTC | AC-CT | CA | CA | CT | GT | TA | CC | AC | AA | AC | AGTGGCTGACGGGTATCTCTCC-FAM 5' | 1 |
| 3' | GGGACGCGCACAGAGGCTGAGTC | AC | CT-CA | CT | GT | TA | CC | AC | AA | AC | AGTGGCTGACGGGTATCTCTCC-FAM 5' | 2 |
| 3' | GGGACGCGCACAGAGGCTGAGTC | AC | CT | CA-CA | CT | GT | TA | CC | AC | AA | AC | AGTGGCTGACGGGTATCTCTCC-FAM 5' | 3 |
| 3' | GGGACGCGCACAGAGGCTGAGTC | AC | CT | CA | CA-CT | GT | TA | CC | AC | AA | AC | AGTGGCTGACGGGTATCTCTCC-FAM 5' | 4 |
| 3' | GGGACGCGCACAGAGGCTGAGTC | AC | CT | CA | CA | CT-GT | TA | CC | AC | AA | AC | AGTGGCTGACGGGTATCTCTCC-FAM 5' | 5 |
| 3' | GGGACGCGCACAGAGGCTGAGTC | AC | CT | CA | CA | CT | GT-TA | CC | AC | AA | AC | AGTGGCTGACGGGTATCTCTCC-FAM 5' | 6 |
| 3' | GGGACGCGCACAGAGGCTGAGTC | AC | CT | CA | CA | CT | GT | TA-CC | AC | AA | AC | AGTGGCTGACGGGTATCTCTCC-FAM 5' | 7 |
| 3' | GGGACGCGCACAGAGGCTGAGTC | AC | CT | CA | CA | CT | GT | TA | CC-AC | AA | AC | AGTGGCTGACGGGTATCTCTCC-FAM 5' | 8 |
| 3' | GGGACGCGCACAGAGGCTGAGTC | AC | CT | CA | CA | CT | GT | TA | CC | AC-AA | AC | AGTGGCTGACGGGTATCTCTCC-FAM 5' | 9 |
| 3' | GGGACGCGCACAGAGGCTGAGTC | AC | CT | CA | CA | CT | GT | TA | CC | AC | AA-AC | AGTGGCTGACGGGTATCTCTCC-FAM 5' | 10 |

FIG. 14A

```
Let-7a:  5'UGAGGUAGUAGGUUGUAUAGUU
Let-7b:  5'UGAGGUAGUAGGUUGUGUGGUU
Let-7c:  5'UGAGGUAGUAGGUUGUAUGGUU
Let-7d:  5'AGAGGUAGUAGGUUGCAUAGUU
Let-7e:  5'UGAGGUAGGAGGUUGUAUAGUU
Let-7f:  5'UGAGGUAGUAGAUUGUAUAGUU
Let-7g:  5'UGAGGUAGUAGUUUGUACAGUU
Let-7i:  5'UGAGGUAGUAGUUUGUGCUGUU
```

FIG. 17A

```
5' UGAGGUAGUAGUUUGU ACAGUU 3'
   ACTCCATCATCAAACA TGTCAA —————— FAM 5'  A8.0/88.0
3'
```

FIG. 17B

Let-7 Family Isoforms

```
Let-7a:  5'U G A G G U A G U A G G U U G U A|U A G U U
Let-7b:  5'U G A G G U A G U A G G U U G U G|U G G U U
Let-7c:  5'U G A G G U A G U A G G U U G U A|U G G U U
Let-7d:  5'A G A G G U A G U A G G U U G C A|U A G U U
Let-7e:  5'U G A G G U A G G A G G U U G U A|U A G U U
Let-7f:  5'U G A G G U A G U A G A U U G U A|U A G U U
Let-7g:  5'U G A G G U A G U A G U U U G U A|C A G U U
Let-7i:  5'U G A G G U A G U A G U U U G U G|C U G U U

Let-7a:  5'U G A G G U A G U A G G U U G U A U|A G U U
Let-7b:  5'U G A G G U A G U A G G U U G U G U|G G U U
Let-7c:  5'U G A G G U A G U A G G U U G U A U|G G U U
Let-7d:  5'A G A G G U A G U A G G U U G C A U|A G U U
Let-7e:  5'U G A G G U A G G A G G U U G U A U|A G U U
Let-7f:  5'U G A G G U A G U A G A U U G U A U|A G U U
Let-7g:  5'U G A G G U A G U A G U U U G U A C|A G U U
Let-7i:  5'U G A G G U A G U A G U U U G U G C|U G U U

Let-7a:  5'U G A G G U A G U A G G U U G U|A U A G U U
Let-7b:  5'U G A G G U A G U A G G U U G U|G U G G U U
Let-7c:  5'U G A G G U A G U A G G U U G U|A U G G U U
Let-7d:  5'A G A G G U A G U A G G U U G C|A U A G U U
Let-7e:  5'U G A G G U A G G A G G U U G U|A U A G U U
Let-7f:  5'U G A G G U A G U A G A U U G U|A U A G U U
Let-7g:  5'U G A G G U A G U A G U U U G U|A C A G U U
Let-7i:  5'U G A G G U A G U A G U U U G U|G C U G U U
```

FIG. 17D

Let-7b

```
                                                    Stacking
         5' UGAGGUAGUAGGUUGUG UGGUU 3' ─────────────
3' ─────────── ACTCCATCATCCAACAC│ACCAA ────────────────── FAM
Let-7b probes:          B17                A5
```

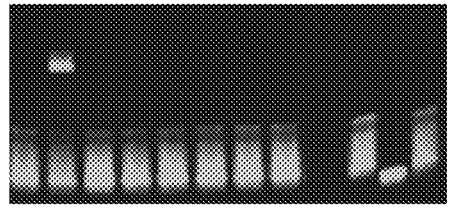

Let-7c

```
                                                    Stacking
         5' UGAGGUAGUAGGUUGUAU GGUU 3' ─────────────
3' ─────────── ACTCCATCATCCAACATA│CCAA ────────────────── FAM
Let-7c probes:          B18                A4
```

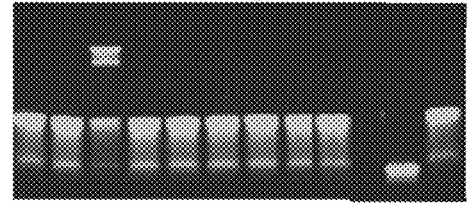

Let-7g

```
         5' UGAGGUAGUAGUUUGU ACAGUU 3'
3' ─────────── ACTCCATCATCAAACA│TGTCAA ────────────────── FAM
Let-7g probes:          B16                A6
```

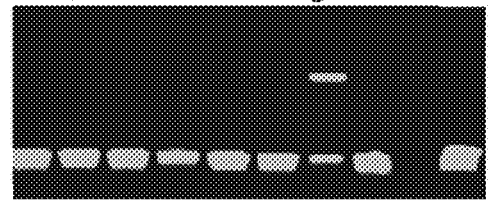

*FIG. 17E*

| | | | | | | | | | | | | | | | | | | | | | | | | Ave Cq | Delta Cq | % of 7b |
|---|---|---|---|---|---|---|---|---|---|---|---|---|---|---|---|---|---|---|---|---|---|---|---|---|---|---|
| Let-7-a: | 5' | U | G | A | G | G | U | A | G | U | A | G | G | U | U | G | U | A | U | A | G | U | U | 25.5 | 7.5 | 0.5% |
| Let-7-b: | 5' | U | G | A | G | G | U | A | G | U | A | G | G | U | U | G | U | G | U | G | G | U | U | 18.0 | 0.0 | 100% |
| Let-7-c: | 5' | U | G | A | G | G | U | A | G | U | A | G | G | U | U | G | U | A | U | G | G | U | U | 23.5 | 5.5 | 2.2% |
| Let-7-d: | 5' | A | G | A | G | G | U | A | G | U | A | G | G | U | U | G | C | A | U | A | G | U | U | 25.3 | 7.2 | 0.7% |
| Let-7-e: | 5' | U | G | A | G | G | U | A | G | G | A | G | G | U | U | G | U | A | U | A | G | U | U | 24.2 | 6.4 | 1.2% |
| Let-7-f: | 5' | U | G | A | G | G | U | A | G | U | A | G | A | U | U | G | U | A | U | A | G | U | U | 25.4 | 8.3 | 0.3% |
| Let-7-g: | 5' | U | G | A | G | G | U | A | G | U | A | G | U | U | U | G | U | A | C | A | G | U | U | 25.1 | 7.3 | 0.6% |
| Let-7-i: | 5' | U | G | A | G | G | U | A | G | U | A | G | U | U | U | G | U | G | C | U | G | U | U | 24.9 | 7.1 | 0.7% |

FIG. 18A miR-Let-7b

5'UGAGGUAGGUUGUGUGGUUU 3'
   ACTCCATCCAAACACACCAA———FAM 5'

FIG. 18B

SEQUENCE LISTING

<160> NUMBER OF SEQ ID NOS: 118

<210> SEQ ID NO 1

<211> LENGTH: 298
<212> TYPE: PRT
<213> ORGANISM: Chlorella virus

<400> SEQUENCE: 1

```
Met Ala Ile Thr Lys Pro Leu Leu Ala Ala Thr Leu Glu Asn Ile Glu
1               5                   10                  15

Asp Val Gln Phe Pro Cys Leu Ala Thr Pro Lys Ile Asp Gly Ile Arg
            20                  25                  30

Ser Val Lys Gln Thr Gln Met Leu Ser Arg Thr Phe Lys Pro Ile Arg
        35                  40                  45

Asn Ser Val Met Asn Arg Leu Leu Thr Glu Leu Leu Pro Glu Gly Ser
    50                  55                  60

Asp Gly Glu Ile Ser Ile Glu Gly Ala Thr Phe Gln Asp Thr Thr Ser
65                  70                  75                  80

Ala Val Met Thr Gly His Lys Met Tyr Asn Ala Lys Phe Ser Tyr Tyr
                85                  90                  95

Trp Phe Asp Tyr Val Thr Asp Pro Leu Lys Lys Tyr Ile Asp Arg
            100                 105                 110

Val Glu Asp Met Lys Asn Tyr Ile Thr Val His Pro His Ile Leu Glu
        115                 120                 125

His Ala Gln Val Lys Ile Ile Pro Leu Ile Pro Val Glu Ile Asn Asn
    130                 135                 140

Ile Thr Glu Leu Leu Gln Tyr Glu Arg Asp Val Leu Ser Lys Gly Phe
145                 150                 155                 160

Glu Gly Val Met Ile Arg Lys Pro Asp Gly Lys Tyr Lys Phe Gly Arg
                165                 170                 175

Ser Thr Leu Lys Glu Gly Ile Leu Leu Lys Met Lys Gln Phe Lys Asp
            180                 185                 190

Ala Glu Ala Thr Ile Ile Ser Met Thr Ala Leu Phe Lys Asn Thr Asn
        195                 200                 205

Thr Lys Thr Lys Asp Asn Phe Gly Tyr Ser Lys Arg Ser Thr His Lys
    210                 215                 220

Ser Gly Lys Val Glu Glu Asp Val Met Gly Ser Ile Glu Val Asp Tyr
225                 230                 235                 240

Asp Gly Val Val Phe Ser Ile Gly Thr Gly Phe Asp Ala Asp Gln Arg
                245                 250                 255

Arg Asp Phe Trp Gln Asn Lys Glu Ser Tyr Ile Gly Lys Met Val Lys
            260                 265                 270

Phe Lys Tyr Phe Glu Met Gly Ser Lys Asp Cys Pro Arg Phe Pro Val
        275                 280                 285

Phe Ile Gly Ile Arg His Glu Glu Asp Arg
    290                 295
```

<210> SEQ ID NO 2
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 2
tataacttta cttctattgc                                           20

<210> SEQ ID NO 3
<211> LENGTH: 30
<212> TYPE: DNA

```
<213> ORGANISM: Artificial sequence
<220> FEATURE:
<223> OTHER INFORMATION: synthetic polynucleotide

<400> SEQUENCE: 3
tgatgggacc tacaatgtac cagaagcgtc                                    30

<210> SEQ ID NO 4
<211> LENGTH: 50
<212> TYPE: RNA
<213> ORGANISM: Artificial sequence
<220> FEATURE:
<223> OTHER INFORMATION: synthetic polynucleotide

<400> SEQUENCE: 4
gacgcuucug guacauugua ggucccauca gcaauagaag uaaaguuaua              50

<210> SEQ ID NO 5
<211> LENGTH: 37
<212> TYPE: DNA
<213> ORGANISM: Artificial sequence
<220> FEATURE:
<223> OTHER INFORMATION: synthetic polynucleotide

<400> SEQUENCE: 5
cggtaagacc tttcggtact agatcggaag agcacac                            37

<210> SEQ ID NO 6
<211> LENGTH: 37
<212> TYPE: DNA
<213> ORGANISM: Artificial sequence
<220> FEATURE:
<223> OTHER INFORMATION: synthetic polynucleotide

<400> SEQUENCE: 6
ggaagccttg gcttttggaa cgttgcgtcg agttttc                            37

<210> SEQ ID NO 7
<211> LENGTH: 17
<212> TYPE: DNA
<213> ORGANISM: Artificial sequence
<220> FEATURE:
<223> OTHER INFORMATION: synthetic polynucleotide

<400> SEQUENCE: 7
gtgtgctctt ccgatct                                                  17

<210> SEQ ID NO 8
<211> LENGTH: 17
<212> TYPE: DNA
<213> ORGANISM: Artificial sequence
<220> FEATURE:
<223> OTHER INFORMATION: synthetic polynucleotide

<400> SEQUENCE: 8
ggaagccttg gcttttg                                                  17

<210> SEQ ID NO 9
<211> LENGTH: 22
<212> TYPE: RNA
<213> ORGANISM: Artificial sequence
<220> FEATURE:
<223> OTHER INFORMATION: synthetic polynucleotide

<400> SEQUENCE: 9
uggaguguga caaugguguu ug                                            22
```

<210> SEQ ID NO 10
<211> LENGTH: 32
<212> TYPE: DNA
<213> ORGANISM: Artificial sequence
<220> FEATURE:
<223> OTHER INFORMATION: synthetic polynucleotide

<400> SEQUENCE: 10
gtcacactcc tctgagtcgg agacacgcag gg                          32

<210> SEQ ID NO 11
<211> LENGTH: 33
<212> TYPE: DNA
<213> ORGANISM: Artificial sequence
<220> FEATURE:
<223> OTHER INFORMATION: synthetic polynucleotide

<400> SEQUENCE: 11
cctctctatg ggcagtcggt gataaacacc att                         33

<210> SEQ ID NO 12
<211> LENGTH: 30
<212> TYPE: DNA
<213> ORGANISM: Artificial sequence
<220> FEATURE:
<223> OTHER INFORMATION: synthetic polynucleotide

<400> SEQUENCE: 12
ccatctcatc cctgcgtgtc tccgactcag                             30

<210> SEQ ID NO 13
<211> LENGTH: 41
<212> TYPE: DNA
<213> ORGANISM: Artificial sequence
<220> FEATURE:
<223> OTHER INFORMATION: synthetic polynucleotide

<400> SEQUENCE: 13
ccactacgcc tccgctttcc tctctatggg cagtcggtga t                41

<210> SEQ ID NO 14
<211> LENGTH: 32
<212> TYPE: DNA
<213> ORGANISM: Artificial sequence
<220> FEATURE:
<223> OTHER INFORMATION: synthetic polynucleotide

<400> SEQUENCE: 14
cctctctatg ggcagtcggt gcaaacacca tt                          32

<210> SEQ ID NO 15
<211> LENGTH: 32
<212> TYPE: DNA
<213> ORGANISM: Artificial sequence
<220> FEATURE:
<223> OTHER INFORMATION: synthetic polynucleotide

<400> SEQUENCE: 15
gtcacactcc actgagtcgg agacacgcag gg                          32

<210> SEQ ID NO 16
<211> LENGTH: 22
<212> TYPE: RNA
<213> ORGANISM: Artificial sequence
<220> FEATURE:

<223> OTHER INFORMATION: synthetic polynucleotide

<400> SEQUENCE: 16
uggaguguga caauguguu ug                                    22

<210> SEQ ID NO 17
<211> LENGTH: 41
<212> TYPE: DNA
<213> ORGANISM: Artificial sequence
<220> FEATURE:
<223> OTHER INFORMATION: synthetic polynucleotide

<400> SEQUENCE: 17
cctctctatg ggcagtcggt gcaaacacca ttgtcacact c              41

<210> SEQ ID NO 18
<211> LENGTH: 39
<212> TYPE: DNA
<213> ORGANISM: Artificial sequence
<220> FEATURE:
<223> OTHER INFORMATION: synthetic polynucleotide

<400> SEQUENCE: 18
cctctctatg ggcagtcggt gcaaacacca ttgtcacac                 39

<210> SEQ ID NO 19
<211> LENGTH: 37
<212> TYPE: DNA
<213> ORGANISM: Artificial sequence
<220> FEATURE:
<223> OTHER INFORMATION: synthetic polynucleotide

<400> SEQUENCE: 19
cctctctatg ggcagtcggt gcaaacacca ttgtcac                   37

<210> SEQ ID NO 20
<211> LENGTH: 35
<212> TYPE: DNA
<213> ORGANISM: Artificial sequence
<220> FEATURE:
<223> OTHER INFORMATION: synthetic polynucleotide

<400> SEQUENCE: 20
cctctctatg ggcagtcggt gcaaacacca ttgtc                     35

<210> SEQ ID NO 21
<211> LENGTH: 33
<212> TYPE: DNA
<213> ORGANISM: Artificial sequence
<220> FEATURE:
<223> OTHER INFORMATION: synthetic polynucleotide

<400> SEQUENCE: 21
cctctctatg ggcagtcggt gcaaacacca ttg                       33

<210> SEQ ID NO 22
<211> LENGTH: 31
<212> TYPE: DNA
<213> ORGANISM: Artificial sequence
<220> FEATURE:
<223> OTHER INFORMATION: synthetic polynucleotide

<400> SEQUENCE: 22
cctctctatg ggcagtcggt gcaaacacca t                         31

<210> SEQ ID NO 23
<211> LENGTH: 29
<212> TYPE: DNA
<213> ORGANISM: Artificial sequence
<220> FEATURE:
<223> OTHER INFORMATION: synthetic polynucleotide

<400> SEQUENCE: 23
cctctctatg ggcagtcggt gcaaacacc                                    29

<210> SEQ ID NO 24
<211> LENGTH: 27
<212> TYPE: DNA
<213> ORGANISM: Artificial sequence
<220> FEATURE:
<223> OTHER INFORMATION: synthetic polynucleotide

<400> SEQUENCE: 24
cctctctatg ggcagtcggt gcaaaca                                      27

<210> SEQ ID NO 25
<211> LENGTH: 25
<212> TYPE: DNA
<213> ORGANISM: Artificial sequence
<220> FEATURE:
<223> OTHER INFORMATION: synthetic polynucleotide

<400> SEQUENCE: 25
cctctctatg ggcagtcggt gcaaa                                        25

<210> SEQ ID NO 26
<211> LENGTH: 23
<212> TYPE: DNA
<213> ORGANISM: Artificial sequence
<220> FEATURE:
<223> OTHER INFORMATION: synthetic polynucleotide

<400> SEQUENCE: 26
cctctctatg ggcagtcggt gca                                          23

<210> SEQ ID NO 27
<211> LENGTH: 23
<212> TYPE: DNA
<213> ORGANISM: Artificial sequence
<220> FEATURE:
<223> OTHER INFORMATION: synthetic polynucleotide

<400> SEQUENCE: 27
cactgagtcg gagacacgca ggg                                          23

<210> SEQ ID NO 28
<211> LENGTH: 25
<212> TYPE: DNA
<213> ORGANISM: Artificial sequence
<220> FEATURE:
<223> OTHER INFORMATION: synthetic polynucleotide

<400> SEQUENCE: 28
tccactgagt cggagacacg caggg                                        25

<210> SEQ ID NO 29
<211> LENGTH: 27
<212> TYPE: DNA
<213> ORGANISM: Artificial sequence
<220> FEATURE:
<223> OTHER INFORMATION: synthetic polynucleotide

<400> SEQUENCE: 29
actccactga gtcggagaca cgcaggg                    27

<210> SEQ ID NO 30
<211> LENGTH: 29
<212> TYPE: DNA
<213> ORGANISM: Artificial sequence
<220> FEATURE:
<223> OTHER INFORMATION: synthetic polynucleotide

<400> SEQUENCE: 30
acactccact gagtcggaga cacgcaggg                  29

<210> SEQ ID NO 31
<211> LENGTH: 31
<212> TYPE: DNA
<213> ORGANISM: Artificial sequence
<220> FEATURE:
<223> OTHER INFORMATION: synthetic polynucleotide

<400> SEQUENCE: 31
tcacactcca ctgagtcgga gacacgcagg g               31

<210> SEQ ID NO 32
<211> LENGTH: 33
<212> TYPE: DNA
<213> ORGANISM: Artificial sequence
<220> FEATURE:
<223> OTHER INFORMATION: synthetic polynucleotide

<400> SEQUENCE: 32
tgtcacactc cactgagtcg gagacacgca ggg             33

<210> SEQ ID NO 33
<211> LENGTH: 35
<212> TYPE: DNA
<213> ORGANISM: Artificial sequence
<220> FEATURE:
<223> OTHER INFORMATION: synthetic polynucleotide

<400> SEQUENCE: 33
attgtcacac tccactgagt cggagacacg caggg           35

<210> SEQ ID NO 34
<211> LENGTH: 37
<212> TYPE: DNA
<213> ORGANISM: Artificial sequence
<220> FEATURE:
<223> OTHER INFORMATION: synthetic polynucleotide

<400> SEQUENCE: 34
ccattgtcac actccactga gtcggagaca cgcaggg         37

<210> SEQ ID NO 35
<211> LENGTH: 39
<212> TYPE: DNA
<213> ORGANISM: Artificial sequence
<220> FEATURE:
<223> OTHER INFORMATION: synthetic polynucleotide

<400> SEQUENCE: 35
caccattgtc acactccact gagtcggaga cacgcaggg       39

<210> SEQ ID NO 36
<211> LENGTH: 41

<212> TYPE: DNA
<213> ORGANISM: Artificial sequence
<220> FEATURE:
<223> OTHER INFORMATION: synthetic polynucleotide

<400> SEQUENCE: 36
aacaccattg tcacactcca ctgagtcgga gacacgcagg g        41

<210> SEQ ID NO 37
<211> LENGTH: 37
<212> TYPE: DNA
<213> ORGANISM: Artificial sequence
<220> FEATURE:
<223> OTHER INFORMATION: synthetic polynucleotide

<400> SEQUENCE: 37
ctcgacctct ctatgggcag tcacgaccaa acaccat        37

<210> SEQ ID NO 38
<211> LENGTH: 33
<212> TYPE: DNA
<213> ORGANISM: Artificial sequence
<220> FEATURE:
<223> OTHER INFORMATION: synthetic polynucleotide

<400> SEQUENCE: 38
tgtcacactc cactgagtcg gagacacgca ggg        33

<210> SEQ ID NO 39
<211> LENGTH: 19
<212> TYPE: DNA
<213> ORGANISM: Artificial sequence
<220> FEATURE:
<223> OTHER INFORMATION: synthetic polynucleotide

<400> SEQUENCE: 39
gctcgacctc tctatgggc        19

<210> SEQ ID NO 40
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 40
ccctgcgtgt ctccgactca g        21

<210> SEQ ID NO 41
<211> LENGTH: 22
<212> TYPE: RNA
<213> ORGANISM: Artificial sequence
<220> FEATURE:
<223> OTHER INFORMATION: synthetic polynucleotide

<400> SEQUENCE: 41
uggaguguga caauggguguu ug        22

<210> SEQ ID NO 42
<211> LENGTH: 14
<212> TYPE: DNA
<213> ORGANISM: Artificial sequence
<220> FEATURE:
<223> OTHER INFORMATION: synthetic polynucleotide

<400> SEQUENCE: 42
cacgaccaaa cacc                                                         14

<210> SEQ ID NO 43
<211> LENGTH: 28
<212> TYPE: DNA
<213> ORGANISM: Artificial sequence
<220> FEATURE:
<223> OTHER INFORMATION: synthetic polynucleotide

<400> SEQUENCE: 43
cctctctatg ggcagtcggt gaaactgt                                          28

<210> SEQ ID NO 44
<211> LENGTH: 37
<212> TYPE: DNA
<213> ORGANISM: Artificial sequence
<220> FEATURE:
<223> OTHER INFORMATION: synthetic polynucleotide

<400> SEQUENCE: 44
acaaactact acctcactga gtcggagaca cgcaggg                                37

<210> SEQ ID NO 45
<211> LENGTH: 46
<212> TYPE: DNA
<213> ORGANISM: Artificial sequence
<220> FEATURE:
<223> OTHER INFORMATION: synthetic polynucleotide

<400> SEQUENCE: 45
gtctggtcag aatcacctcc tcgtcatggg caggtacggt gcaacc                      46

<210> SEQ ID NO 46
<211> LENGTH: 39
<212> TYPE: DNA
<213> ORGANISM: Artificial sequence
<220> FEATURE:
<223> OTHER INFORMATION: synthetic polynucleotide

<400> SEQUENCE: 46
acacaaccta ctacctcact gagttggaga cacgcagaa                              39

<210> SEQ ID NO 47
<211> LENGTH: 24
<212> TYPE: DNA
<213> ORGANISM: Artificial sequence
<220> FEATURE:
<223> OTHER INFORMATION: synthetic polynucleotide

<400> SEQUENCE: 47
cgtcatgggc aggtacggtg caac                                              24

<210> SEQ ID NO 48
<211> LENGTH: 19
<212> TYPE: DNA
<213> ORGANISM: Artificial sequence
<220> FEATURE:
<223> OTHER INFORMATION: synthetic polynucleotide

<400> SEQUENCE: 48
gtctggtcag aatcacctc                                                    19

<210> SEQ ID NO 49
<211> LENGTH: 20
<212> TYPE: DNA
<213> ORGANISM: Artificial sequence

```
<220> FEATURE:
<223> OTHER INFORMATION: synthetic polynucleotide

<400> SEQUENCE: 49
ttctgcgtgt ctccaactca                                                    20

<210> SEQ ID NO 50
<211> LENGTH: 22
<212> TYPE: RNA
<213> ORGANISM: Artificial sequence
<220> FEATURE:
<223> OTHER INFORMATION: synthetic polynucleotide

<400> SEQUENCE: 50
ugagguagua gguuguauag uu                                                 22

<210> SEQ ID NO 51
<211> LENGTH: 22
<212> TYPE: RNA
<213> ORGANISM: Artificial sequence
<220> FEATURE:
<223> OTHER INFORMATION: synthetic polynucleotide

<400> SEQUENCE: 51
ugagguagua gguugugugg uu                                                 22

<210> SEQ ID NO 52
<211> LENGTH: 22
<212> TYPE: RNA
<213> ORGANISM: Artificial sequence
<220> FEATURE:
<223> OTHER INFORMATION: synthetic polynucleotide

<400> SEQUENCE: 52
ugagguagua gguuguaugg uu                                                 22

<210> SEQ ID NO 53
<211> LENGTH: 22
<212> TYPE: RNA
<213> ORGANISM: Artificial sequence
<220> FEATURE:
<223> OTHER INFORMATION: synthetic polynucleotide

<400> SEQUENCE: 53
agagguagua gguugcauag uu                                                 22

<210> SEQ ID NO 54
<211> LENGTH: 22
<212> TYPE: RNA
<213> ORGANISM: Artificial sequence
<220> FEATURE:
<223> OTHER INFORMATION: synthetic polynucleotide

<400> SEQUENCE: 54
ugagguagga gguuguauag uu                                                 22

<210> SEQ ID NO 55
<211> LENGTH: 22
<212> TYPE: RNA
<213> ORGANISM: Artificial sequence
<220> FEATURE:
<223> OTHER INFORMATION: synthetic polynucleotide

<400> SEQUENCE: 55
ugagguagua gauuguauag uu                                                 22
```

<210> SEQ ID NO 56
<211> LENGTH: 22
<212> TYPE: RNA
<213> ORGANISM: Artificial sequence
<220> FEATURE:
<223> OTHER INFORMATION: synthetic polynucleotide

<400> SEQUENCE: 56
ugagguagua guuuguacag uu                                        22

<210> SEQ ID NO 57
<211> LENGTH: 22
<212> TYPE: RNA
<213> ORGANISM: Artificial sequence
<220> FEATURE:
<223> OTHER INFORMATION: synthetic polynucleotide

<400> SEQUENCE: 57
ugagguagua guuugugcug uu                                        22

<210> SEQ ID NO 58
<211> LENGTH: 27
<212> TYPE: DNA
<213> ORGANISM: Artificial sequence
<220> FEATURE:
<223> OTHER INFORMATION: synthetic polynucleotide

<400> SEQUENCE: 58
cctctctatg ggcagtcggt gaaacca                                   27

<210> SEQ ID NO 59
<211> LENGTH: 38
<212> TYPE: DNA
<213> ORGANISM: Artificial sequence
<220> FEATURE:
<223> OTHER INFORMATION: synthetic polynucleotide

<400> SEQUENCE: 59
cacaacctac tacctcactg agtcggagac acgcaggg                       38

<210> SEQ ID NO 60
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 60
tcaccgactg cccatagaga gg                                        22

<210> SEQ ID NO 61
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 61
caaacaccat tgtcacactc cactag                                    26

<210> SEQ ID NO 62
<211> LENGTH: 26
<212> TYPE: DNA
<213> ORGANISM: Artificial sequence
<220> FEATURE:
<223> OTHER INFORMATION: synthetic polynucleotide

```
<400> SEQUENCE: 62
catcaccttc cttctcctcc actagc                                            26

<210> SEQ ID NO 63
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 63
acccctatca cgattagcat taacta                                            26

<210> SEQ ID NO 64
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 64
cctccagtcc ttgcaccgag acctag                                            26

<210> SEQ ID NO 65
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 65
agagctacag tgcttcatct cactag                                            26

<210> SEQ ID NO 66
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 66
cctggcacac agtaggacct tcacta                                            26

<210> SEQ ID NO 67
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 67
acgctcaaat gtcgcagcac tttcta                                            26

<210> SEQ ID NO 68
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 68
ctacctgcac tgtaagcact ttgcta                                            26

<210> SEQ ID NO 69
```

```
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 69
cgtacgctat acggtctact actagc                                              26

<210> SEQ ID NO 70
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 70
cctacgttcc atagtctacc actagc                                              26

<210> SEQ ID NO 71
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 71
cacaagttcg gatctacggg ttctag                                              26

<210> SEQ ID NO 72
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 72
tctacgggtt ctagcagcct gacatc                                              26

<210> SEQ ID NO 73
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 73
ttcccatgcc ctatacctct ctagca                                              26

<210> SEQ ID NO 74
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 74
ctgttcctgc tgaactgagc cactag                                              26

<210> SEQ ID NO 75
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 75
```

```
accaggttcc accccagcag gcctag                                              26

<210> SEQ ID NO 76
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 76
ttgtctaacc agtcacctgt tctagc                                              26

<210> SEQ ID NO 77
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 77
cagctatgcc agcatcttgc ctctag                                              26

<210> SEQ ID NO 78
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 78
tcaacatcag tctgataagc tactag                                              26

<210> SEQ ID NO 79
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 79
gctctaagaa agccacactc tagcag                                              26

<210> SEQ ID NO 80
<211> LENGTH: 15
<212> TYPE: DNA
<213> ORGANISM: Artificial sequence
<220> FEATURE:
<223> OTHER INFORMATION: synthetic polynucleotide

<400> SEQUENCE: 80
acactctaaa gggaa                                                          15

<210> SEQ ID NO 81
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 81
aagaacaatg ccttactgag tactag                                              26

<210> SEQ ID NO 82
<211> LENGTH: 26
<212> TYPE: DNA
```

<213> ORGANISM: Artificial sequence
<220> FEATURE:
<223> OTHER INFORMATION: synthetic polynucleotide

<400> SEQUENCE: 82
cctgtcacac agtaggacct tcacta          26

<210> SEQ ID NO 83
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 83
tcacaggtta aagggtctca gggact          26

<210> SEQ ID NO 84
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 84
ctacctgcac tgtaagcact tttcta          26

<210> SEQ ID NO 85
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 85
cgccaatatt tacgtgctgc tactag          26

<210> SEQ ID NO 86
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 86
acagagagct tgcccttgta tactag          26

<210> SEQ ID NO 87
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 87
tccatcatca aaacaaatgg agtcta          26

<210> SEQ ID NO 88
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 88
aagaacaatg cctttgtgtg atctag          26

<210> SEQ ID NO 89
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 89
cctggcacac agtatgacct tcacta                                  26

<210> SEQ ID NO 90
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 90
acaatcctag ccttcactag cagcct                                  26

<210> SEQ ID NO 91
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 91
aacactgatt tcaaatggtg ctacta                                  26

<210> SEQ ID NO 92
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 92
aaagagaccg gttcactgtg actagc                                  26

<210> SEQ ID NO 93
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 93
cctccagtct agccacactc tagcag                                  26

<210> SEQ ID NO 94
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 94
cacaagttcg gatctacgtg ttctag                                  26

<210> SEQ ID NO 95
<211> LENGTH: 26
<212> TYPE: DNA
<213> ORGANISM: Artificial sequence
<220> FEATURE:

<223> OTHER INFORMATION: synthetic polynucleotide

<400> SEQUENCE: 95
accgaccgac cgatcgaccg actagc                                              26

<210> SEQ ID NO 96
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 96
tcatcattac caggcagtat tactag                                              26

<210> SEQ ID NO 97
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 97
gagggagggc tgataagcta ctagca                                              26

<210> SEQ ID NO 98
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 98
acgctcaaga tgtgctgcta ctagca                                              26

<210> SEQ ID NO 99
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 99
acaaaagttg cctttgtgtg atctag                                              26

<210> SEQ ID NO 100
<211> LENGTH: 26
<212> TYPE: DNA
<213> ORGANISM: Artificial sequence
<220> FEATURE:
<223> OTHER INFORMATION: synthetic polynucleotide

<400> SEQUENCE: 100
ttcccattcc ctatacctct ctagca                                              26

<210> SEQ ID NO 101
<211> LENGTH: 22
<212> TYPE: RNA
<213> ORGANISM: Artificial sequence
<220> FEATURE:
<223> OTHER INFORMATION: synthetic polynucleotide

<400> SEQUENCE: 101
uggaguguga caaugguguu ug                                                  22

```
<210> SEQ ID NO 102
<211> LENGTH: 65
<212> TYPE: DNA
<213> ORGANISM: Artificial sequence
<220> FEATURE:
<223> OTHER INFORMATION: synthetic polynucleotide

<400> SEQUENCE: 102
cctctctatg ggcagtcggt gacaaacacc attgtcacac tccactgagt cggagacacg    60
caggg                                                                65

<210> SEQ ID NO 103
<211> LENGTH: 22
<212> TYPE: RNA
<213> ORGANISM: Artificial sequence
<220> FEATURE:
<223> OTHER INFORMATION: synthetic polynucleotide

<400> SEQUENCE: 103
uggaguguga caaugguguu ug                                             22

<210> SEQ ID NO 104
<211> LENGTH: 38
<212> TYPE: DNA
<213> ORGANISM: Artificial sequence
<220> FEATURE:
<223> OTHER INFORMATION: synthetic polynucleotide

<400> SEQUENCE: 104
tgtcacactc cactgagtcg gagacacgca gggcttaa                            38

<210> SEQ ID NO 105
<211> LENGTH: 37
<212> TYPE: DNA
<213> ORGANISM: Artificial sequence
<220> FEATURE:
<223> OTHER INFORMATION: synthetic polynucleotide

<400> SEQUENCE: 105
ctcgacctct ctatgggcag tcacgaccaa acaccat                             37

<210> SEQ ID NO 106
<211> LENGTH: 29
<212> TYPE: DNA
<213> ORGANISM: Artificial sequence
<220> FEATURE:
<223> OTHER INFORMATION: synthetic polynucleotide

<400> SEQUENCE: 106
tcacgaccaa acaccattgt cacactcca                                      29

<210> SEQ ID NO 107
<211> LENGTH: 22
<212> TYPE: RNA
<213> ORGANISM: Artificial sequence
<220> FEATURE:
<223> OTHER INFORMATION: synthetic polynucleotide

<400> SEQUENCE: 107
ugagguagua guuuguacag uu                                             22

<210> SEQ ID NO 108
<211> LENGTH: 22
<212> TYPE: DNA
<213> ORGANISM: Artificial sequence
<220> FEATURE:
```

<223> OTHER INFORMATION: synthetic polynucleotide

<400> SEQUENCE: 108
aactgtacaa actactacct ca                                                 22

<210> SEQ ID NO 109
<211> LENGTH: 22
<212> TYPE: RNA
<213> ORGANISM: Artificial sequence
<220> FEATURE:
<223> OTHER INFORMATION: synthetic polynucleotide

<400> SEQUENCE: 109
ugagguagua gguugugugg uu                                                 22

<210> SEQ ID NO 110
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 110
aaccacacaa cctactacct ca                                                 22

<210> SEQ ID NO 111
<211> LENGTH: 22
<212> TYPE: RNA
<213> ORGANISM: Artificial sequence
<220> FEATURE:
<223> OTHER INFORMATION: synthetic polynucleotide

<400> SEQUENCE: 111
ugagguagua gguuguaugg uu                                                 22

<210> SEQ ID NO 112
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 112
aaccatacaa cctactacct ca                                                 22

<210> SEQ ID NO 113
<211> LENGTH: 22
<212> TYPE: RNA
<213> ORGANISM: Artificial sequence
<220> FEATURE:
<223> OTHER INFORMATION: synthetic polynucleotide

<400> SEQUENCE: 113
ugagguagua guuuguacag uu                                                 22

<210> SEQ ID NO 114
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 114
aactgtacaa actactacct ca                                                 22

```
<210> SEQ ID NO 115
<211> LENGTH: 22
<212> TYPE: RNA
<213> ORGANISM: Artificial sequence
<220> FEATURE:
<223> OTHER INFORMATION: synthetic polynucleotide

<400> SEQUENCE: 115
ugagguagua gguugugugg uu                                              22

<210> SEQ ID NO 116
<211> LENGTH: 23
<212> TYPE: DNA
<213> ORGANISM: Artificial sequence
<220> FEATURE:
<223> OTHER INFORMATION: synthetic polynucleotide

<400> SEQUENCE: 116
aaccactaca aactactacc tca                                             23

<210> SEQ ID NO 117
<211> LENGTH: 22
<212> TYPE: RNA
<213> ORGANISM: Artificial sequence
<220> FEATURE:
<223> OTHER INFORMATION: synthetic polynucleotide

<400> SEQUENCE: 117
ugagguagua gguugugugg uu                                              22

<210> SEQ ID NO 118
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 118
aaccacacaa cctactacct ca                                              22
```

LIGASE ACTIVITY

CROSS REFERENCE

This application claims the benefit of U.S. provisional application Ser. Nos. 62/045,214, filed on Sep. 3, 2014, 62/174,257, filed on Jun. 11, 2015, and 62/192,623, filed on Jul. 15, 2015, and is a continuation-in-part of U.S. patent application Ser. No. 13/829,489, filed on Mar. 14, 2013, which application claims the benefit of provisional patent application Ser. No. U.S. 61/745,244, filed on Dec. 21, 2012, all of which applications are incorporated by reference herein.

BACKGROUND

Ligation of single stranded (ss) DNA oligonucleotides splinted by complementary RNA is an essential step in techniques such as RNA-mediated annealing, selection, and ligation (RASL). T4 DNA ligase has been used for RASL as well as for other RNA analysis and detection techniques such as molecular inversion probes, modified ligase chain reactions and ligase detection reactions (for example, Yeakley, et al., *Nat Biotechnol.*, 20(4):353-8 (2002), Bullard and Bowater, *Biochem. J.*, 398(1):135-44 (2006); Li, et al., *Curr Protoc Mol Biol.* April; Chapter 4: Unit 4.13.1-9 (2012); US published application No. 2011/0092375, U.S. Pat. No. 7,361,488; Nilsson, et al., *Nature Biotechnology*, 18:71 (2000); Nilsson, et al., *Science*, 265, 2085-2088 (1994); Barany, *PCR Methods Appl.*, 1:5-16 (1991); Landegren, *Bioessays*, 15:761-765 (1993); Wiedmann, et al., *PCR Methods Appl.*, 3:S51-64 (1994); Nilsson, et al., *Nat Genet.*, 16:252-255 (1997); Baner, et al., *Nucleic Acids Res.*, 26:5073-5078 (1993); Hardenbol, et al., *Nature Biotechnol.*, 21:673-678 (2003); and Landegren, *Methods Cell Biol.*, 75:787-797 (2004)).

T4 DNA ligase works poorly requiring, for example, long incubation times, high concentrations of ligase, and low ATP concentrations to overcome the preferential formation of adenylated DNA side product to accomplish ligation.

T4 RNA ligase was tested as an alternative choice for joining DNA strands hybridized to an RNA template or splint (U.S. Pat. No. 6,368,801). The NAD+ dependent ligase from *Melanoplus sanguinipes* entomopoxvirus was reported to have a ligation activity for DNA hybridized to RNA similar to T4 DNA ligase but only in the presence of $Mn^{2+}$ (Lu, et al., *Biocimica et Biophysica Acta*, 1701:37-48 (2004)). Sriskanda, et al., *Nucleic Acid Research*, 26 (15): 3536-3541 (1998) reported PBCV-1 DNA ligase from *Chlorella* where experimental data showed that this ligase could ligate oligonucleotides on a DNA template or DNA splint but could not ligate oligonucleotides on an RNA template or RNA splint. These results were explained by crystal structure studies where the authors showed that PBCV-1 ligase forced the substrate into an RNA-type A-form helix on one side of a nicked substrate, but required a DNA-type B-form helix on the side of the nick providing the 5'phosphate (Ho, et al., *J. Virol.*, 71(3):1931 (1997); Sriskanda, et al., (1998); Nair, et al., *Nat. Struct. Mol. Biol.*, 14:770-778 (2007)). Similar results were reported in crystal structures of the NAD-dependent *E. coli* DNA ligase (Nandakumar, *Mol. Cell*, 26:257-271 (2007)) and human DNA ligase 1 (Pascal, et al., *Nature*, 432:473-478 (2004)) leading to a conclusion that these ligases could not accept RNA-splinted DNA as ligation substrates.

SUMMARY

In general in one aspect, a composition is provided that includes an RNA splint ligase and at least one polynucleotide having a length of at least 8 nucleotides in a buffer.

Embodiments of the composition may include one or more of the following features: the RNA splint ligase and the at least one polynucleotides are in a molar ratio of greater than 100:1 or less than 100:1, 10:1 or 1:1 of ligase to polynucleotide; the buffer comprises 1 µM-1.5 mM ATP, and/or the RNA splint ligase is PBCV-1 ligase.

In general, in one aspect, a method is provided for ligating single stranded polynucleotide fragments, that includes: combining at least two single stranded polynucleotide fragments having complementary regions at a splice junction to an RNA splint and an RNA splint ligase; and permitting the at least two single stranded polynucleotides to ligate to form a single polynucleotide.

Embodiments of the method may include one or more of the following features: performing the ligation reaction in a buffer containing at least 1 µM-1.5 mM ATP; utilizing an RNA splint having a length greater than 8 nucleotides and a plurality of polynucleotides each having a length of greater than 8 nucleotides incubating the reaction for less than 6 hours to achieve at least 70%-90% ligation of polynucleotides; incubating the reaction for less than 1 hour to achieve at least 70%-90% ligation of polynucleotides; and/or performing the ligation reaction with an enzyme: substrate molar ratio of greater than 100:1 or less than 100:1, 10:1 or 1:1. In certain embodiments, the ligation may occur more rapidly for RNA splint ligase than for a ligation using T4 DNA ligase under similar conditions; the single stranded polynucleotide may be a template for quantitative PCR such that amplifying the ligated single stranded polynucleotide results in less background amplification of non-template polynucleotide than observed when the RNA splint ligase is replaced with T4 DNA ligase and/or the splint ligase is capable of ligating the polynucleotides at a rate that is at least 5 times or 10 times faster than T4 DNA ligase under the same reaction conditions and with the same polynucleotides.

In general, in another aspect, a method is provided for analyzing mRNA for its splicing history, comprising: identifying splice junctions, splicing variants or mutations at the splice junction by combining ssDNA oligonucleotides with the mRNA and an RNA splint ligase.

In general in another aspect, a method is provided for detecting RNA sequences that includes: annealing polynucleotides having regions that are complementary at a ligation junction to a splint RNA; ligating the polynucleotides using an RNA splint ligase, amplifying the ligation product; and detecting and optionally quantifying the amplification product.

Embodiments of the method may include one or more of the following features: the RNA sequence is a microRNA; and/or the RNA splint ligase is PBCV-1 ligase.

In some embodiments, the method may comprise: (a) annealing DNA oligonucleotides to a specific RNA in a mixture of RNAs, wherein the DNA oligonucleotides have regions that are exactly complimentary at a ligation junction to the specific RNA; (b) ligating the DNA oligonucleotides using an RNA splint ligase; and (c) amplifying the ligation product quantitatively to detect the specific RNAs in the mixture of RNAs.

In some embodiments, the specific RNA is an RNA splint for example a microRNA (miRNA); the length of the complementary region on one of the DNA oligonucleotide adjacent to the ligation junction is at least 4 nucleotides;

and/or the complementary region on the DNA oligonucleotide, adjacent to the ligation junction, contains no nucleotide mismatches with the specific RNA. In another aspect, the length of the complementary region is in the range of 4-40 nucleotides. In another aspect, the RNA splint has a length of about 22 nucleotides or is a preselected region of an intact mRNA and/or is derived from viral RNA.

In some embodiments, the ss oligonucleotides each contain a sequence at a non-ligated end that forms an adapter sequence for downstream processing, in one aspect, the mixture of RNAs are derived from a cell lysate. In one aspect, the cell lysate is obtained from a tissue biopsy, a bodily fluid, a cancer cell, a prokaryote, a microbiome, or a virus infected cell.

In some embodiments, the method may comprise analyzing an RNA sample that includes: combining (i) an RNA splint ligase, (ii) at least two single stranded DNA oligonucleotides that are complementary to adjacent sites in a target RNA; ii) an RNA sample that comprises both the target RNA and a variant of the target RNA that has a sequence variation; permitting the at least two single stranded DNA oligonucleotides to ligate to form a ligation product; and detecting the ligation product.

In one embodiment, the variant of the target RNA which may be for example, an mRNA, a miRNA, an exosomal RNA or a viral genome, contains one or more nucleotide substitutions in one or both of the binding sites for the stranded DNA oligonucleotides, for example, the site of the sequence variation is proximal to the ligation junction formed as described above. In one aspect, the detecting is quantitative. Another aspect includes determining the amount of the target RNA relative to the amount of the variant of the target RNA, another aspect includes amplifying the ligation product.

BRIEF DESCRIPTION OF THE FIGURES

FIG. 2(A)-2(D) shows ligation of two DNA oligonucleotides (DNA-DNA ligation) splinted by DNA or RNA. The marked peaks are unreacted pDNA (I) and ligated product (II) as identified by co-elution with authentic standards. 100 nM of standard oligonucleotides were reacted with 100 nM PBCV-1 DNA ligase (2(B) and 2(D)) or 100 nM T4 DNA ligase (2(A) and 2(C)) for 30 minutes at 20° C. Panel 2(A) and 2(B): Two DNA oligonucleotides were hybridized to a DNA 2(A) and 2(B) where the peak corresponds to complete ligation. Panel 2(C) and 2(D): Two DNA oligonucleotides were hybridized to an RNA reverse complement. A peak corresponding to complete ligation was seen only from the reaction using PBCV-1 ligase 2(D) while no ligation was seen using T4 DNA ligase 2(C).

FIG. 7(A): 2.5 nM luciferase mRNA splint. FIG. 7(B): 25 nM luciferase mRNA splint. PBCV-1 ligase gave a positive signal at a faster rate than T4 DNA ligase in the presence of RNA substrate as shown by the lower Cq values. Additionally, the background response was significantly delayed with the PBCV-1 ligase as compared with T4 DNA ligase as shown by the higher Cq values when no template RNA was provided.

FIG. 8(A)-8(C): Synthesis of long ssDNA by RNA-mediated splint ligation using PBCV-1 ligase. A ssDNA of 121 nt was efficiently assembled using two small pieces of ssDNA with a ssRNA splint. The RNA splint was then removed with RNase H, and the ssDNA purified with HPLC. Ligation reactions were performed containing 0.25 µM annealed oligonucleotides and 1.45 µM PBCV-1 ligase in a ligase reaction buffer (66 mM Tris-HCl, 10 mM $MgCl_2$, 1 mM ATP, 1 mM DTT, 7.5% PEG 6000), pH 7.6 at 25° C. Reactions were incubated at 25° C. for 30 minutes (Panel 8(B)) or 16° C. overnight (Panel 8(C)). A no-enzyme control was shown in Panel 8A. When compared to the standard chemical synthesis method, synthesis of long ssDNA by splint ligation enzymatically has the advantage of high purity, simplified purification, and substantial decrease in cost. These results contrast with current phosphoramidite technology with 99.5% coupling efficiency where a crude solution of synthesized 150-mers would contain 47% full-length product and 53% failure sequences.

FIG. 9 shows the amino acid sequence for *Chlorella* virus polynucleotide ligase (PBCV-1 ligase) and a standard ss oligonucleotide substrate used in the examples.

FIGS. 13A-13D: FIGS. 13A and 13B shows a FAM labeled DNA oligonucleotide to demonstrate ligation by means of capillary electrophoresis and the significantly improved kinetics of the splint ligase compared to T4 DNA ligase or T4 RNA ligase 2. FIG. 13A, is a schematic diagram showing the substrate used for ligation of two DNA oligonucleotides complementary to a miRNA splint. The 5' DNA oligonucleotide, probe A, has a 5' FAM label that allowed detection of the ligated product by capillary electrophoresis. Probe B oligonucleotide requires a 5' phosphate for ligation. The miRNA splint, miR-122, is shown in the figure. FIG. 13B shows the results of a time course for ligation using PBCV-1 ligase, T4 RNA ligase 2 and T4 DNA ligase. The concentration of the enzymes used was 1 µM and the DNA oligonucleotide concentration was 25 µM. The temperature of the reaction was consistent with the enzyme reaction optimum −16° C. for PBCV-1 and 37° C. for the T4 ligases. The results shows as much as 100 fold increase in ligation efficiency at any time point between 0 and 120 minutes using the PBCV-1 ligase compared to T4 DNA ligase or T4 RNA ligase 2. FIG. 13C shows a table containing multiplex detection of miRNAs using 49 pairs of DNA oligos. 49 pairs of miRNA-specific DNA oligos were hybridized to a library of 960 synthetic miRNAs (Miltenyi Biotec), ligated by SplintR ligase and then amplified using Illumina specific primers. A thousand fold weight excess of yeast RNA was added to the ligation to mimic a biological sample. The forty most abundant MiSeq reads are shown in column A, sequences in column B and the miRNA identity in column C. Over 80% of the reads are the correct ligation products. FIG. 13D shows a cartoon of the oligonucleotide reaction. FIG. 13C, from top to bottom: SEQ ID NOS: 61-100.

FIGS. 14A and 14B shows a comparison of the activity of PBVC-1 ligase, T4 DNA ligase and T4 RNA ligase 2 for joining DNA oligonucleotides with different amounts of overlapping sequence with the RNA splint (miRNA splint). FIG. 14A shows the 10 different oligonucleotides tested in black with the matching oligonucleotide for ligation in grey. A series of ten pairs of DNA oligonucleotides complementary to miR-122 were synthesized with varying degrees of overlap with the RNA splint where an miRNA is exemplified to determine the overlap required for ligation. The shortest overlap tested was 2 nucleotides. The probes scan the miRNA sequence in two nucleotide increments. Probe A has a 5' FAM label, shown in grey, and probe B, shown in black, has a 5' phosphate to allow ligation. The combined length of each ligated pair of oligonucleotides is 65 nucleotides. The activity of three different ligases, PBCV-1 ligase, T4 DNA ligase and T4 RNA ligase 2 were determined for the 10 different DNA oligonucleotides. FIG. 14B shows that the splint mediated ligation products were separated from the unligated FAM labeled probe A, by polyacrylamide gel electrophoresis (PAGE). Because there is excess of probe A compared to the miRNA splint, un-ligated probe was observed in all lanes. The results show the presence of ligated DNA from a 22 nucleotide overlap down to a 4 nucleotide overlap using PBCV-1 ligase with the large fragments represented by the slower running band corresponding to ligated DNA. In contrast, very faint bands of ligation product were seen for T4 RNA ligase 2 in a sample with a 18 nucleotide overlap and no ligation products were detected for T4 DNA ligase under the same experimental conditions used for PBCV-1 ligase. FIG. 14A, top is SEQ ID NO:101, bottom sequences are all SEQ ID NO:102.

FIG. 15A—DNA-DNA: ligation splinted by mRNA. The reduction in number of cycles to detect ligated product using a splint ligase compared with T4 DNA ligase was at least 35 cycles reduced to 25 cycles which corresponds to at least 100 fold increased efficiency at the same time points. FIG. 15B—DNA-DNA: ligation splinted by mRNA is plotted over a range of mRNA concentrations. The concentration was determined by qPCR. At every concentration examined, the splint ligase significantly outperformed T4 DNA ligase as determined by number of cycles and copy number both plotted on a log scale.

FIG. 16A shows a schematic of how miR-122 was detected in in rat liver RNA by SplintR ligation and PCR amplification. The miR-122 sequence has a ten base overlap with probe A and 12 base overlap with probe B. The second strand cDNA is synthesized by DNA polymerase and is complementary to the miR-122 specific probe. The positions of the two quenchers, Q and Z, and the fluorescein dye, F, are marked on the probe. During PCR amplification the Taq polymerase degrades the probe and releases the unquenched dye. FIG. 16C shows the detection of miR-122 in rat liver RNA by SplintR ligation and PCR amplification the number of cycles of amplification required to detect the ligation product of miRNA in the context of rat liver total RNA. The amounts are given in pictograms of total RNA. miRNA is no more than 0.05% of the total RNA. 1000 pg of total RNA provide a detectable signal after 20 cycles of amplification. FIG. 16B shows standard curves were generated with a fourfold serial dilution of miR-122 RNA oligo, from 125 to 0.03 attomole. Three qPCR assays were performed at each concentration. To mimic biological samples, yeast RNA was added to the assay. Details of the ligation and amplification are described in Materials and Methods.

FIGS. 16B and 16C additionally show graphs of the Cq value vs. the log of the miRNA concentration or amount of rat liver RNA. In both cases the graphs show linearity of the assay. FIG. 16A, from top to bottom, SEQ ID NOS: 103-106.

FIG. 17A-17E show that single base differences between an oligonucleotide and the splint can result in a failure of splint ligation. FIGS. 17A and 17B show the sequences of the eight of the let-7 family are shown. The arrow indicates the let-7g isoform. The underlined sequence show the six nucleotides that are complementary to the let-7g specific probe A. FIG. 17C shows the specificity of let-7g DNA probes. The let-7g probes were hybridized to all members of the let-7 family, ligated with SplintR ligase for one hour at 16 degrees C. and analyzed on a non-denaturing acrylamide gel. The controls are no probe A [no A] and no probe B [no B]. The ligation product is specific for the let-7g miRNA. FIG. 17D. Specific detection of let-7b, let-7c and let-7g isoforms by SplintR ligation. The aligned sequences of eight members of the let-7 family are shown at the left. One block of sequences is shown for each isoform: let-7b, let-7c and let-7g. The sequence of the specific let-7 isoform is underlined. Nucleotides that do not match that isoform are shown in bold font. A vertical black line marks the ligation junction for the two probes. FIG. 17A, from top to bottom, SEQ ID NOS: 50-57. FIG. 17B, from top to bottom, SEQ ID NOS: 107-108. FIG. 17D, from top to bottom, SEQ ID NOS: 50-57.

FIG. 17E Gel analysis of ligation reactions. Each specific set of DNA probes was individually hybridized to all eight let-7 miRNAs and ligated by SplintR as described. The stacking DNA oligonucleotide, which is complementary to probe A, was included to enhance the annealing and ligation reactions for let-7b and let-7c. After separation on polyacrylamide gel the FAM labeled probe A was visualized using a UV light. Negative controls include: no probe A (−A), no SplintR Ligase (−R), no stacking oligo (−S) and no probe B (−B). The oligonucleotides used in each ligation are shown above the gel. The miRNA sequence is shown above the DNA probes. A vertical line denotes the ligation junction. Hybridization of the stacking oligo to probe AS and A4 results in retarded mobility on the gel. A single band, probe A, is observed in the absence of the stacking oligo (−S). FIG. 17E, from top to bottom, SEQ ID NOS: 109-114.

FIGS. 18A and 18B show similar results for Let-7 (b) at 16° C. and 20° C. showing that the specificity and sensitivity of the ligase for ligating sequences of DNA that hybridize exactly to RNA splint is consistent even at variable temperatures. All reactions were done in triplicate. The ligation reaction was incubated for 100 minutes. For the PCR cycle conditions, initial denaturation was 95° C. for 3 minutes, then 10 seconds at 95° C. and 30 seconds at 55° C. The average Cq for each miRNA splint is compared to Let-7 (b) and the fold difference is expressed as a percentage of Let-7 (b). FIG. 18A shows a 22 nucleotide Let-7 (b) oligonucleotides which has a sequence that is exactly complementary to Let-7 (b) but varied by 1-4 nucleotides for each of 7 similar RNA splints. The numbers on the left of the sequences show the results of quantitative PCR where Let-7 (b) gave 100% yield but the other Let-7 oligonucleotides gave no more than 2% yield relative to Let-7 (b). FIG. 18B shows a gel of the splint mediated ligation reactions using the 22 nucleotide Let-7 (b) oligonucleotide ligated to a second oligonucleotide with exact sequence complementarity. The gel shows that only the oligonucleotide with exact sequence complementarity became ligated thus demonstrating that the splint ligase showed a high degree of specificity. FIG. 18A, from top to bottom, SEQ ID NOS: 50-57. FIG. 18B, from top to bottom, SEQ ID NOS: 115-116.

FIG. 20A, from top to bottom, SEQ ID NOS: 117-118.

DETAILED DESCRIPTION

Figure 1:
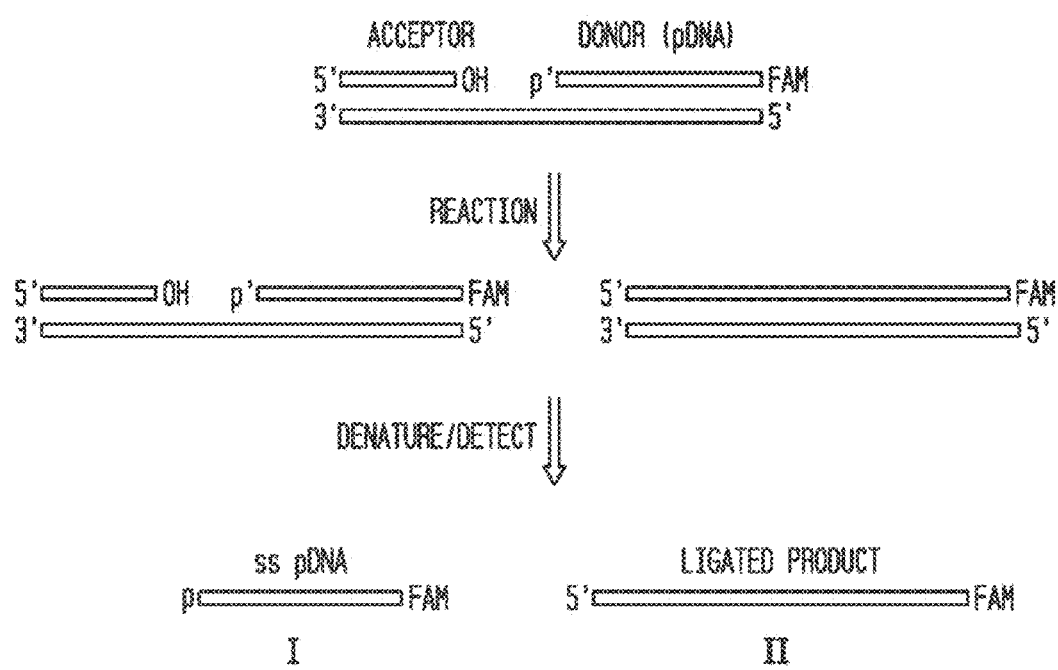
FIG. 1 outlines an assay for ligation of DNA splinted by a DNA or RNA templates. Pre-anealed nicked substrates, such as a 20 deoxynucleotide acceptor DNA, a 30 deoxynucleotide, FAM-tagged and 5'-phosphorylated donor DNA, and either a DNA or an RNA reverse complement (splint), is incubated with a suitable ligase, then quenched with 100 mM EDTA and denatured with formamide. Fragments can be separated and the FAM labeled ssDNA ligation product detected by capillary electrophoresis.

A ligase is described herein that surprisingly ligates ssDNA oligonucleotides splinted by a ssRNA with high efficiency. This ligation efficacy substantially improves the utility of techniques that preferably utilize RNA splinting with two or more oligonucleotides in methods such as RASL and RASL-seq as well as methods that enhance the utility of molecular inversion probes and modified ligase chain reaction/ligase detection reaction for RNA analysis and detection.

The term "RNA splint ligase" unless specified otherwise refers to an enzyme that is capable of ligating at least two ssDNA polynucleotides splinted by a complementary ssRNA polynucleotide and is capable of achieving ligation in less than 6 hours at molar concentrations of enzyme that are not absolutely required to be in molar excess compared to substrate. For very low concentrations of substrate, the enzyme may be in excess for convenience. Examples of RNA splint ligases are DNA ligases that are naturally occurring or closely related variants having at least 90%, 95%, 98% or 99% amino acid sequence identity to the wild type ligase where the ligase may be derived from algal viruses such as the *Chlorella* virus, for example, PBCV-1 ligase (SEQ ID NO:1), or may be identified by Blast search of the GenBank or NCBI or other database using for example, the basic local alignment search tool found on blast.ncbi.nlm.nih.gov/Blast.cgi using the query id gi|9632109|ref|NP_048900.1. as of Mar. 14, 2013 and variants and mutants thereof. The RNA splint ligase includes protein fusions including purification tags (e.g. HisTag, chitin binding domain (CBD), maltose binding protein (MBP), biotin) or DNA binding domain fusions (e.g. sso7d, or alkyl guanine transferase (AGT)).

The RNA splint ligase, single stranded polynucleotide and/or splint RNA may be immobilized on a matrix such as a reaction surface, or a magnetic bead to facilitate automated protocols and multiplexing reactions.

Contrary to the publication describing PBCV-1 ligase as inactive in ligating DNA oligonucleotides together on an RNA splint (Sriskanda, et al., (1998)), it has here been shown here that ssDNA oligonucleotides of a size greater than 8 nucleotides can surprisingly be ligated together to form a single oligonucleotide of at least 16 nucleotides when splinted by a complementary RNA with an efficiency that is greater than 10 fold to 1000 fold over T4 DNA ligase.

The term "RNA splint" includes a ssRNA having a size greater than 8 nucleotides or 10 nucleotides for example, greater than 12 or 15 or 18 or 20 or 22 or 24 or 26 or 28 or 100 nucleotides or a size as large as an RNA virus genome that is capable of hybridizing at least in part to at least two, three or more single stranded polynucleotides for example having a size of at least 8 or 10 or 12 or 14 or 16 or 20 nucleotides or greater in length so as to enable the ligation of the fragments to each other by means of an RNA splint ligase.

The RNA splint may be entirely complementary to the hybridizing polynucleotide, or may extend longer than the complementary region on the hybridizing polynucleotide, for example the splint may be 2, 4, 6, 8, 10 or more nucleotides longer than the hybridizing polynucleotide. The splint may be a portion of a much larger RNA structure for example an mRNA, tRNA, other cellular RNA, or RNA viral genome, such that a region of the RNA is complementary to the hybridizing polynucleotide but the majority of the structure has no complementarity to the hybridizing polynucleotide.

The RNA splint can come from any source. For example, splint RNA can be prepared by chemical synthesis or obtained from mRNA samples, total RNA, microRNAs, long noncoding RNAs or other naturally occurring RNAs, nucleic acid libraries, cells, cultures, tissues, pathogens, bodily fluids, urine, serum, biopsy samples, and environmental samples. Any other source of RNA that is known or can be developed can be used with the disclosed method.

The term "polynucleotide" includes DNA, RNA or part DNA and part RNA. The polynucleotides when used in a ligation reaction with an RNA splint are preferably single stranded and may be partially or wholly complementary to at least a portion of the RNA splint. An example of a polynucleotide described herein is a ssDNA oligonucleotide comprising at least 8 nucleotides.

The term "single stranded DNA oligonucleotide" (ss DNA) refers to a probe that may be naturally occurring or synthetic. In one embodiment, the ss DNA oligonucleotide has a known sequence and has been synthesized by means of chemical synthesis. Depending on cost of the synthesis procedure, it may be preferable to design a probe of a length that is less than 100 nucleotides. The probe may contain 4 or more nucleotides that are exactly complementary to an RNA splint sequence or to a specific RNA sequence. The probe may also contain defined sequences at an end that is opposite to the ligation junction. These defined sequences may be used in downstream processing such as for an adaptor for primer dependent amplification; as a marker; and/or as a sequence tag for molecule enrichment either before or after splint ligation.

The ss DNA oligonucleotide may have an unknown sequence and may be derived from a virus, a prokaryotic or a eukaryotic cell or from any other natural source such as a bodily fluid, or environmental source. By using an RNA splint of known sequence, one or more ss DNA oligonucleotides may be identified. If the DNA oligonucleotide or oligonucleotides are naturally occurring or are a product of cloning, there is no particular limit on size for use in RNA splint mediated ligation.

Where the probe sequence is known, the RNA splint may have an unknown sequence. The ss DNA oligonucleotides of known sequence may be used to identify the RNA following ligation by means of the RNA splint ligase. The sequences of several RNA splint ligases that may be used in the present method are set forth in the following Genbank accessions: NP_048900.1, 1P8L_A, 2Q2T_A, AGE48553.1, 1FVI_A, AGE57431.1, AGE54684.1, AGE51623.1, YP_001498739.1, AGE55055.1, AGE54372.1, YP_001497930.1, AGE59692.1, AGE55911.1, AGE49090.1, AGE49418.1, AGE56564.1, AGE50110.1, AGE60028.1, AGE59352.1, AGE53463.1, AGE56452.1, YP_001426668.1 and AGE55586.1, which Genbank entries are incorporated herein in their entireties. The RNA splint ligase may be a protein fusion where the enzyme of portion thereof is fused to a second protein such as a purification tag (e.g. HisTag, chitin binding domain (CBD), maltose binding protein (MBP), biotin) or a DNA binding domain fusions (e.g. sso7d, or alkyl guanine transferase (AGT)). The RNA splint ligase may be at least 5 fold, 10 fold, 20 fold, 30 fold, 40 fold, 50 fold 60 fold, 70 fold, 80 fold, 90 fold, or as much as 100 fold, 200 fold, 300 fold, 400 fold, 500 fold, 600 fold, 700 fold, 800 fold, 900 fold or 1000 fold or 2000 fold, 3000 fold, 4000 fold, 5000 fold or more efficient at ligating oligonucleotide substrate on an RNA splint than T4 DNA polymerase under the same reaction conditions using the same substrate. In one example, splint ligases (such as *chlorella* virus splint ligase had a faster maximum turnover rate (>20x) and a much lower Km (1 nM vs 300 nM for T4) for the RNA:DNA substrates than did T4DNA ligase. The T4 DNA ligase has a Km of about 300 nM compared to 1 nM for the splint ligase.

In some embodiments the "RNA splint" includes a ssRNA or a denatured double stranded RNA which may be derived from a viral RNA which may be a positive or negative sense single strand RNA or double strand. The RNA splint may be a naturally occurring RNA found in a virus, a prokaryotic or a eukaryotic cell or from any other natural source such as a bodily fluid, or environmental source. Examples of RNA splints include RNAs from human disease viruses such as polio virus, picorna virus, influenza virus, Ebola virus, hepatitis C, West Nile fever, rhinovirus and measles, and RNA viruses of agricultural significance such as tobacco mosaic virus. RNA viruses have a high rate of mutation and therefore the high degree of specificity and sensitivity demonstrated herein (see for example, FIGS. 17A-17E and 18A-18B) is particularly useful for identifying variants without the added complication of mutations resulting from reverse transcriptase activity. The advantageous properties of embodiments also may be used to classify variants of retroviruses that are associated with cancer. Another class of RNA splints are microRNAs (miRNAs) which play a role in transcriptional regulation and are also implicated in cancer. The examples shown herein demonstrate that embodiments are similarly effective for miRNAs as for mRNAs. Another class of RNA splints are small RNA molecules contained in exosomes that are also implicated in chronic diseases such as cancer.

The term "polymorphism" as used herein refers to a nucleotide variation in an RNA, e.g., a miRNA, that differs from a related RNA by a single nucleotide, or two or more nucleotides. The variation may a single nucleotide, or two or more nucleotides, up to the entire sequence recognized by the sequence-specific single strand DNA probes used in the ligation reaction. The variation may be proximal to, e.g., within 5 or 6 bases of, or at the ligation junction.

It must be noted that as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation. As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

The present teachings encompass various alternatives, modifications, and equivalents, as will be appreciated by those of skill in the art. Where a range of values is provided, it is understood that each intervening value, to the tenth of the unit of the lower limit unless the context clearly dictates otherwise, between the upper and lower limit of that range and any other stated or intervening value in that stated range is encompassed within the present disclosure.

Where the hybridizing polynucleotide has complementary regions to the RNA splint, this may be limited to the ligation junction with non-complementary regions elsewhere. Examples include primer binding regions for PCR amplification, self-complementary regions for reverse molecular beacon design, non-complementary linker regions, or non-complementary regions extending beyond the length of the RNA splint. The hybridizing polynucleotide may be linked together by a long non-complementary region such as for molecular inversion probes for rolling circle amplification (RCA), such that they are a single polynucleotide with two distinct hybridization regions. The polynucleotide may hybridize such that they are fully base paired to the splint at the ligation site with no gaps, or they may hybridize with a gap of for example 4, 6, 8, 10, or more nucleotides apart on the RNA splint such that ligation produces ssRNA loop-out region in the splint RNA.

One or more of the ss polynucleotides for hybridizing to the RNA splint, and/or RNA and/or RNA splint ligase may be coupled to a substrate for example, a matrix such as for example, a magnetic bead, a glass or silica substrate or a surface in a microfluidic device or other reaction chamber. Additional solid-state substrates to which oligonucleotides can be coupled, directly or indirectly include acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, fibers, woven fibers, shaped polymers, particles and microparticles (Pease, et al., *Proc. Natl. Acad. Sci. USA*, 91(11):5022-5026 (1994); Khrapko, et al., *Mol Biol (Mosk) (USSR)* 25:718-730 (1991); Stimpson, et al., *Proc. Natl. Acad. Sci. USA*, 92:6379-6383 (1995); Guo, et al., *Nucleic Acids Res.* 22:5456-5465 (1994); U.S. Pat. Nos. 5,871,928; 554,413; 5,429,807; 5,599,695; and 6,368,801)).

Coupling of polynucleotides to substrates may facilitate the handling of multiple samples singly or in multiplex reactions and in automation of the reaction. Suitable labels and capture tags used to identify products of ligation are known in the art and described in U.S. Pat. No. 6,368,801.

Features of ligating polynucleotides on an RNA splint may include one or more of the following:

Temperature range: Ligation may be achieved at a temperature in the range of 4° C. to 50° C. for example, 16° C., 25° C., and 37° C.

Figure 3A:
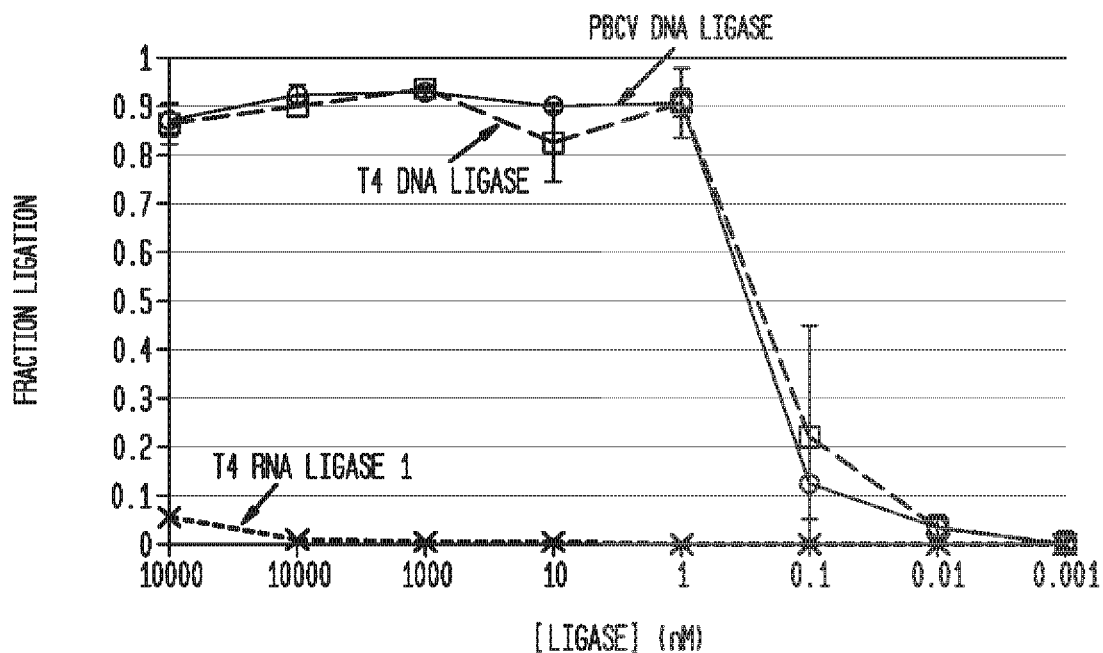
FIG. 3(A)-3(B) shows ligation of 100 nM pre-annealed standard oligonucleotide substrates splinted by DNA using T4 DNA ligase, T4 RNA ligase 1 or PBCV ligase, at a range of concentrations (1 µM-10 µM) at 20° C. in standard ligation buffer containing 1 mM ATP. 3(A) DNA-DNA: ligation splinted by DNA. 3(B) DNA-DNA: ligation splinted by RNA reverse complements. Both PBCV-1 DNA ligase and T4 DNA ligase could ligate DNA oligonucleotides splinted by DNA with similar ligation activity but only PBCV-1 ligase could form detectable amounts of ligation product for oligonucleotide substrates splinted by RNA reverse complements. T4 RNA Ligase 1 had slight activity on DNA splinted ligation and no detectable activity on RNA splinted ligations.
Figure 3B:
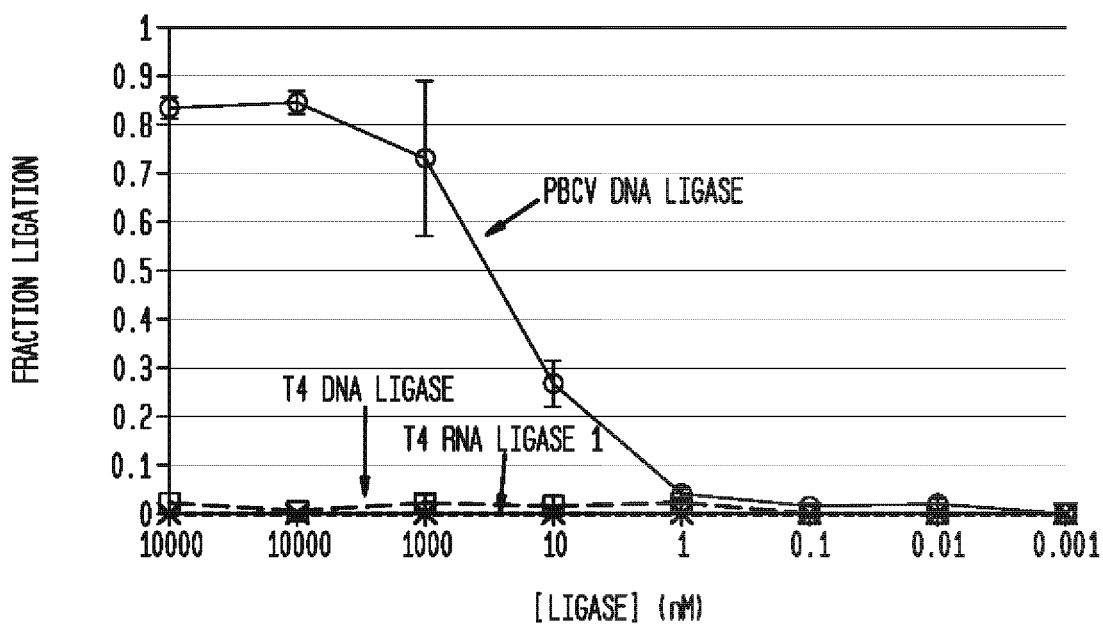

Enzyme concentrations: Ligation may be achieved at a concentration in the range of, for example, 1 nM-1 mM enzyme. Relatively small amounts of RNA splint ligase may be used to ligate ssDNA on an RNA splint with at least 70%, 80%, or 90% efficiency. Examples of substrate to enzyme ratios, include a range of 1:10 to 10:1 or 100:1 to 1:100 or 1:1000 to 1000:1 or 1:10,000 to 10,000:1 with completion of ligation within 6 hours, for example within 5 hours, 4 hours, 3 hours, 2 hours or 1 hour. Completion of ligation can be determined by PCR gel or capillary electrophoresis. T4 DNA ligase requires 10:1 to 100:1 of enzyme to substrate to obtain a reaction product and can take in excess of 12 hours to perform a ligation that may be incomplete. An example of the dramatic difference in activity between an RNA splint ligase and T4 DNA ligase and T4 RNA ligase is shown in FIG. 3(A)-3(B).

ATP concentrations: Ligation may be achieved in the presence of ATP in a range of less than 1.5 mM ATP for example, 1 µM-1 mM ATP, for example, 1 mM, 0.9 mM, 0.8 mM, 0.7 mM, 0.6 mM, 0.5 mM, 0.4 mM, 0.3 mM, 0.2 mM, 0.1 mM, 90 µM, 80 µM, 70 µM, 60 µM, 50 µM, 40 µM, 30 µM, 20 µM, 10 µM, or 1 µM. The use of ATP in the higher end of the range provided here may be preferred because if some hydrolysis of ATP occurs during storage or under reaction conditions, the buffer remains effective at stabilizing the RNA splint ligase reaction. Furthermore, reactions can be performed in the absence of ATP, if the RNA splint ligase exists in an adenylated form.

Reaction time: Ligation may be achieved in less than 12 hours. The reaction may be incubated for 5 minutes-60 minutes to achieve effective ligation or for longer periods of time as described above.

pH: Ligation may be achieved at a pH in the range of pH 6-pH 9, showing ligation rates for RNA splint ligases at least 10× faster than T4 DNA ligase within that range.

Ratio of reaction rates between T4 DNA ligase and an RNA splint ligase at high and low concentrations of ATP: In embodiments of the method, the rate of ligation at high ATP concentrations was consistently as much as 100:1 greater for an RNA splint ligase (PBCV-1 ligase) then for T4 DNA ligase or T4 RNA ligase regardless of substrate sequence. At low concentrations of ATP, under conditions optimized for T4 DNA ligase, the RNA splint ligase has at least fivefold or tenfold (10:1) greater activity than T4 DNA ligase.

Consistent improvement in ligation using RNA splint ligases compared with T4 DNA ligase with all substrates tested: The improved ligation as described above was independent of substrate sequence. This is in contrast with ligation reactions using T4 DNA ligase that was substrate sensitive. For example, T4 DNA ligase was able to ligate two oligonucleotides (SEQ ID NO:2 and SEQ ID NO:3) using an RNA splint (SEQ ID NO:4) in optimal conditions of low ATP albeit slowly whereas when the first nucleotide was changed from T to G in SEQ ID NO:3, the T4 DNA ligase in the same reaction conditions showed no detectable ligase activity. In contrast, the RNA splint ligase was able to ligate this altered substrate efficiently as well as the unaltered substrate.

Indeed, the rate of reaction difference between the best substrate and the worst substrate tested using T4 DNA ligase was greater than 1000 fold even using reported low concentrations of ATP for T4 DNA ligase (10 µM ATP versus 1 mM ATP).

Using the present embodiments with RNA splint ligase, the reaction difference between the same best substrate and the same worst substrate tested (as for T4 DNA ligase) using RNA splint ligase was less than 50 fold, for example (less than 40 fold, 30 fold or 20 fold) under the same reaction conditions as used for T4 DNA ligase.

The above-described characteristics of the RNA splint ligase for efficient ligation reactions between single stranded polynucleotides that are splinted by RNA can be used to enhance methods of RASL, RASL-seq, and Molecular Inversion Probes (also known as padlock probes). Other uses may include using RNA splints to help build-up long ssDNA through ligation of short fragments followed by RNase treatment (for example, using RNase H or mutants thereof) to remove the RNA splints (see FIG. 8(A)-8(B)) and detection of microRNAs (see FIGS. 10 and 11).

Quantitative mRNA profiling through RASL is generally accomplished through ligation of two ssDNA oligonucleotides (DNA probes) complementary to an RNA of interest. In standard RASL, cellular mRNA is isolated and treated with defined DNA probes that will anneal in the presence of the target mRNA sequence to form adjacent 5' and 3' DNA termini. The correctly annealed structure without gaps or mis-pairs can be ligated by the splint RNA ligase to form a ligated probe. The probes also contain qPCR primer regions adjacent to the RNA complementary region, such that when the two probes are ligated the product may be amplified, detected and quantified through qPCR. The degree of qPCR signal can be related to the quantity of the target RNA sequence in the original sample. Due to the strong preference of splint RNA ligase for correctly base paired sequences and sequences lacking gaps, splicing variants and single base polymorphisms in the target mRNA can be detected (Yeakley, et al., (2002)).

RASL-seq is a variant of RASL where detection is accomplished through total DNA sequencing. In RASL-seq the qPCR primer regions are replaced with PCR sequences suitable for amplification and sequencing by any high throughput DNA sequencing methodology. Hundreds of probe sets can be run in parallel with RASL-seq and thus expression levels of hundreds of genes can be simultaneously quantified (Li, et al., (2012)).

Through suitable design of probe sequence outside the mRNA complementary region, detection may be performed through other methods. One example is loop-mediated isothermal amplification (LAMP), wherein probes are designed to form LAMP target structures upon ligation (Notomi, et al., Nucleic Acids Res., 28(12):e63 (2000)). Presence of target RNA is then detected via LAMP amplification, enabling advantages such as isothermal reaction conditions, rapid detection, and implementation in field or point-of-care diagnostics. Upon successful ligation, detection of amplification of target nucleic acid via may be performed with traditional qPCR dyes and probes as described above, or with additional methodologies: turbidity detection of precipitated magnesium pyrophosphate (Mori, et. al., Biochem. Biophys. Res. Commun., 289:150-154 (2001)); colorimetric detection using metal-sensitive indicators (Tomita, et. al., Nat. Protocols, 3(5):877-82 (2008); Goto, et al., BioTechniques, 46(3):167-71 (2009)); bioluminescence through pyrophosphate conversion (Gandelman, et al., PLoS One, 5:e14155 (2010)); or detection via change in pH due to amplification in weakly-buffered conditions (Pourmand, et. al., PNAS, 103(17):6466-70 (2006); U.S. Pat. No. 7,888, 015; and U.S. patent application Ser. No. 13/799,995.

Molecular inversion probes use a single linear strand of DNA as the probe. Use of molecular inversion probes involves a DNA probe designed to have a complementary region to the RNA target sequence such that the 5' and 3' ends of the DNA anneal to bring the termini adjacent, forming a DNA/RNA hybrid helix connected by a loop of ssDNA. Ligation of the DNA termini in the presence of RNA complement by the RNA splint ligase forms a small circular DNA substrate for detection by, for example, RCA. Circularized DNA can be detected by either addition of RCA primers and amplification, or by removing the ssRNA through RNAse treatment leaving the RNA/DNA hybrid region to act as a primer for RCA. RCA products can then be detected by turbidity, pH change, or readout of the DNA product via gel (Li, et al., Anal. Chem., 81 (12):4906-4913 (2009); Absalan and Ronaghi, Methods in Molecular Biology, 396:315-330 (2007); Hardenbol, et al., (2003)).

Other examples of reactions that rely on RNA splinting which currently use T4 DNA ligase have been described in U.S. Pat. No. 6,368,801. These methods can be improved by replacing this enzyme with an RNA splint ligase include ligase chain reaction, ligation followed by PCR; the use of Padlock probes, and the use of FRET-detected molecular beacons generated by ligation (Peng, et al., Anal Chem., 82(23):9727-35 (2010)).

A common RNA detection method uses reverse transcriptase to synthesize a single stranded cDNA copy of RNA. The cDNA can be amplified by PCR using a heat stable DNA polymerase. The efficiency of cDNA synthesis depends upon the secondary structure of the RNA and the DNA primers used for synthesis. DNA ligases that are able to ligate contiguous DNA in a DNA: RNA hybrid are an attractive alternative to cDNA synthesis. The RNA acts as a splint to join the two DNA probes to allow ligation. In order for this detection method to be sensitive, the ligase needs to very efficiently ligate DNA in an RNA hybrid. For the detection of miRNAs an additional property is for the ligase to join DNA oligonucleotides where one DNA probe has only a short 4 to 6 by complementary sequence with an RNA target. The PBCV ligase has these characteristics. It is over 100× faster than either T4 DNA ligase or T4 RNA ligase 2 for RNA splinted DNA ligation. The PBCV ligase is also capable of ligating short (eg 4-6 nucleotides) regions of single strand DNA that are complementary to the RNA target for ligation.

Some embodiments of the method described herein may have several advantages for RNA splint mediated ligation.

For example, the greatly enhanced rate of splint mediated ligation gives the method greater sensitivity—it is possible to detect very low levels of target RNAs in a background of excess non target RNAs in a biological or other sample at concentrations as low as, for example, less than 50 attomoles, for example less than 40 attomoles, 35 attomoles, 30 attomoles, 20 attomoles, 10 attomoles, 1 attomole, 0.1 attomoles or 0.05 attomoles of target RNA in 40 cycles, 35 cycles, 30, cycles, 25 cycles or 20 cycles of amplification. This permits use in a wide range of detection methods (see for example FIG. 16B or FIG. 16C).

Another potential advantage of such embodiments may be the rapid rate of reaction using an RNA splint ligase such as PBCV-1. Detectable quantitative results can be readily detected by electrophoresis or using fluorescence in less than 4 hours, preferably less than 3 hours, preferably less than 2 hours, preferably less than 1 hour for the low concentrations of target RNA described above in a background of not-target RNAs at a convenient temperature such as a temperature preferably below 60° C., preferably below 45° C. for example 16° C., 25° C. or 37° C.

Another potential advantage of some embodiments is the discriminatory properties of RNA splint mediated ligation. As shown in the experimental section of this disclosure, the RNA splint ligase can discriminate between as few as 1 or more, or 2, 3, or 4 or more mismatches in a 22 nucleotide complementary region of an oligonucleotide with respect to the RNA splint.

Another potential advantage is that of specificity of the RNA splint ligation reaction. An RNA splint ligase can ligate two DNA oligonucleotides using an RNA splint with only a 4 to 6 base overlap of one of the DNA oligos with the RNA splint. The combination of the short overlap and discriminatory properties of the RNA splint ligase (for example a 50-100× preference for completely matched RNA:DNA duplex over a single base mismatch) provides a sensitive assay for detecting single base mismatches. In one embodiment, the mismatch may either be at the ligation junction or one base removed from the ligation junction. Assays that rely on designing oligonucleotides having mismatches provide more flexibility for point mutation detection than cDNA primer based approaches. The ligation junction can detect mismatches at either side of the ligation junction while DNA primer based synthesis is only sensitive to mismatches of the primer to the template. The length of the overlap does not determine the overall size of either RNA splint or DNA oligonucleotides. In either case, these molecules may extend beyond the hybridized sequences at the ends by no additional nucleotides or by many nucleotides with the limitations of cost being more significant than efficacy.

Another advantage is multiplexing RNA splint mediated ligation for high through-put analysis. For example, in an embodiment, high through-put analysis utilizes oligonucleotides having a length of 4 to 30 nucleotides or more that are complementary to a target RNA. 4 to 22 complementary nucleotides may be preferred. In addition, pairs of DNA probes may all have conserved terminal sequences that allow them to be amplified by the same set of PCR primers. The oligonucleotides together with RNA and enzymes are combined in a multiplex reaction. 1000 RNA sequences can for example be tested using for example 50 different DNA probes complementary to 50 miRNAs in a single tube and then sequence the amplified product. The identity of the products can then be determined by DNA sequencing. The reduced cost of sequencing allows this approach to be used for surveys of known miRNA sequences.

In certain embodiments, the method may be used for analyzing an RNA sample that contains a target RNA and one or more variants of the target RNA. These embodiments may involve (a) combining: (i) an RNA splint ligase, (ii) at least two single stranded DNA oligonucleotides that are complementary to adjacent sites in a target RNA; ii) an RNA sample that comprises both the target RNA and a variant of the target RNA that has a sequence variation; (b) permitting the at least two single stranded DNA oligonucleotides to ligate to form a ligation product; and (c) detecting the ligation product. In some cases, the variant of the target RNA may contain one or more nucleotide substitutions in sequences that are complementary to one or both of the single stranded DNA oligonucleotides. In other words, the sequence variation may be in the complementary region to the oligonucleotide sequences. In these embodiments, the oligonucleotides may hybridize to the variant of the target RNA, but no ligation occurs absent complete complementarity. In certain cases, the site of the sequence variation may be proximal to the ligation junction (i.e., within 6, e.g., 6, 5, 4, 3, 2, or 1, nucleotides upstream or downstream of the ligation junction, but on the RNA splint).

In some embodiments, the detecting may be quantitative and, in certain cases, may be done by quantitative PCR. In particular cases, the determining step may comprise determining the amount of the target RNA relative to the amount of the variant of the target RNA. In these embodiments, two or more sets of single stranded DNA oligonucleotides may be used, wherein ligation of oligonucleotides in one set can be differentially detected and measured. This may be done by, e.g., tailing the different sets of oligonucleotides with different PCR primer sites, thereby allowing each ligation product to be amplified independently. For example, a qPCR-detected splint ligation assay is sensitive; it can quantify sub-attomole amounts of miR-122 in rat liver total RNA. For miR-122 detection the SplintR®/qPCR assay was about 30× more sensitive than the comparable TaqMan assay.

As noted above and below, the target RNA may be for example, an mRNA, a miRNA or a viral genome.

The highly sensitive and specific RNA splint ligation reactions described herein have numerous applications in the pharmaceutical and diagnostic fields. A few examples are described below but are not intended to be limiting.

Some reports have identified changes in miRNA levels associated with cancer or other clinical conditions. For example: miR-122 expression is restricted to the liver. Increased levels of this miRNA in circulation suggest liver damage. Other RNAs are also found to correlate heart disease and a variety of cancers. Recent studies have focused on RNA released in exosomes—small lipid vesicles that contain a variety of nucleic acids including miRNAs. In combination with high throughput DNA sequencing methods miRNA profiling is an important clinical indicator for many diseases.

Infectious disease can be tracked and analyzed using embodiments provided herein. RNA viruses, including polio, Ebola and influenza can be detected by RNA splint ligation methods. Unlike cDNA based methods the ligation based method is very sensitive to single base mismatches. This would allow a series of probes to be designed to detect defined point mutants in the virus to measure its mutation rate. This can be combined with DNA sequencing of the cDNA to validate these changes.

The minimal hybrid length required for ligation by a splint ligase was determined using 10 pairs of DNA probes that spanned miR-122 in two base increments. Gel electrophoresis was used to measure the extent of ligation of a FAM labeled probe to an unlabeled probe. Surprisingly, probe B required few as only four bases of complementary to the 5' end of miRNA-122 for ligation to probe A. However, the 3' end of the miRNA required probe A to have six to eight bases complementary to miR-122 for ligation. These results demonstrate that for miRNAs at least 12 of the 22 bases can be used as ligation junctions for DNA probes. This allows flexibility in probe design. Using the same set of RNA: DNA hybrids very little ligation was detected with either T4 DNA ligase or T4 RNA ligase 2.

To obtain quantitative data on the ligation rate for three ligases, capillary electrophoresis was used to determine the ratio of ligated to unligated probe A. Probes were named by the number of nucleotides complementary to the miRNA, for example probe A10 (10 complementary bases) was ligated to probe B12 (12 complementary bases). Each probe also contained 21 or 22 nt of additional sequence non-complementary to the miRNA target, designed to match PCR primer regions for qPCR amplification/detection (see below). The CE traces for the elution of ligation reaction at three different reaction times showed the unligated 32 nt starting material (S) and 65 nt ligated product (P). Only FAM labeled probe A is detected; probe B did not contain a fluorescent label. There was a dramatic difference in ligation rates for the three enzymes. At the first time point, 5 minutes, the splint ligase achieved complete ligation of the two probes. However, at two hours T4 DNA ligase and T4 RNA ligase 2 had less than 10% ligated product. Hence the splint ligase was over 200× more efficient under these reaction conditions in ligation of the DNA probes annealed to an RNA splint than either of the T4 phage enzymes, consistent with previous reports (for T4 DNA ligase and T4 RNA ligase 2). The splint ligase had faster turnover and much tighter binding than T4 DNA ligase using an RNA: DNA duplex. The splint ligase had a 20-fold higher kcat than T4 DNA ligase and a KM less than 1 nM compared to a KM of 300 nM for T4 DNA ligase.

To test the utility of a splint ligase in detecting miRNAs in a biological sample a dual quenched probe for miR-122 was designed. MiR-122 was chosen because it is an abundant miRNA that is liver specific. The splint ligation based assay had two steps, ligation of miRNA specific probes followed by PCR amplification and detection using miRNA-specific quenched oligonucleotide (oligo). The dual quenched oligo, synthesized by IDT, Integrated DNA Technologies, contained a 3' quencher and an internal ZEN™ quencher 8 nucleotides from the 5' fluorescein. During PCR amplification the quencher is separated from the fluor by the 5' to 3' exonuclease activity of the Taq DNA polymerase. Double quenched probes show improved sensitivity and reduced background fluorescence compared to those with a single quencher.

A standard curve was constructed using four-fold serial dilutions of a synthetic miR-122 RNA oligo and 1 μg total yeast RNA to mimic conditions in a biological sample. The splint ligase qPCR method could detect less than 10 zeptomoles of the synthetic miR-122 in isolation. To test the sensitivity of the assay in the presence of a mRNA background, the same assay system was used to measure endogenous miR-122 in a rat liver total RNA sample. The assay was performed in triplicate with a series of five-fold dilutions of the total RNA, from 1,000 pg to 8 pg. The calculated concentration of miR-122 from the standard curve is 130 pg per pg rat liver total RNA which is about two fold higher than the reported value of miR-122 of 60 pg/μg of total liver RNA (17). The difference in miR-122 concentrations detected between the current and previously reported methods may be due to variation between the rat liver RNA samples.

Members of miRNA gene families (e.g., the let-7 family) often have very similar sequences. There are eight described members of the let-7 family in humans that only differ by one or two nucleotides from the let-7a base sequence (32). The let-7 miRNAs are of interest due to their regulatory role as tumor suppressors and in embryonic development, thus accurate quantitation of let-7 levels in different tissues, stages of the cell cycle, and in tumors is of interest to further elucidate these roles. We used the natural diversity of let-7 family to test the ability of the splint ligase method to detect miRNAs that differ by a single base mismatch. We designed three pairs of DNA probes for the specific detection of let-7b, let-7c or let-7g, fully complementary only to their target sequences. Each set of probes was hybridized and ligated in the presence of all eight members of the let-7 family. Negative controls include the absence of either probe A (−A), probe B (−B), SplintR® ligase (−R) or absence of the stacking DNA oligo complementary to probe A, (−S). For all three probe sets, ligation is only observed when the specific let-7 probes are hybridized and ligated to their complementary miRNA.

A stacking oligo was used to enhance ligation for reactions that have a short overlap between the miRNA and probe A. The stacking oligo was complementary to probe A and is adjacent to the 3' end of the miRNA, producing a dsDNA. The stacking oligo could not be ligated to the 3' end of the miRNA because it lacks 5' phosphate, thus only serves to extend the region of double stranded nucleotide to provide a binding region for the ligase. These oligos were used in the detection of Let-7b and let-7c, which have only a 5 by and 4 by overlap between the miRNA and probe A. When the stacking oligo was omitted, lane (−S), no ligation was observed. The let-7g probe set, which has a six base overlap with the miRNA, does not require a stacking oligo for efficient ligation. The enhanced ligation could be caused by stacking interactions between the 3' terminal base on the miRNA and the adjacent base of the 5' end of the stacking oligo. A second factor the ds DNA generated by the stacking oligo could enhance binding and ligation by SplintR. For dsDNA base stacking has been calculated to add approximately 1 kcal/mole to the stability of the duplex.

The let-7 study demonstrates that SplintR® ligase can discriminate single base mismatches on either side of the ligation junction. For example, there is only a single base difference between let-7b and let-7c, a G to A transition at the 6th base from the end of the miRNA. This nucleotide difference is located on the donor side of the ligation junction. A specific probe B was designed that had a 5' terminal C that is complementary to the G. As seen in the upper panel of FIG. 4A ligation was only observed for the correct match between the probes for let-7b and the correct let-7b miRNA. No ligation was observed to the seven other let-7 miRNAs. The splint ligase could also discriminate between mismatches at the acceptor side of the ligation junction. Let-7c has a G at the 4th base from the end of the miRNA. However, five of the other let-7 miRNAs, which do not ligate to the probe, have an A at this position (FIG. 4B, middle panel). This meant that the ligase discriminated between the incorrect rA:dC mismatch and the correct rG:dC match at the 3' terminus of probe A.

Isoform specific detection was achieved even when the mismatched base was one base from the ligation junction. The ligation junction for let-7g is GU|AC while four other let-7 have GU|AU. A vertical line indicates the ligation junction. There are two factors that determine the specificity of ligation, the ability of splint ligase to discriminate between correctly paired nucleotides and the stability of the RNA:DNA hybrid.

Temperature can an important factor for both the activity and specificity of SplintR® ligase detection method. It was found that the temperature effected specificity using the let-7b specific probe set, with a 5 base overlap between probe B and the miRNA. These experiments did not contain a stacking oligo. (1) miRNA splinted probes were hybridized and ligated; and (2) In the presence of a let-7 specific dual-labeled probe, qPCR amplification and detection was performed. The hybridization and ligation reactions were incubated 100 min at three different temperatures: 16° C., 25° C. and 37° C. Each ligation reaction included a 15,000 fold excess (w/w) of non-specific yeast RNA over the miRNA target. The exogenous RNA was added to mimic biological conditions were miRNA often makes up less than 0.01% of the total cellular RNA. The let-7 specific probe contained a 5' FAM fluorescent dye and 3' terminal quencher and an internal ZEN quencher 8 bases from the 5' fluor. The qPCR probe is similar in design to the one used for miR-122 detection. The presence of two quenchers increases the signal to noise ratio and improved detection. The let-7 qPCR probe is 24 nt long probe with 21 nt complementary to probe A and only 3' nt complementary to the 3' end of let-7b. Since the last three nucleotides in the let-7 family are conserved this probe can detect all members of the let-7 family.

The specificity of the assay was found to be dependent upon the hybridization temperature. When the ligation reaction was performed at 16° C. there is only a slight preference for detection of let-7b over the other let-7 isoforms was observed, with significant signal observed in the presence of all members of the family. The specificity for lrt-7b improved when the ligation step reaction temperature was increased to 25° C., however, and at 37° C. there was a dramatic increase in specificity for let-7b detection compared to the other let-7 isoforms. Even after 40 cycles there was very little signal observed when the target miRNA were let-7 isoforms other than let-7b. Surprisingly, the increase in specificity gained by increase in ligation temperature was not accompanied by a decrease in sensitivity: for all three temperatures the Cq value for let-7b is 18 to 20 cycles. Very specific ligation was achieved at 37° C., a temperature significantly higher than the calculated Tm, 14° C., for a 5 base pair hybrid between probe A and the 3' end of let-7. However, probe B formed a stable 17 by hybrid with let-7b and had a calculated Tm of 50° C. (34).

The length of the overlap between the miRNA and DNA probe may potentially be an important factor for ligation. Three probes with different length of complementarity to the miRNA; let-7b (4 by overlap), let-7-b (5 by overlap) and let-7g (6 by overlap) were used for splint ligation followed by qPCR detection. The ligation product was amplified by PCR and detected using the dual quenched let-7 qPCR probe described above. Hybridization and ligation were at 37° C. As anticipated the longest overlap resulted in the most efficient ligation. Increasing the length of the probe A overlap with the miRNA from 4 to 5 by results in a 21-fold increase in sensitivity. When the length of overlap is increased to 6 by the sensitivity of the assay increases an additional 130-fold. The ligase-qPCR method was a significantly more sensitive method for detecting ligation products than the gel based assay described above. The gel assay did not show any ligation with a 2 or 4 base overlap and modest ligation with a 6 base overlap. However, the qPCR method for let-7 detection found that DNA ligation can be detected with a 4 or 5 base overlap between the probe and miRNA, albeit at 100 to 1,000 fold lower efficiency compared to detection of a 6 base overlap. All references cited herein are incorporated by reference.

EXAMPLES

Example 1

Assay of Ligation of DNA Oligonucleotide Substrates Using an RNA Splint

In vitro ligation assay—Ligase substrates were prepared from a variety of sequences. The sequences used as a standard were a 30 nt deoxynucleotide ssDNA fragment modified with a 5'-phosphate and a 3'-fluorophore (e.g., SEQ ID NO:3) and a 20 deoxynucleotide ssDNA acceptor fragment (e.g., SEQ ID NO:2) with unmodified termini annealed to an unmodified complementary strand composed of either DNA or RNA (e.g., SEQ ID NO:4). Ligations of 100 nM of the labeled, pre-annealed oligonucleotide structure were performed in ligation buffer (50 mM Tris pH 6-9, 10 mM $MgCl_2$, 1 mM DTT and 10 μM ATP-1 mM ATP) at 15° C.-40° C. The assay was initiated by addition of ligase (T4 DNA ligase or PBCV-1 ligase) to a final concentration between 10 μM and 10 μM and incubated at 16° C. or 20° C. Reactions were quenched with 100 mM EDTA, diluted to 1 nM in DNA with water, and analyzed by high throughput capillary electrophoresis.

Fragment analysis by high throughput capillary electrophoresis (CE)—CE samples were prepared by dilution to 0.5 nM-2 nM in total FAM-label using $ddH_2O$. The GeneScan™ 120 LIZ® Size Standard (Applied Biosystems, Carlsbad, Calif.) was diluted 1:40 in formamide and 10 μl of this solution combined with 1 μl of each sample before application to either a 3130xl Genetic Analyzer (16 capillary array) or an 3730xl Genetic Analyzer (96 capillary array) (Applied Biosystems, Carlsbad, Calif.) at a 36 cm capillary length with POP7 polymer. Data was collected via Applied Biosystems Data Collection software and analyzed using PeakScanner™ software (V 1.0) (Applied Biosystems, Carlsbad, Calif.). The retention times and areas of all peaks in the blue (FAM) channel were recorded. Oligonucleotides (30-mer starting material, adenylylated 30-mer, and 50-mer ligation product) were identified by co-elution with synthetic standards. The fraction of each oligonucleotide in the sample was determined by dividing the peak area of each by the total peak area of all three oligonucleotides. The results are shown in FIG. 2(A)-2(D) for T4 DNA ligase and PBCV-1 ligase. The graphs in FIGS. 3-5 were determined from peak areas.

Example 2

Design of RASL Probes for Amplification

Figure 7A:
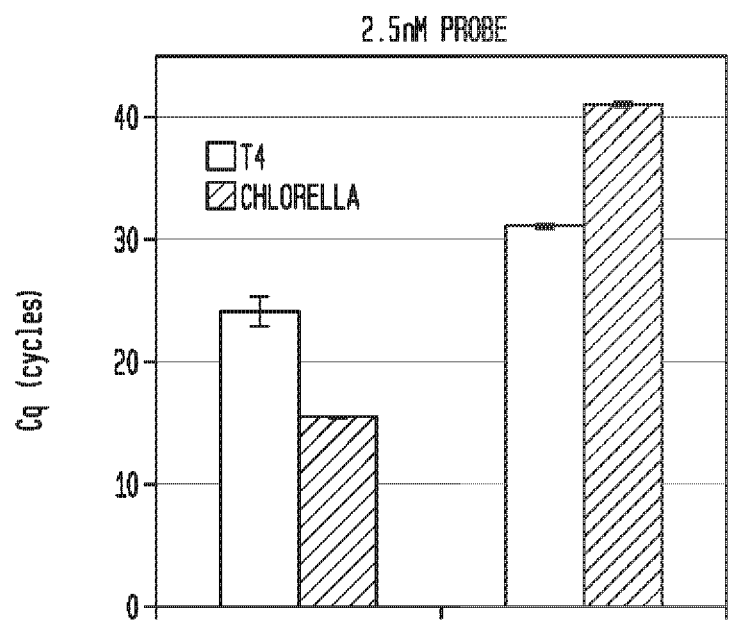
FIG. 7(A)-7(B) shows results of a RASL assay using PBCV-1 ligase or T4 DNA ligase on ssDNA oligonucleotide substrates as described in FIG. 1 to determine background signal and rate of reaction.
Figure 7B:
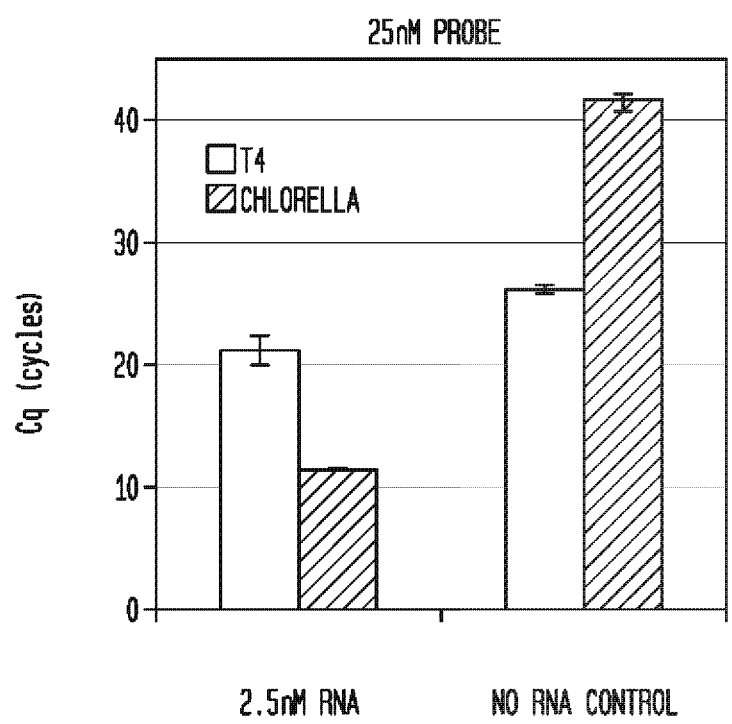

```
RASL probes
                                      (SEQ ID NO: 5)
L (/5phos/CGGTAAGACCTTTCGGTACTAGATCGGAAGAGCACAC);
and (SEQ ID NO: 6)
R (GGAAGCCTTGGCTTTTGGAACGTTGCGTCGAGTTTTC)
``` were designed to target the 3' region of the luciferase RNA (Promega, Madison, Wis.). Probes at 2.5 nM or 25 nM, with or without 2.5 nM luciferase RNA were mixed together in 25

µl of 1×T4 DNA ligase buffer (New England Biolabs, Ipswich, Mass.). The mix was heated to 65° C. for 10 minutes to denature the RNA and then at 45° C. for 60 minutes for the probe to anneal. Either 0.25 µg of PBCV-1 ligase or T4 DNA ligase (New England Biolabs, Ipswich, Mass. (M0202S, ~250 NEB units)) was added and the ligation mix was incubated at 37° C. for 60 minutes. 1 µl of the ligation mix was used for qPCR analysis using primers (GTGTGCTCTTCCGATCT (SEQ ID NO:7) and GGAAGCCTTGGCTTTTG (SEQ ID NO:8)) with Taq DNA polymerase using standard condition with PCR condition at 95° C. for 2 minutes and then 50 cycles at 95° C. for 10 minutes, 52° C. for 15 minutes and 68° C. for 30 minutes. The results are shown in FIG. 7.

Here, in the absence of template, the background signal using PBCV-1 ligase is reduced compared to T4 DNA ligase where at least 10% and as many as 50% (5-15 cycles) more thermocycles would be required during PCR amplification before a background signal was detected.

Where a positive signal from amplification of an RNA splint ligated DNA was detected, this occurred after 10%-50% (5-15) fewer cycles of amplification than would a positive signal using T4 DNA ligase for the same DNA.

Example 3

Figure 4A:
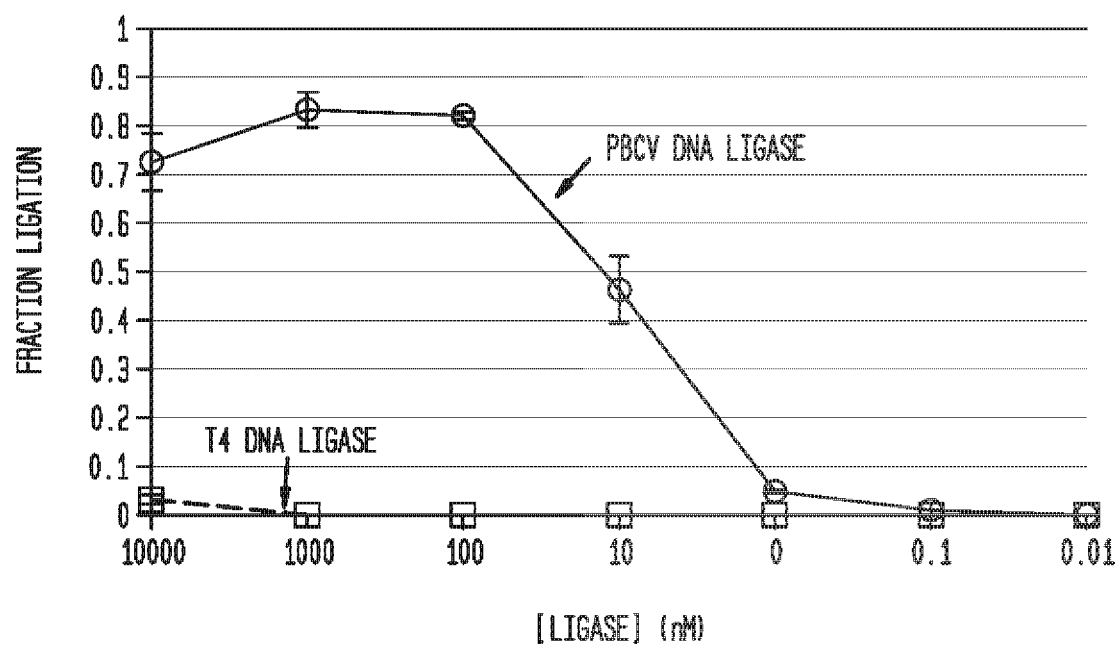
FIG. 4(A)-4(B) shows ligation of the same oligonucleotide substrates splinted by RNA reverse complements using T4 DNA ligase and PBCV-1 ligase, at a range of concentrations (1 µM-10 µM) at 20° C. in standard ligation buffer containing either 1 mM ATP or 10 µM ATP and 100 nM pre-annealed nicked substrates. 4(A): DNA-DNA ligation splinted by RNA reverse complements in the presence of 1 mM ATP. 4(B): DNA-DNA ligation splinted by RNA reverse complements in the presence of 10 µM ATP. PBCV-1 ligase ligated DNA oligonucleotides splinted by RNA in buffers containing 1 mM ATP or 10 µM ATP with similar ligation activity. T4 DNA ligase had improved activity at 10 µM ATP only but that activity was at least 5 fold, 10-fold, 20 fold, -50 fold or 100 fold less than that of PBCV-1 ligase under the same conditions. PBCV-1 ligase but not T4 DNA ligase could ligate detectable amounts of oligonucleotide substrates splinted by RNA reverse complements in buffers containing high ATP concentrations.
Figure 4B:
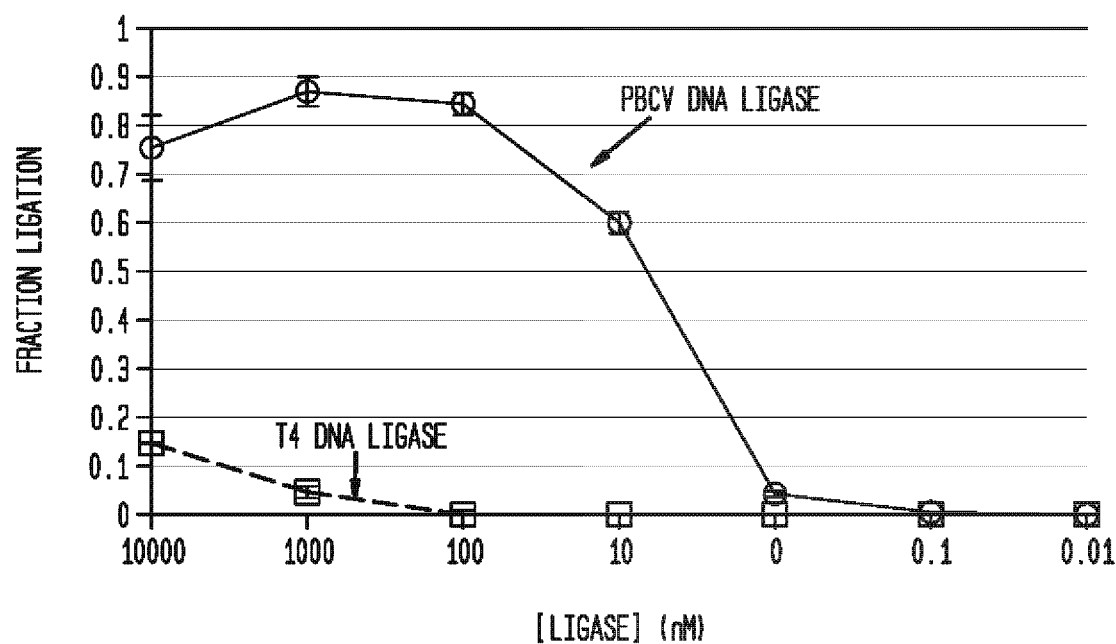
Figure 5:
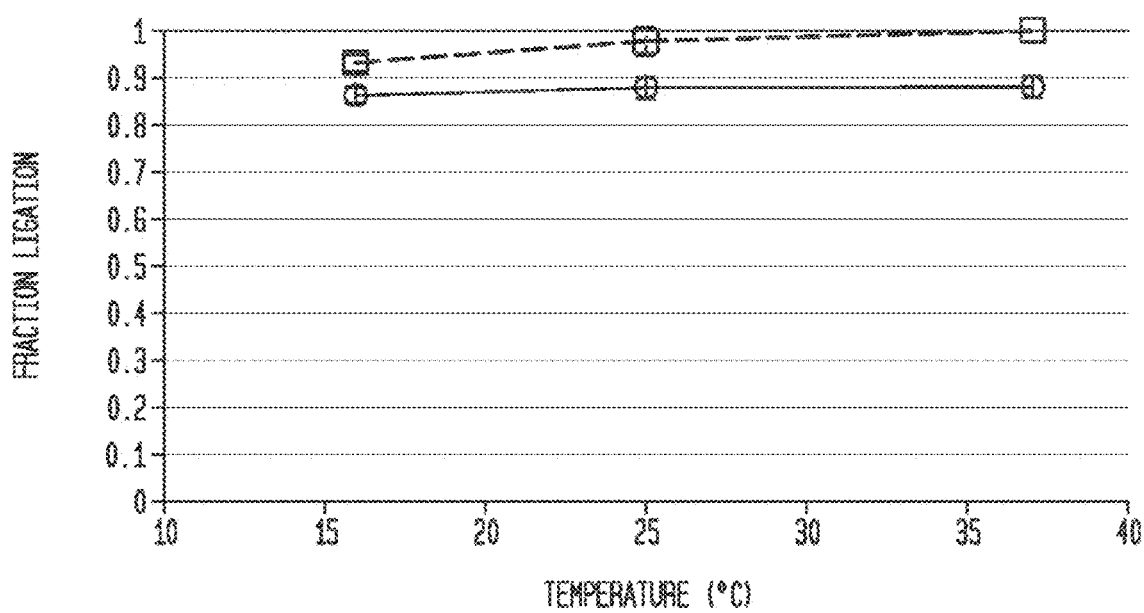
FIG. 5 shows PBCV-1 ligase RNA-splinted DNA ligation activity at multiple temperatures. DNA-DNA ligation splinted by two different RNA templates was conducted at 16° C.; 25° C.; and 37° C. The first DNA oligonucleotides and their reverse complement were standard templates as described in FIG. 9 (square) and a second template having the sequence described in the Sriskanda, et al., (1998) (circles) was also used showing that the sequence had little or no effect on ligation. Reaction conditions were 1 µM PBCV-1 ligase, 250 nM RNA-splinted oligonucleotide substrate in standard ligase buffer for 30 minute incubation.
Figure 6:
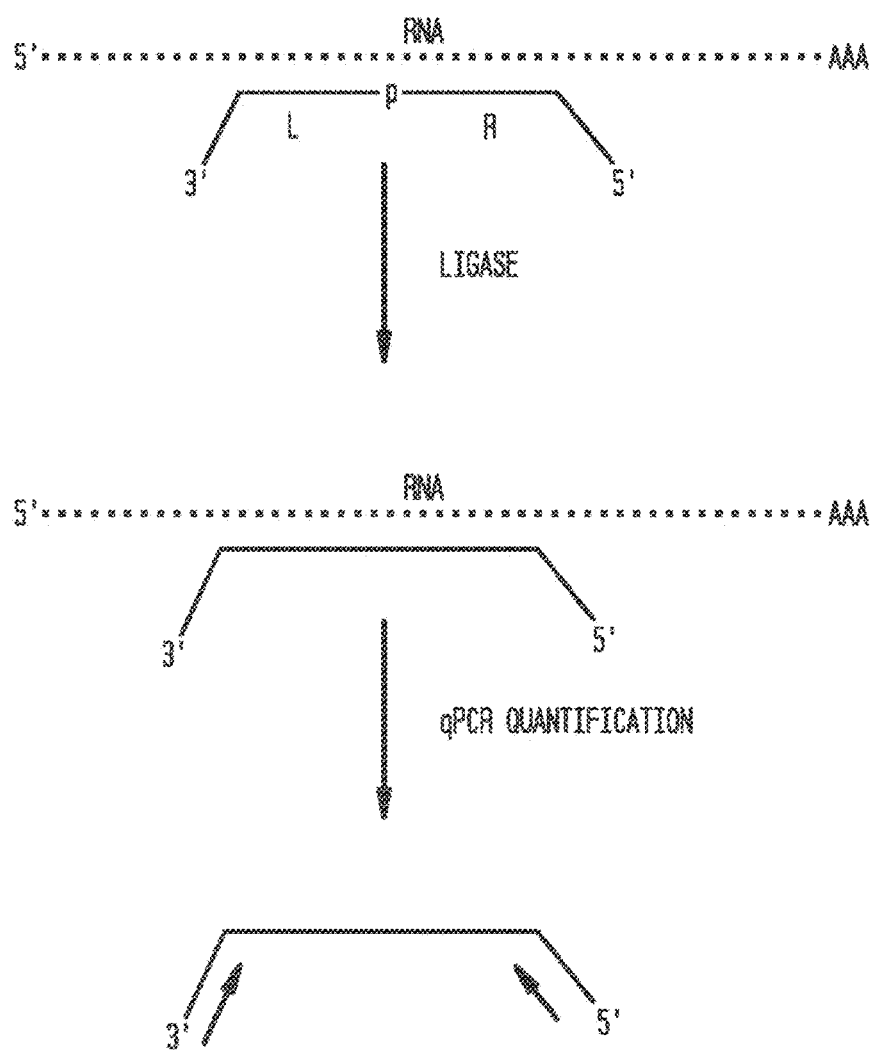
FIG. 6 shows qPCR-detected RASL assay design using an RNA splint ligase. DNA probes were designed to have a region complementary to the RNA target and a qPCR priming region. Correctly annealed probes form a backbone-nick with no gaps, ligatable by an RNA splint ligase. Successful ligation in the presence of probe generates an amplifiable DNA sequence that can be quantified by qPCR.

Characterization of PBCV-1 Ligase in a Comparison with T4 DNA Ligase at Varying Concentrations of Ligase and ATP FIG. 4(A)-4(B) shows the results of reacting 10 µM-10 µM PBCV-1 ligase or T4 DNA ligase with oligonucleotide substrates (shown in FIG. 9) in a standard ligase buffer containing 1 mM ATP or a modified buffer in which the amount of ATP was reduced to 10 µM ATP for 15 minutes at 37° C. At T4 DNA ligase concentrations >1 µM, most of the substrate is converted to AppDNA regardless of ATP concentration.

The results shown in FIG. 4(A)-4(B) demonstrate that as much as 100 fold or greater improvement in ligation efficiency was observed for PBCV-1 ligase in contrast to T4 DNA ligase for buffer containing standard amounts of ATP (1 mM). In non-optimal buffer containing only 10 µM ATP which increased T4 ligase activity, there was still at least 100 fold improvement in PBCV-1 ligase activity compared with T4 ligase activity using the standard substrate.

Example 4

Determining Splice Variants for a Single Gene

Oligonucleotides that hybridize to each exon in a gene can be prepared. Different combinations of oligonucleotides can be mixed together and ligation allowed to occur. Analysis by qPCR on the ligation products will permit determination of the frequency of different splice variants. For example, if a gene has 10 exons, hybridize DNA encoding exon 1 with exons 2-10 where each of 2-10 have a separate detectable label. Perform ligation using an mRNA splint and determine the representation of splice variants.

Example 5

MicroRNA Detection by Splint Ligation

Detection of miR-122 by splint ligation using PBCV-1 ligase.

Figure 10:
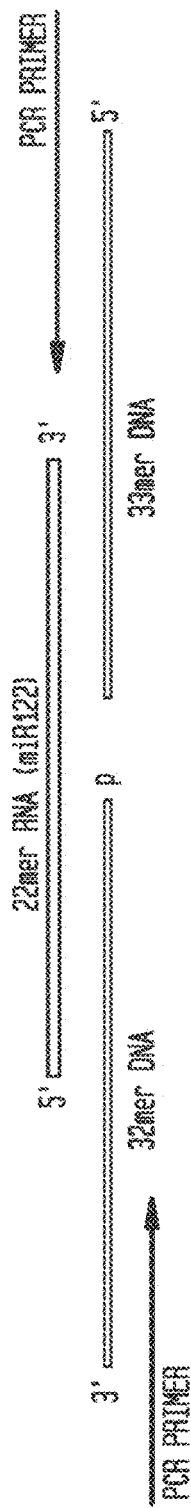
FIG. 10 shows the assay for detection of microRNAs using PBCV-1 ligase. A 5'-phosphorylated 32 nt DNA probe complementary to the 5' half of microRNA 122 and a 33 nucleotide DNA probe complementary to the 3' half of miR-122 miRNA are ligated together with PBCV-1 ligase after hybridization to target miRNA at concentrations. PCR primers re added and amplification performed.
Figure 11:
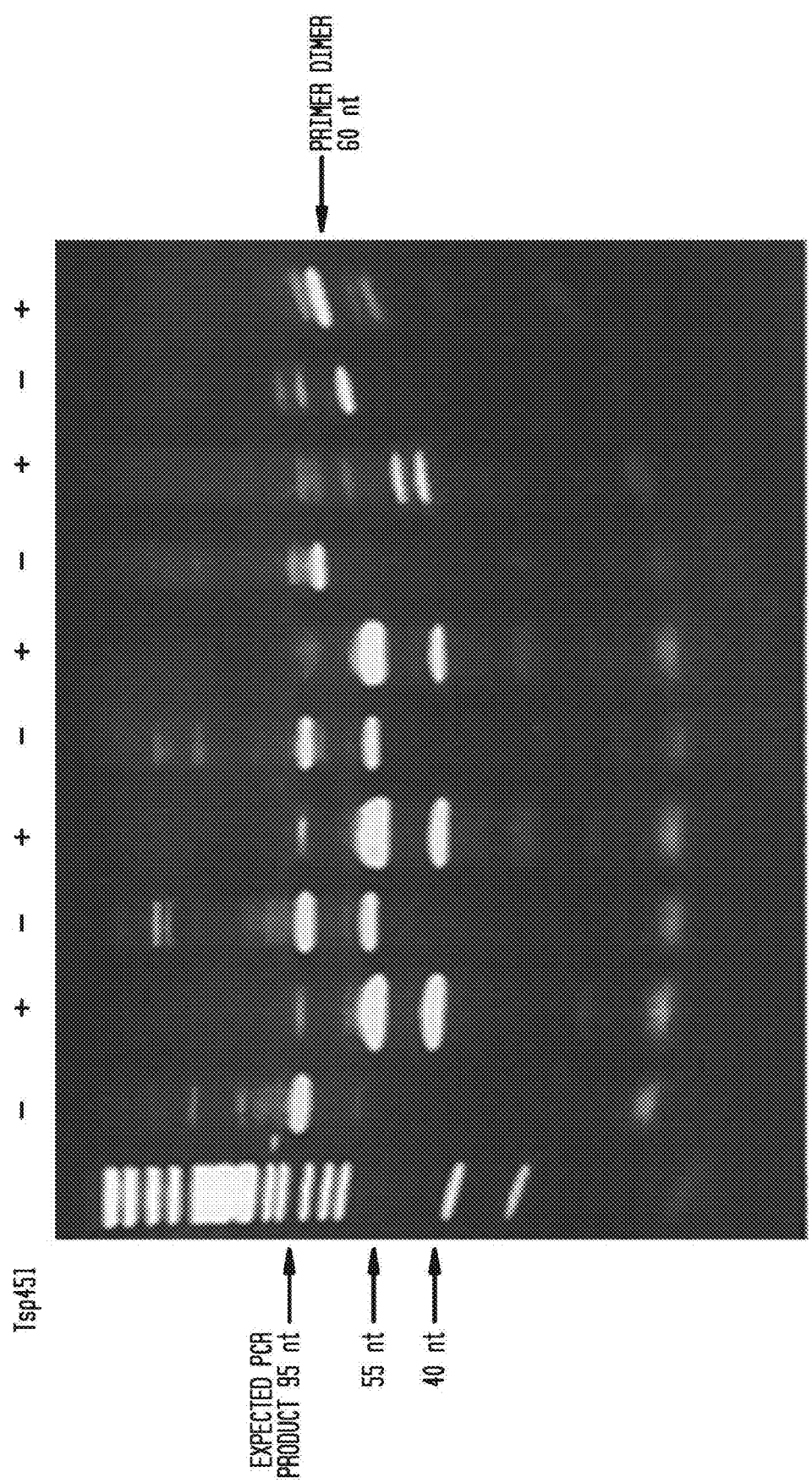
FIG. 11: Detection of miR-122 from total rat liver RNA by RNA splint ligation using PBCV-1 ligase. DNA probes were hybridized to miR-122 in total rat liver RNA (about 50 pg miRNA/pg total RNA) and ligated by PBCV-1 ligase. The non-denaturing acrylamide gel shows undigested PCR products (−) and products digested with TSp45I (+), which cleaves the desired product specifically at GT(C/G)AC. A band of 95 bases that cleaves correctly in the presence of TSp45I, indicated by arrows, was found for the two rat liver RNA samples and in the positive control containing 0.1 pg of synthetic miR-122. The negative control, which contained no RNA, and HeLa cell RNA, which does not contain miR-122, have smaller PCR products that did not give the correct fragments when digested by Tsp45I. Lanes were as follows: A: 1 µg Rat Liver RNA; B: 100 ng Rat Liver RNA; C: 0.1 pg miR-122; D: 1 µg HeLa RNA; and E: no RNA FIG. 12 schematically illustrates a detection method for identifying a miRNA by splint ligation. DNA probes can be synthesized with sequences that overlap the presumed splint miRNA sequence such that when the DNA oligonucleotides are located in an adjacent orientation, they can be ligated efficiently using a splint ligase. The ligated product hybridized to the miRNA becomes the substrate for amplification. Here the amplification is identified as PCR using a forward and reverse primer and the product can be quantified using a SYBR® green dye (Life Technologies, Carlsbad, Calif.). This method is applicable to short RNA splints or splint DNAs in addition to long split RNAs or DNAs.

FIG. 10 outlines the assay for detection of microRNA by ligation followed by PCR amplification. Either synthetic miR-122 5'pUGGAGUGUGACAAUGGUGUUUG (SEQ ID NO:9) (0.1 pg), total rat liver RNA (1 µg or 100 ng), or 1 µg total Hela cell RNA, was hybridized with two DNA probes (1 ng each) that were complementary to miRNA-122, with sequences pGTCACACTCCTCTGAGTCGGAGA-CACGCAGGG (SEQ ID NO:10) and CCTCTC-TATGGGCAGTCGGTGATAAACACCATT (SEQ ID NO:11). The RNA and DNA oligos were heat denatured at 85° C. and then slowly cooled. The ligation (containing 1 µM PBCV-1 ligase and 1× T4 DNA ligase buffer (New England Biolabs, Ipswich, Mass.) in addition to the probes and RNA source in total volume of 10 µl) was incubated at 16° C. for 2 hours. 5 µl of the ligation mixture was amplified in a 25 µl reaction with two PCR primers; CCATCTCATC-CCTGCGTGTCTCCGACTCAG (SEQ ID NO:12) and CCACTACGCCTCCGCTTTCCTCTCTATGGGCA-GTCGGTGAT (SEQ ID NO:13) and 12.5 µl of OneTaq® DNA polymerase master mix (New England Biolabs, Ipswich, Mass.). The PCR reaction was carried out for 25 cycles. FIG. 11 shows the results of use with biological samples. In this example, the identity of the PCR product was confirmed by digesting DNA with the restriction enzyme, Tsp45I. This enzyme cleaves DNA at GT(C/G)AC found in the miR-122 sequence. The digested and undigested PCR products were separated on a non-denaturing acrylamide gel and stained with ethidium bromide. The expected product band of 95 bases was observed in the two rat liver RNA samples and in the positive control containing 0.1 pg synthetic miR-122. This experiment demonstrates that microRNAs from biological samples can be detected by RNA splint ligation using PBCV-1 followed by PCR to enhance sensitivity.

Example 6

Detection of miRNAs Using Synthetic DNA Oligonucleotides in a Splint Ligase Mediated Reaction with Enhanced Specificity and Sensitivity The efficiency of splint ligase mediated detection was tested at various temperatures (for example, 16° C., 25° C. and 37° C.) for short RNA splints as short as 20-22 nucleotides and synthetic oligonucleotides having a variable number of nucleotide overlap but at least a 4 base overlap with the splint sequence where the assay is sensitive to single nucleotide mismatches in the oligonucleotides sequence with respect to the RNA splint.

Figure 12:
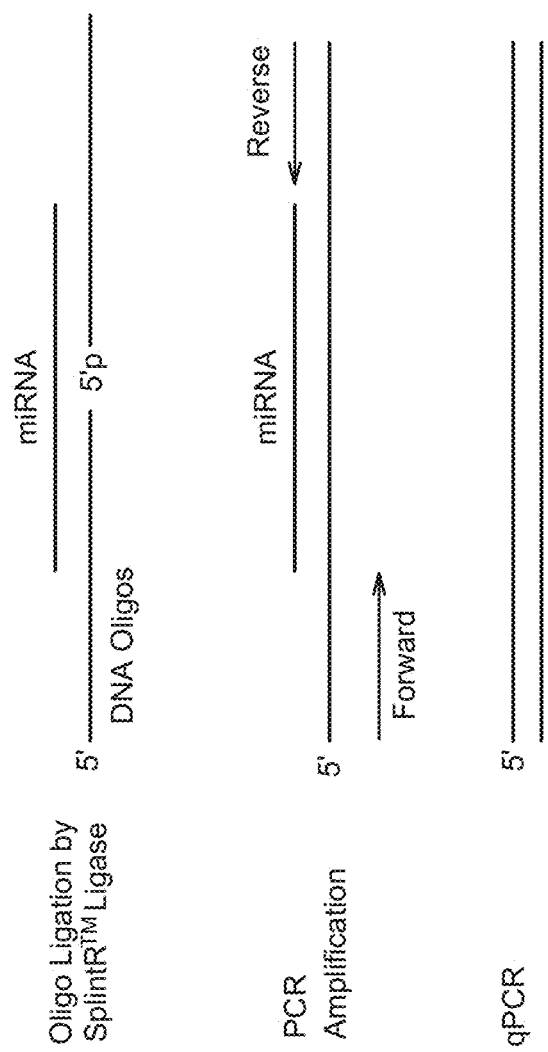

The assay as shown for FIG. 12 was performed as follows: Probes having an overall length of greater than about 8 nucleotides and as much as 100 nucleotides or greater depending on the source of the DNA oligonucleotide or the cost of synthesis and the need for an extended tail (for example as a selection marker for immobilization on a bead, array analysis or other high throughput rationale. The overlap of the complementary region with RNA splint sequence may range from at least 4 bases to as much as 30 or more bases complementary to regions of the RNA. The probes may be utilized at for example 10 to 100 fold excess of RNA splint.

The results obtained when temperatures of 16° C., 25° C. and 37° C. were tested are provided herein. In one embodiment, 1× T4 DNA ligase buffer together with substrates and enzyme was combined in a single vessel in a single reaction. The product could be analyzed by capillary electrophoresis; PAGE qPCR for example using SYBR green dye or Taq-Man® probes (Life Technologies, Grand Island, N.Y.) that are complementary to the amplified sequence. The ligated DNA probes contained extensions beyond the complementary regions of the RNA target. These extensions included sequences that were complementary to PCR primers that permitted amplification of the ligated product.

This permitted several targets to be detected via ligation and amplified with the same pair of PCR primers. For DNA probes with very short overlaps of 4 to 6 bases we found that a stacking oligonucleotide enhanced sensitivity of the assay. The stacking DNA oligonucleotide is complementary to the region of the DNA probe that extends beyond the RNA target. Hybridization of the stacking oligo to the probe generated a double stranded DNA with a single stranded extension complementary to the miRNA target which enhanced ligation. The reverse PCR primer can be used as a stacking oligonucleotide. Examples of experiments showing the above are described below in Examples 7-12 and also in FIGS. 13-18.

Example 7

Comparison of PBCV-1 Ligase, T4 RNA Ligase 2 and T4 DNA Ligase for Their Ability to Ligate Two DNA Oligonucleotides Mediated by an miRNA Splint Three different ligase, T4 RNA ligase 2, T4 DNA ligase and PBCV-1 ligase (SplintR®) (New England Biolabs, Ipswich, Mass.) were compared for their efficiency in ligation of two DNA oligonucleotides; probe A [5' FAM CCTCTCTATGGGCAGTCGGTGCAAACACCATT] (SEQ ID NO:14) and probe B_[5'p GTCACACTCCA CTGAGTCGGAGACACGCAGGG] (SEQ ID NO:15) that were hybridized to an miRNA splint. The probes were designed to be complementary to miR-122 [5' UGGAGU-GUGACAAUGGUGUUUG] (SEQ ID NO:16). The region of the DNA oligonucleotide that is complementary to miR-122 is shown in bold letters.

Complementary regions of the oligonucleotides are marked by an underline. All oligonucleotides used in these studies were manufactured by Integrated DNA, Coralville, Iowa. An annealing reaction stock was prepared by mixing 60 µl (9.36 nmol) of miR-122, 120 µl (12 nmol) of DNA probe 7A and 60 µl (3 nmol) of DNA probe B and 24 µl of 10× T4 DNA ligase buffer in 240 µl total volume. The mix was heated at 95° C. for 5 minutes in a heat block then slowly cooled down to 22° C. The concentration of miR-122 was 39 pmol/µl, DNA probe A was 12.5 pmol/µl and probe B was 50 pmol/µl. The ratios and concentrations of miR122, DNA probe A and B in ligation reaction were 39 pmol/µl: 12.5 pmol/µl: 50 pmol/µl. Each ligation reaction contained 2 µl of annealing, 1 µl of 10× T4 DNA ligase buffer (50 mM Tris pH 7.5 @ 25° C., 10 mM MgCl$_2$, 10 mM DTT, 1 mM ATP), 1 µl of T4 DNA ligase (10 pmol/µl) or 1 µl of Splint R DNA ligase (10 pmol/µl) or 2 µl of T4 RNA ligase 2 (5 pmol./µl) and H$_2$O in a total volume of 10 µl. RNA ligase 2 was diluted to 5 pmol/µl with 1× RNA ligase 2 buffer (50 mM Tris pH 7.5 @ 25° C., 2 mM MgCl$_2$, 1 mM DTT, 400 µM ATP). Three master mixes were prepared for the three ligases. Six ligation tubes for each ligase were incubated at 16° C. for 6 different times (5 minutes, 10 minutes, 15 minutes, 30 minutes, 60 minutes, and 120 minutes). The ligation reactions were stopped by adding an equal volume of 2× stop buffer (50 mM EDTA, 0.1% triton in water) and kept at −20° C. Aliquots (2 µl/20 µl) was removed and mixed with 198 µl of H$_2$O and analyzed by capillary electrophoresis (CE) fragment analysis on a 96-capillary 3730xl DNA Analyzer (Applied Biosystems/Life Technologies, Grand Island, N.Y.).

Figure 13A:
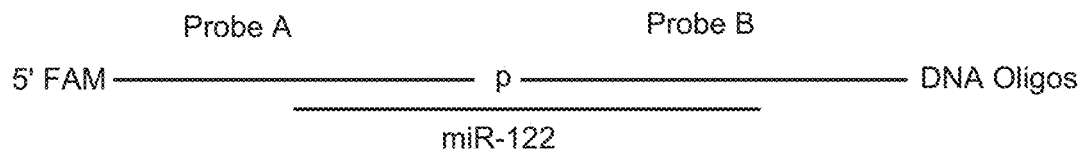
Figure 13B:
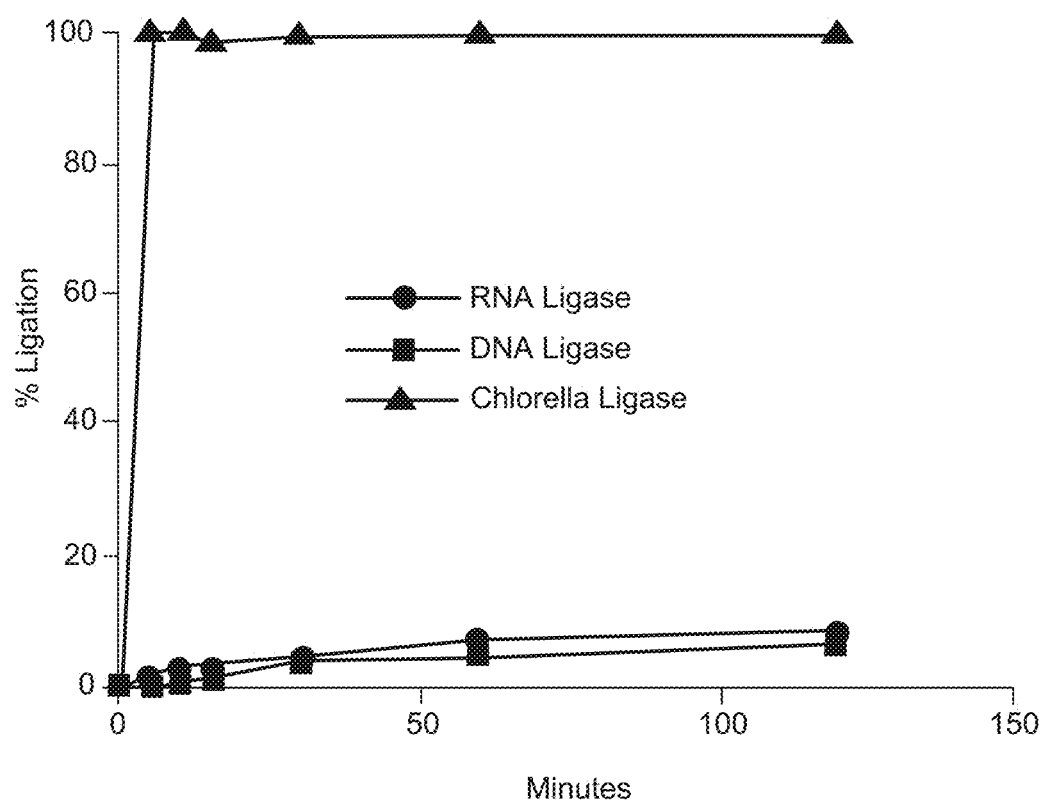
Figure 13D:
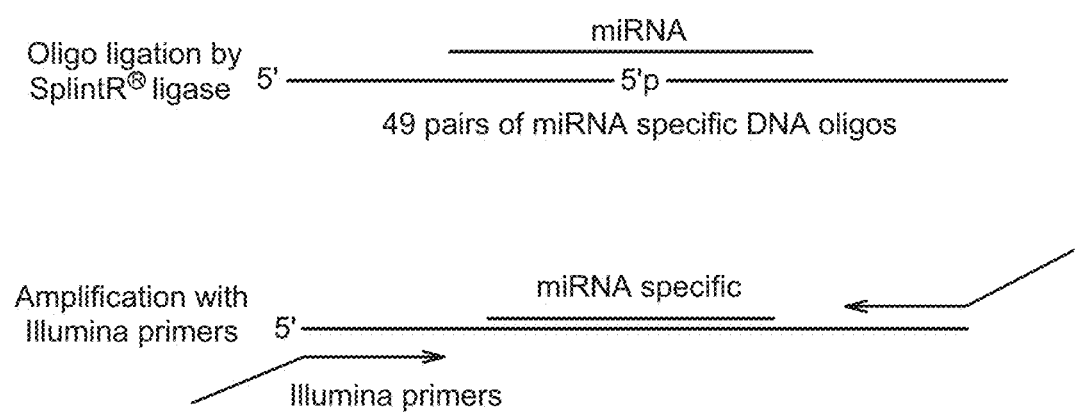

FIG. 13A shows the general ligation strategy used, and FIG. 13B shows the results of the ligation with the miRNA splint are plotted versus the time of incubation with the three ligases.

Example 8

Detection of the Minimum Length of Overlapping Sequences Between DNA Oligonucleotides and miRNA for Splint Mediated Ligation Comparing Three Different Ligases The sequences of ten pairs of DNA oligonucleotides, labeled as probe A or probe B in FIG. 14A, were ordered from Integrated DNA Technologies (Coralville, Iowa). The probes were designed to anneal to miR-122 generating a nicked RNA splinted substrate for ligation. The oligonucleotides scanned the miRNA sequence in 2 nucleotide increments. They were designed to determine the minimum overlap required for ligation. The sequences of the pairs of oligos are listed below.

```
Probe A
[1]                                            (SEQ ID NO: 17)
5' FAM CCTCTCTATGGGCAGTCGGTGCAAACACCATTGTCACACTC

[2]                                            (SEQ ID NO: 18)
5' FAM CCTCTCTATGGGCAGTCGGTGCAAACACCATTGTCACAC

[3]                                            (SEQ ID NO: 19)
5' FAM CCTCTCTATGGGCAGTCGGTGCAAACACCATTGTCAC

[4]                                            (SEQ ID NO: 20)
5' FAM CCTCTCTATGGGCAGTCGGTGCAAACACCATTGTC

[5]                                            (SEQ ID NO: 21)
5' FAM CCTCTCTATGGGCAGTCGGTGCAAACACCATTG

[6]                                            (SEQ ID NO: 22)
5' FAM CCTCTCTATGGGCAGTCGGTGCAAACACCAT

[7]                                            (SEQ ID NO: 23)
5' FAM CCTCTCTATGGGCAGTCGGTGCAAACACC

[8]                                            (SEQ ID NO: 24)
5' FAM CCTCTCTATGGGCAGTCGGTGCAAACA

[9]                                            (SEQ ID NO: 25)
5' FAM CCTCTCTATGGGCAGTCGGTGCAAA

[10]                                           (SEQ ID NO: 26)
5' FAM CCTCTCTATGGGCAGTCGGTGCA

Probe B
[1]                                            (SEQ ID NO: 27)
5'p CA CTGAGTCGGAGACACGCAGGG

[2]                                            (SEQ ID NO: 28)
5'p TCCA CTGAGTCGGAGACACGCAGGG

[3]                                            (SEQ ID NO: 29)
5'p ACTCCA CTGAGTCGGAGACACGCAGGG
```

-continued

[4] (SEQ ID NO: 30)
5'p ACACTCCA CTGAGTCGGAGACACGCAGGG

[5] (SEQ ID NO: 31)
5'p TCACACTCCA CTGAGTCGGAGACACGCAGGG

[6] (SEQ ID NO: 32)
5'p TGTCACACTCCA CTGAGTCGGAGACACGCAGGG

[7] (SEQ ID NO: 33)
5'p ATTGTCACACTCCA CTGAGTCGGAGACACGCAGGG

[8] (SEQ ID NO: 34)
5'p CCATTGTCACACTCCA CTGAGTCGGAGACACGCAGGG

[9] (SEQ ID NO: 35)
5'p CACCATTGTCACACTCCA CTGAGTCGGAGACACGCAGGG

[10] (SEQ ID NO: 36)
5'p AACACCATTGTCACACTCCA CTGAGTCGGAGACACGCAGGG

Probe A is 5' FAM labeled and probe B has a 5' phosphate to allow ligation. The miR-122 stock was 156 pmol/μl. The DNA probes A and B were at a concentration of 100 pmol/μl each. All The H$_2$O used in this study were DEPC treated. Ten annealing reactions were set with pairs of probes A and B. Each reaction contained 387 pmol of miR122, 550 pmol of DNA probe A and 550 pmol of DNA probe B in 1× T4 DNA ligase buffer, in a volume of 55 μl. The ratio and concentrations of miR-122, probe A and probe B were 7.2 pmol/μl: 10 pmol/μl: 10 pmol/μl. The oligonucleotides were heated to 95° C. for 5 minutes in a heat block then allowed to cool to room temperature. T4 DNA ligase, 10× T4 DNA ligase buffer, PBCV-1 ligase, RNA ligase 2 and 10× RNA ligase buffer were all from New England Biolabs, Ipswich, Mass. T4 DNA ligase and PBCV-1 ligase were diluted to 10 pmol/μl with 1× T4 DNA ligase buffer (50 mM Tris pH 7.5 @ 25° C., 10 mM MgCl$_2$, 10 mM DTT, 1 mM ATP). RNA ligase 2 was diluted to 5 pmol/μl with 1× RNA ligase 2 buffer (50 mM Tris pH 7.5 @ 25° C., 2 mM MgCl$_2$, 1 mM DTT, 400 μM ATP).

Figure 14B:
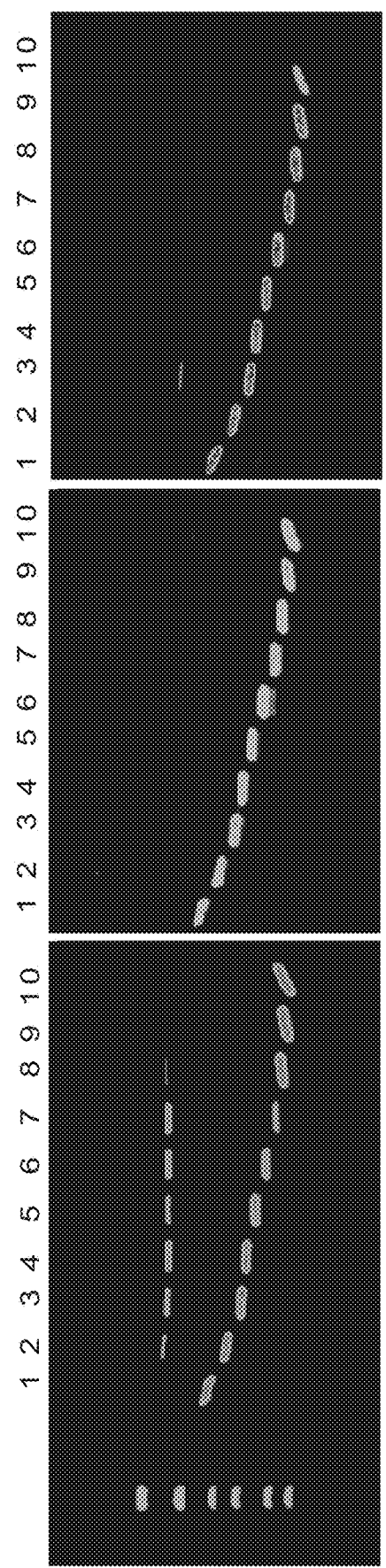

The ligation conditions were the same as describe in Example 2. Five μl of the three hybridized oligos (probe A, probe B and miRNA) were mix with 1 μl (10 pml) of T4 DNA ligase, 1 μl (10 pml) of PBCV-1 DNA ligase or 2 μl (10 pml) T4 RNA ligase 2. For the T4 DNA ligase and PBCV-1 DNA ligase reactions 1 μl of 10× T4 DNA ligase buffer was added to the reaction. For the T4 RNA ligase 2 reaction 1 μl of 10× T4 RNA ligase 2 buffer was used. Final volume for all reactions was 10 μl. The ligation reactions were incubated at 16° C. for 1 hour for T4 DNA ligase and PBCV-1 DNA ligase and 37° C. for 1 hour for T4 RNA ligase 2. The ligation products were analyzed by polyacrylamide gel electrophoresis. Two μl of the ligation reaction were mixed with 5 μl 3× denaturing loading dye, 8 μl of H$_2$O and heated at 95° C. for 5 minutes before loaded onto a Novex® 15% TBE urea gel (Invitrogen, Grand Island, N.Y.). A FAM labeled ssDNA ladder was also loaded as size a marker. Gels were scanned with Typhoon™ 9400 (GE Healthcare bio-Sciences, Pittsburgh, Pa.). The results are shown in FIG. 14B.

Example 9

Comparison of the Sensitivity of Two Different Ligases for RNA Mediated Splint Ligation Using a Luciferase mRNA Splint in a Background of Non-RNA Splint The experimental details for this example are provided in Lohman, et al., Nucleic Acids Research, 42:1831-1844 (2014) incorporated herein by reference.

Figure 15A:
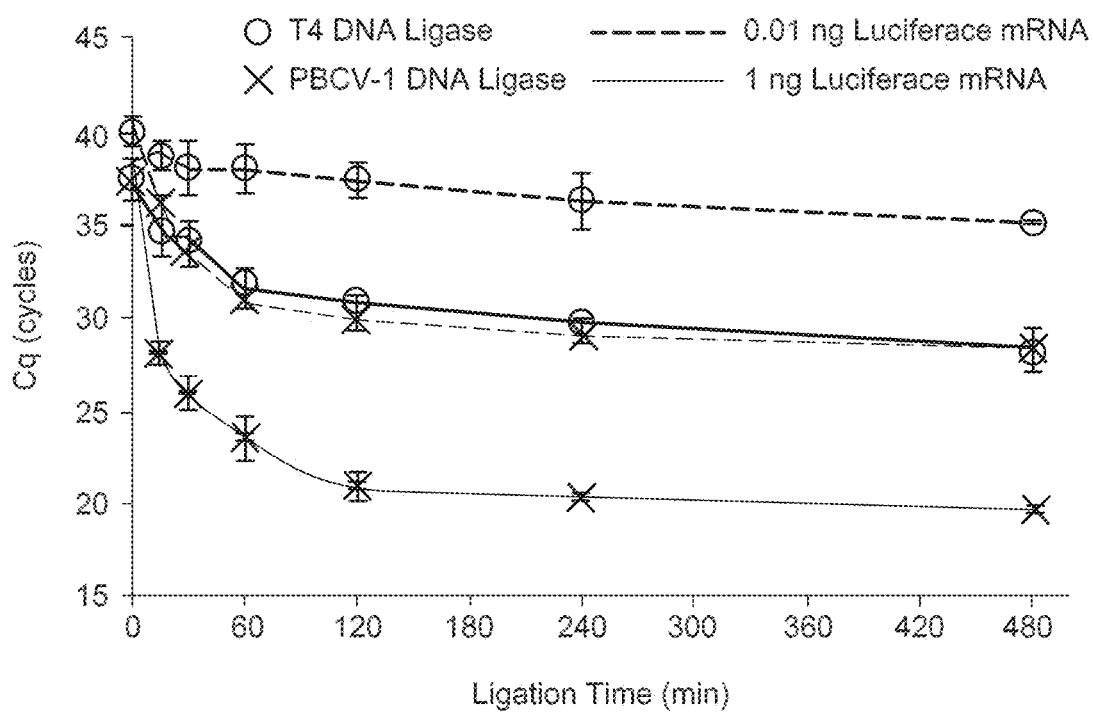
FIG. 15A-15B shows ligation of 100 nM pre-annealed standard oligonucleotide substrates on 0.01 ng or 1 ng mRNA luciferase RNA splint using T4 DNA ligase, or PBCV ligase, over a time course of 0-480 minutes and determining the efficiency of the ligase reaction by determining the number of cycles required to generate detectable product. At every time point, the splint ligase significantly outperformed the T4 DNA ligase.
Figure 15B:
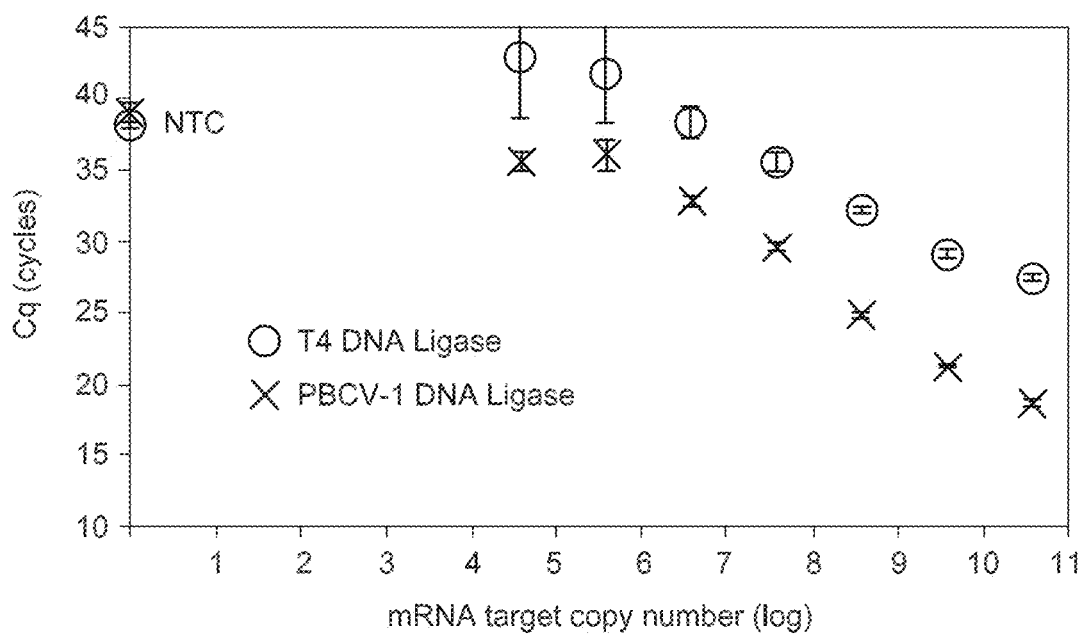

FIG. 15A-15B shows ligation of 100 nM pre-annealed standard oligonucleotide substrates on 0.01 ng or 1 ng mRNA luciferase RNA splint using T4 DNA ligase, or PBCV ligase, over a time course of 0-480 minutes and determining the efficiency of the ligase reaction by determining the number of cycles required to generate detectable product. At every time point, the splint ligase significantly outperformed the T4 DNA ligase.

Example 10

Figure 16A:
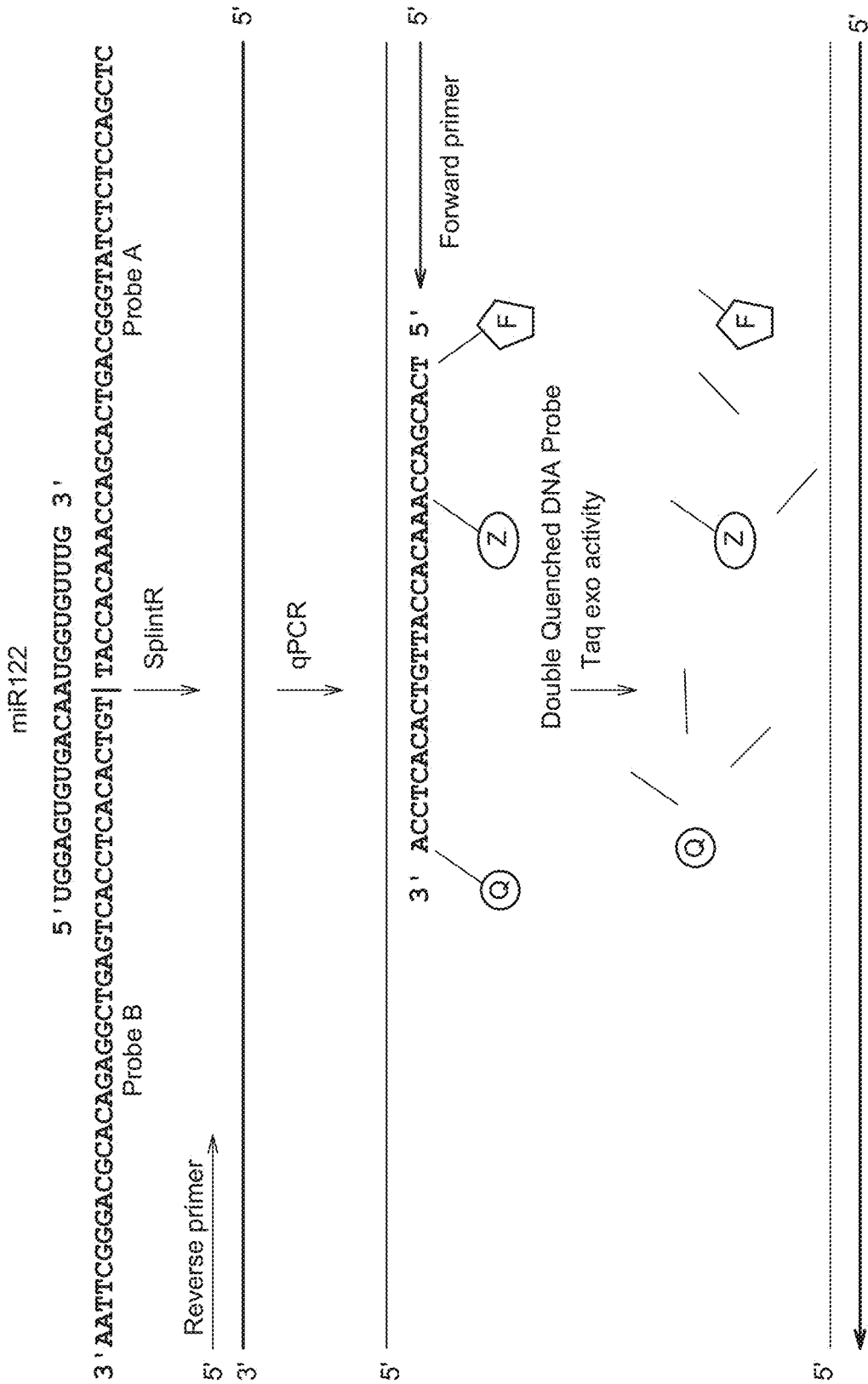
FIG. 16A-16C shows that splint ligation using splint ligase is efficient and sensitive even in the background of total liver RNA in FIG. 16B or yeast RNA in FIG. 16C.
Figure 16B:
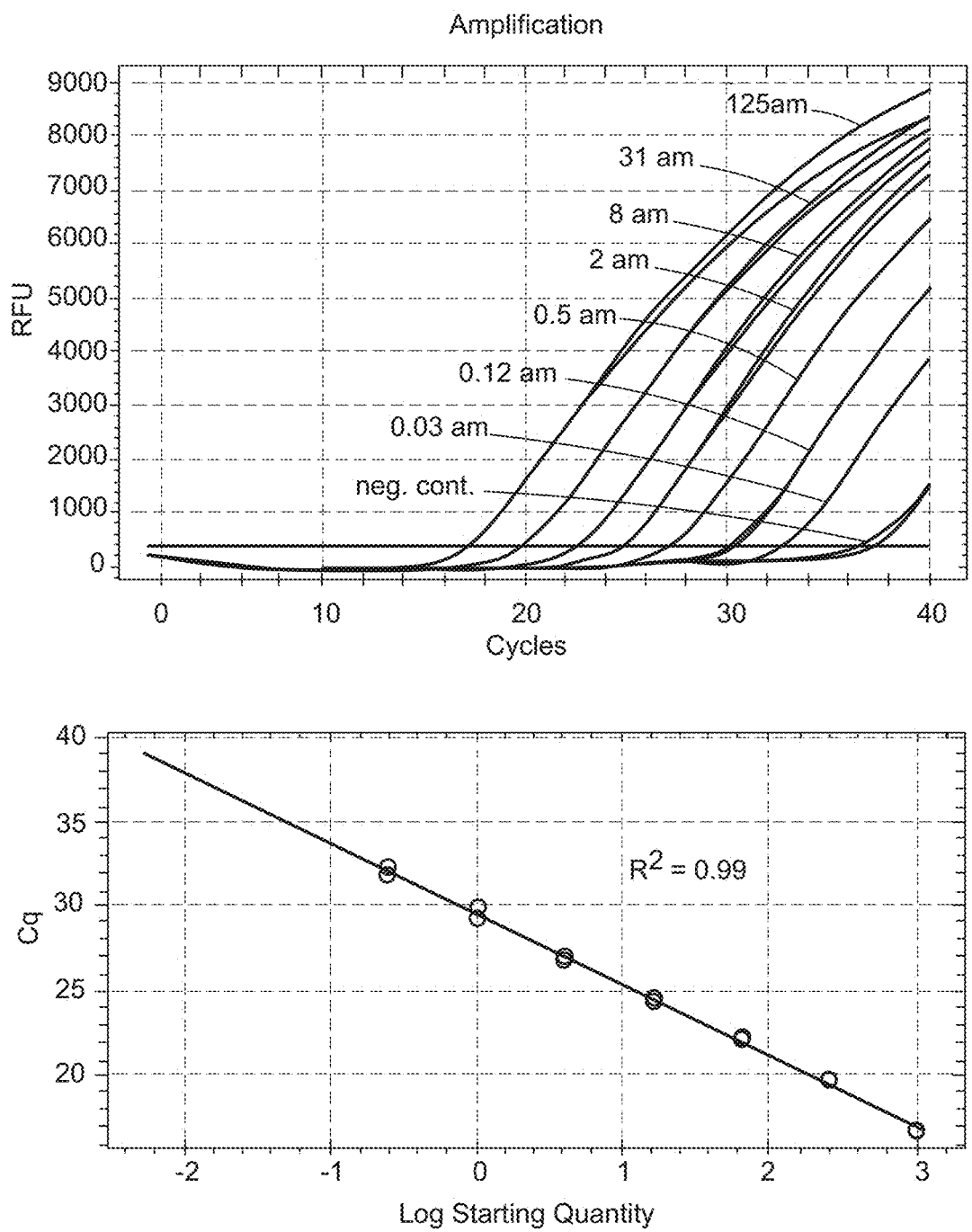
Figure 16C:
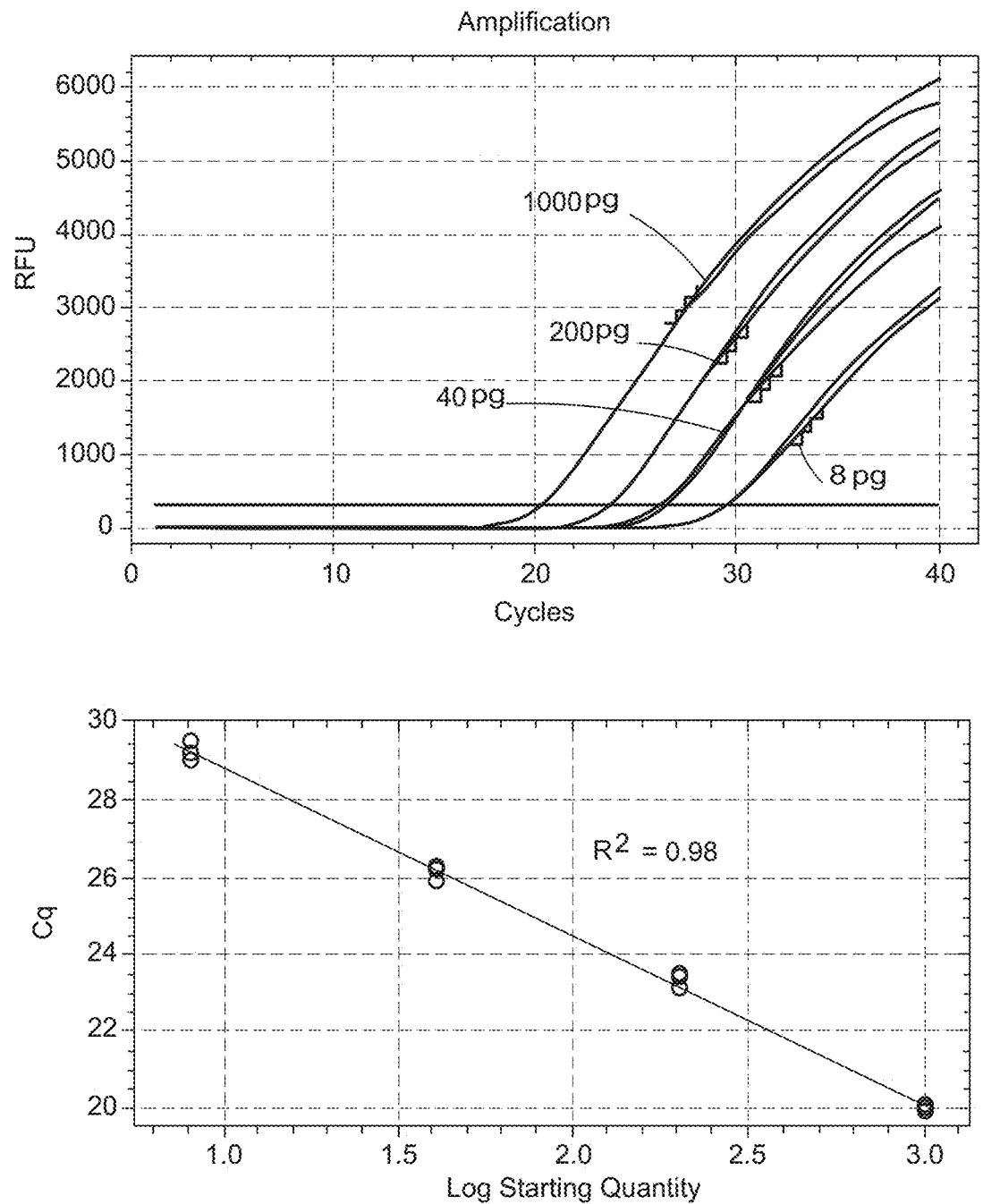

Quantitative Detection of miR-122 by Splint Ligation in Rat Liver Total RNA Using a TaqMan Probe The miRNA-122 splint ligation by PBCV-1 ligase was used to measure the amount of miR-122 in an RNA sample from rat liver total RNA (see FIGS. 16A, 16B and 16C). These values were compared to a standard curve with synthetic miR-122 to determine the amount of microRNA in the sample.

In FIG. 16C a standard curve for miR-122 was generated using the following probes. The region of the probe complementary to miR-122 is shown in bold Probe 6A: (SEQ ID NO: 37)
5' CTCGACCTCTCTATGGGCAGTCACGACCAAACACCAT Probe 6B: (SEQ ID NO: 38)
5' pTGTCACACTCCACTGAGTCGGAGACACGCAGGG qPCR forward primer: (SEQ ID NO: 39)
5' GCTCGACCTCTCTATGGGC qPCR reverse primer: (SEQ ID NO: 40)
5' CCCTGCGTGTCTCCGACTCAG miR-122 (SEQ ID NO: 41)
5' UGGAGUGUGACAAUGGUGUUUG TaqMan probe for miR-122: 5' 6CACGACCAAACACC0 (SEQ ID NO:42) (6: 6-FAM, 0: MGB/NFQ) miR-122 was diluted in 1/4 serial dilution with H$_2$O from 12.5 fmol/μl to 0.003 fmol/μl. 1 μl of each dilution was mixed with 1 μl (1 μg) of yeast RNA, 1 μl (1 μM) of DNA probe 6A (pair 6), 1 μl (1 μM) of DNA probe 6B (pair 6), 1 μl of 10× T4 DNA ligase buffer and 5 μl of H$_2$O in a total volume of 10 μl. A negative control that had no mir-122 but yeast RNA was also included for annealing. Annealing reactions were carried out as described in Example 7. One μl of each dilution was mixed with 0.5 μl (10 pm) of Splint R DNA ligase, 1 μl of 10× T4 DNA ligase buffer and 7.5 μl of H$_2$O in a total volume of 10 μl. The concentration of miR-122 in the ligation reaction was diluted 10 fold from the annealing reaction to a concentration range of 0.125 fmol/μl to 0.03 amol/μl. Ligation reactions were incubated at 16° C. for 1 hour.

The qPCR TaqMan assay was performed in 25 μl in a 96-well plate. Each reaction contained 2.5 μl of 10× ThermoPol® detergent-free buffer (New England Biolabs, Ipswich, Mass.), 0.5 μl of 10 mM dNTPs, 0.5 μl of 100 mM of MgSO4, 0.25 μl of Hot start Taq polymerase (New England Biolabs, Ipswich, Mass.), 1 μl of ligation reaction, 1 μl of 5 μM forward primer, 1 μl of 5 μM of reverse primer and 2 μl of TaqMan miR-122 probe. Each miR-122 dilution had triplets for qPCR reaction. The plate was incubated in a qPCR thermocycler with the following program: 95° C. for 3 minutes, 95° C. for 10 seconds, and 55° C. for 30 seconds.

The Cq value, where the signal crosses the threshold value were plotted versus the number of cycles in FIGS. 16B-5C.

The miR-122 concentration in rat liver total RNA (FIGS. 16B and 16C) were detected using the PBCV-1 DNA ligase and a TaqMan probe. Rat liver total RNA was purchased from Molecular Research Center, Cincinnati, Ohio. The liver RNA was diluted from 10 ng/μl to 0.08 ng/μl in 1/5 serial dilution with H$_2$O. One μl of each dilution was used for 10 μl annealing reaction. The conditions and buffer used for annealing was the same as used for the miR-122 standard curve in FIG. 16B-16C. Each 10 μl annealing reaction was mixed with 1 μl of PBCV-1 DNA ligase, 0.5 μl of 0.1 M DTT and 0.5 μl of 10× T4 DNA ligase buffer in a total volume of 12 μl. The ligation reaction was incubated at 16° C. for 1 hour. For the qPCR reactions a 1/10 aliquot, (1.2 μl) of ligation reaction was used. Reactions were done in triplicate.

Example 11

Specific Detection of Let-7g and Let-7b by miRNA Splint Mediated Ligation Using PBVC-1 Ligase FIG. 17A shows 8 variants of let-7 miRNA (let-7-a to let-7-i). An RNA having a sequence compatible with let-7g was selected. Let-7b differed at 2 sites from let-7g while let-7i differed at 3 sites and let-7a, let-7c, let-7d, let-7e and let-7f differed at one location only. One DNA oligonucleotide had a length of 6 nucleotides for hybridizing to the RNA splint and the other oligonucleotide probe contained 16 nucleotides of sequence overlap.

DNA probes used for specific detection of Let-7g are: DNA probe A (specific for Let-7g): 5' FAM CCTCTC-TATGGGCAGTCGGTGAAACTGT (SEQ ID NO:43) DNA probe B (specific for Let-7g): 5'pACAAACTACTAC-CTCACTGAGTCGGAGACACGCAGGG (SEQ ID NO:44) Let-7g specific DNA probes A and B were in concentration of 10 pmol/μl. The annealing reaction contained 1.6 μl (16 pmol) of Let-7a, 7b, 7c, 7d, 7e, 7f, 7g or 7i were mixed with 0.5 μl (5 pmol) of Let-7 (g) specific DNA probe A, 2 μl (20 pmol) of probe B, 1 μl of T4 DNA ligase buffer and 4.9 μl of H$_2$O in a total volume of 10 μl. Note, no stacking oligos complementary to probe A was used in annealing for Let-7g specific detection. Two negative controls were included: 1: no probe A and 2: no probe B. All the 8 experimental and 2 negative controls were incubated for annealing as described before. Aliquots (5 μl) of each annealing reaction was mixed with 1 μl of T4 DNA ligase buffer, 1 μl (10 pmol/μl) of SplintR DNA ligase and 3 μl of H$_2$O in a 10 μl volume. The ligation reactions were stopped by adding 10 μl of stop buffer then mixed with 15 μl RNA denaturing loading dye. The sample was analyzed by loading 18 μl of the mix was loaded onto a 15% TBE-urea gel for electrophoresis. The gel was analyzed by Typhoon 9400.

Figure 17C:
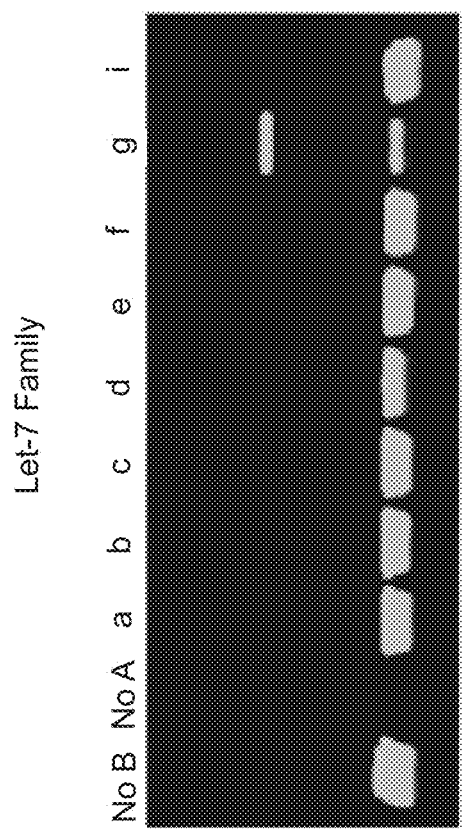

FIGS. 17B and 17C show the selective detection of let-7g with an isoform specific DNA probe that hybridizes to the last six nucleotides of the let-7g miRNA and can be ligated by SplintR ligase. This surprising observation reveals the highly sensitive nature of the splint ligase to substrates. Isoform specific detection was achieved even when the mismatched base was one base from the ligation junction. The ligation junction for let-7g is GU|AC while four other let-7 variants have GU|AU, where the vertical line indicates the ligation junction. The enzyme discriminates between the incorrect rU:dG mismatch and the correct rC:dG match.

Example 12

Specific Detection of Let-7b by miRNA Splint Mediated Ligation Using PBCV-1 Ligase Let-7 miRNA sequences are shown in FIG. 17A. qPCR assay to provide a numerical analysis of sensitivity for Let-7b miRNA probes specificity compared to other Let 7 variants.

Let-7b detection by qPCR the following oligonucleotides were purchased from Integrated DNA Technologies, Coralville, Iowa.

```
Probe A9.0                              (SEQ ID NO: 45)
5'GTCTGGTCAGAATCACCTCCTCGTCATGGGCAGGTACGGTGCAA
CC 3'

Probe B9.0                              (SEQ ID NO: 46)
5'p ACACAACCTACTACCTCACTGAGTTGGAGACACGCAGAA 3'
```

DNA dual labeled probe for detection of Let7-miRNAs.

```
                                        (SEQ ID NO: 47)
5' 56-FAM-CGTCATGGG-ZEN-CAGGTACGGTGCAAC-31ABkFQ 3' qPCR forward primer:
                                        (SEQ ID NO: 48)
5' GTCTGGTCAGAATCACCTC aPCR reverse primer:
                                        (SEQ ID NO: 49)
5' TTCTGCGTGTCTCCAACTCA
```

Annealing and ligation are combined into one reaction as following:1 μl (10 fmol) of Le-7a or b or c or d or e or f or g or i was mixed with 1 μl (100 fmol) of Let-7b DNA probe A 9.0, 1 μl (100 fmol) of Let-7b probe B 9.0, 1 μl of T4 DNA ligase buffer (10×), 1 μl of PBCV-1 DNA ligase (10 μM), 1 μl of shredded yeast RNA (1 μg) and 4 μl of H$_2$O in a total volume of 10 μl. The reaction was incubated at 37° C. for 100 minutes. For PCR, initial denaturation was carried out at 95° C. for 3 minutes, then 10 seconds at 95° C. and 30 seconds at 55° C. for the PCR cycle conditions.

qPCR was performed in a triplicate for each ligation as following: Two μl of each ligation reaction was mixed with 12.5 μl of OneTaq® Hot Start PCR 2× mix (New England Biolabs, Ipswich, Mass.), 1 μl of forward primer (10 pmol), 1 μl of reverse primer (10 pmol), 1 μl of dual labeled probe (4 pmol) and 7.5 μl of H$_2$O in a total volume of 25 μl. Triplet qPCR was done for each ligation reaction. qPCR was amplified in the same program as for miR122 qPCR. FIG. 8 shows the results of the qPCR detection. The Let-7b is used as a 100% control. The difference in Cq values for the other miRNA splints is converted to a % of those for Let-7b. These results show that there about a 100× preference for Let-7b detection compared to the other Let-7 variants (see FIG. 18A).

FIG. 17D shows the sequences of eight members of the let-7 family are shown at the left. One group of sequences for each of the three probes, let-7b, let-7c and let-7g. The sequence of the specific let-7 isoform is underlined. Nucleotides that do not match that isoform are shown in bold font. A vertical blue line shows the ligation junction for the two probes.

FIG. 17E shows that each set of isoform specific DNA probes was hybridized to all eight let-7 miRNAs. The successful ligations were detected by gel electrophoresis. The gel was not stained so only FAM labeled probe A is detected.

Negative controls include; no probe A (−A), no SplintR ligase (−R), no stacking oligo (−S) and no probe B (−B). The oligonucleotides used in each ligation are shown above the gel. The stacking oligo, which is complementary to probe A, is included in reaction with the let-7b and let-7c ligation to enhance ligation. These two probes have only a five and four base overlap with the miRNA. Hybridization of the stacking oligo to probe A results in retarded mobility on the gel.

Example 12

Gel Electrophoresis Showing the Specificity of the Assay Using a Fluorescent Probe A DNA probes were designed to selectively detected miR-Let-7-b but not other members of the Let-7 family. The sequences of eight Let-7 miRNAs (also shown in FIG. 18A) are listed below.

```
Let-7 family:
Let-7a:
                                      (SEQ ID NO: 50)
5' U G A G G U A G U A G G U U G U A U A G U U Let-7b:
                                      (SEQ ID NO: 51)
5' U G A G G U A G U A G G U U G U G U G G U U Let-7c:
                                      (SEQ ID NO: 52)
5' U G A G G U A G U A G G U U G U A U G G U U Let-7d:
                                      (SEQ ID NO: 53)
5' A G A G G U A G U A G G U U G C A U A G U U Let-7e:
                                      (SEQ ID NO: 54)
5' U G A G G U A G G A G G U U G U A U A G U U Let-7f:
                                      (SEQ ID NO: 55)
5' U G A G G U A G U A G A U U G U A U A G U U Let-7g:
                                      (SEQ ID NO: 56)
5' U G A G G U A G U A G U U U G U A C A G U U Let-7i:
                                      (SEQ ID NO: 57)
5' U G A G G U A G U A G U U U G U G C U G U U
```

The two DNA probes designed to be specific for let-7b are DNA;

```
Let-7b specific probe A;          (SEQ ID NO: 58)
5' 6FAM CCTCTCTATGGGCAGTCGGTGAAACCA Let-7b specific probe B;          (SEQ ID NO: 59)
5' pCACAACCTACTACCTCACTGAGTCGGAGACACGCAGGG Stacking oligos:                  (SEQ ID NO: 60)
5' TCACCGACTGCCCATAGAGAGG
```

Let-7 miRNAs, Let-7b specific DNA probe A, B and stacking oligos were all in concentration of 10 pmol/μl. The annealing reactions contained 1.6 μl (16 pmol) of either Le-7a, 7b, 7c, 7d, 7e, 7f, 7g or 7i which was mixed with 0.5 μl (5 pmol) of Let-7b specific DNA probe A, 2 μl (20 pmol) of probe B, 1 μl of stacking oligos (10 pmol), 1 μl of T4 DNA ligase buffer and 3.9 μl of H$_2$O in a total volume of 10 μl. Four negative controls were included: 1: no miRNA, 2: no stacking oligos, 3: no probe A, 4: no probe B. All the 8 experimental and 4 negative controls were incubated for annealing as described before.

The 10 μl annealing reactions were divided in half and 5 μl were used for ligation incubation at 16° C. and 5 μl for 20° C. incubation. 5 μl of annealing were mixed with 1 μl of T4 DNA ligase buffer, 1 μl (10 pmol/μl) of PBCV-1 DNA ligase and 3 μl of H$_2$O in a 10 μl volume. The ligation reactions were stopped by adding 10 μl of stop buffer then mixed with 15 μl RNA denaturing loading dye. 18 μl of the mix was loaded onto a 15% TBE-urea gel for electrophoresis. The gel was analyzed by Typhoon 9400. The gel with the results of the ligation is shown in FIG. 18B.

Example 13

Comparison of Splint Ligase and TagMan Methods

Figure 19A:
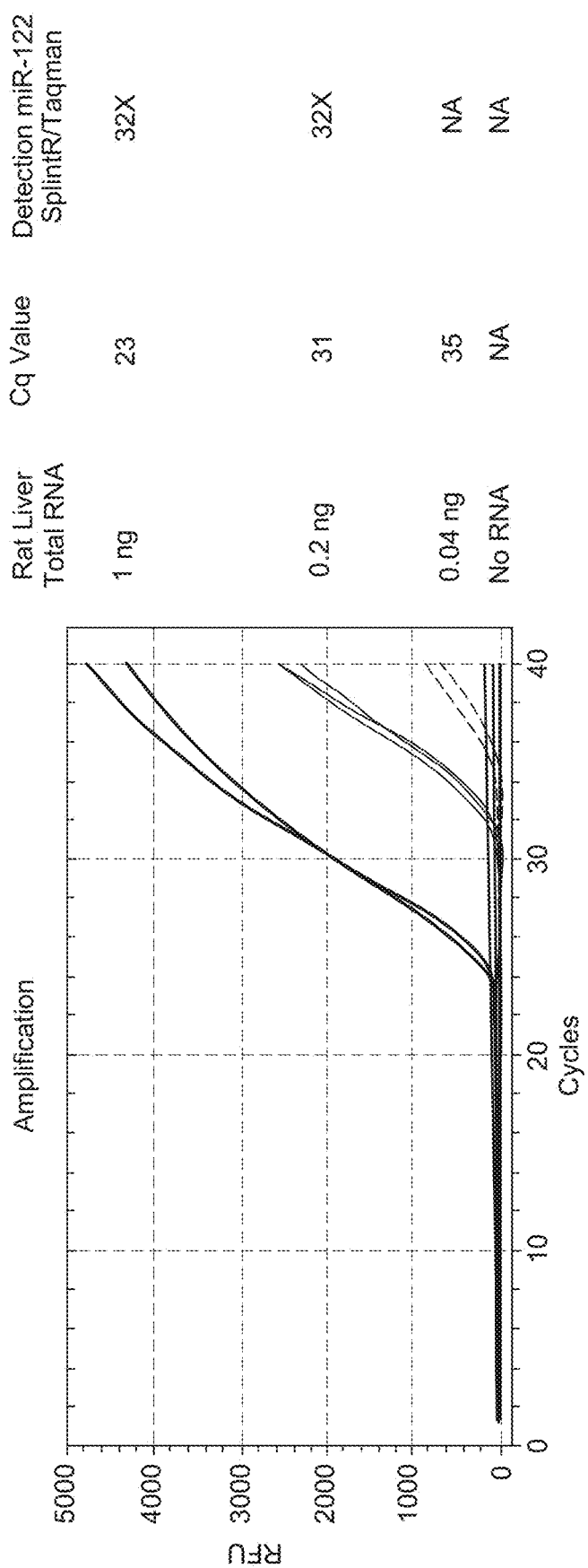
FIGS. 19A and 19B show a comparison of SplintR ligation method to TaqMan method for detection of miR-122 in rat liver RNA. Three different concentrations of rat liver total RNA were used in the qPCR assay; 1 ng, 0.2 ng, 0.04 ng/μL and no rat liver RNA. (A) This panel shows the qPCR traces for the SplintR method described in FIG. 13A. (B) TaqMan detection of miR-122 used DNA hairpin cDNA synthesis followed by detection with a TaqMan probe specific for miR-122 as described in materials and methods. A comparison of the sensitivity of the two methods is shown at the right side of the figure. NA stands for not applicable. This annotation is used when no qPCR signal was detected.
Figure 19B:
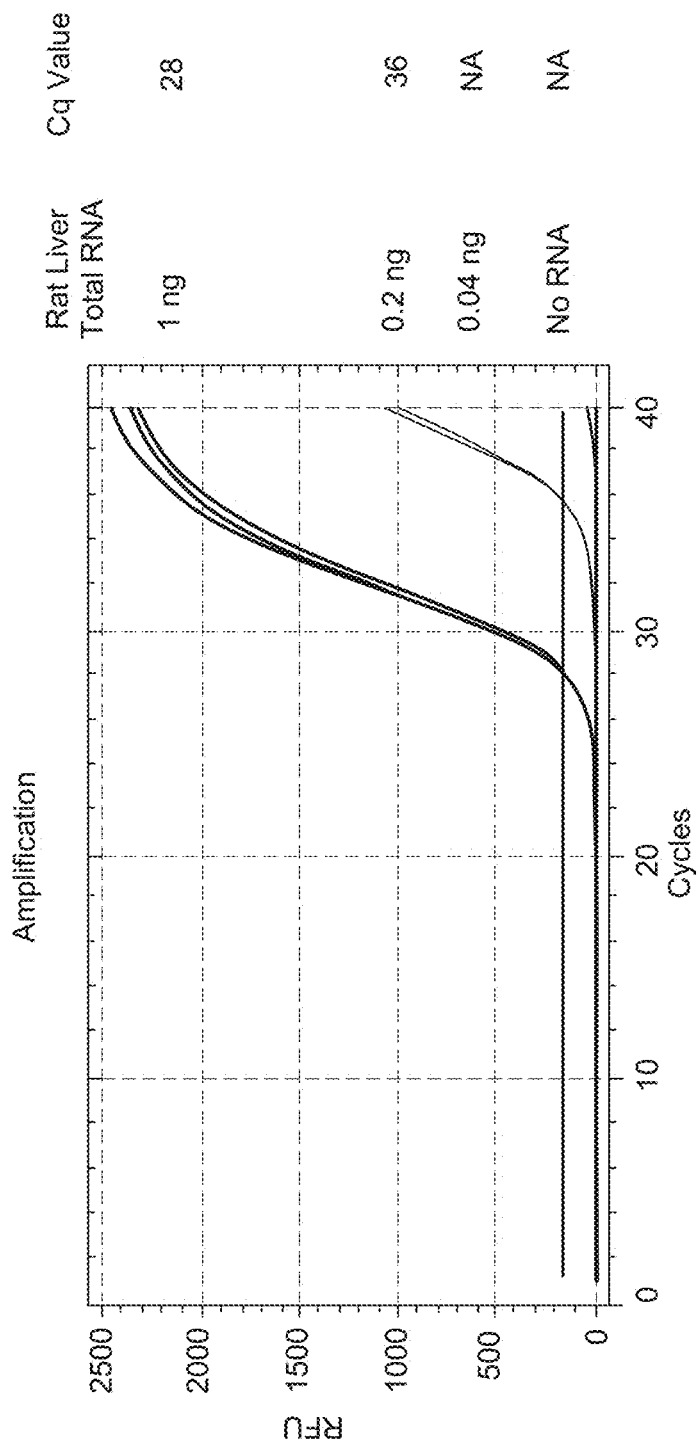

A comparison was made between the splint ligase and TaqMan methods for detection of miR-122 in total rat liver DNA using qPCR. Three different concentrations (1, 0.2 and 0.04 ng) of rat liver total RNA were used. The splint ligase method used miR-122 specific ZEN™ quenched DNA probe that is described in example 10. The TaqMan® assay was performed with the miR-122 specific TaqMan® MicroRNA Reverse Transcription Kit and the TaqMan® Universal PCR Master Mix. At all three RNA concentrations the splint ligase method was more sensitive. For the 1 ng and 0.2 ng amounts the splint ligase assay was about 30-times more sensitive. At the lowest level, 0.04 ng only the splint ligase method could detect miR-122 (FIGS. 19A and 19B).

Example 14

Temperature and Probe Length Alter Ligation Efficiency

Figure 20A:
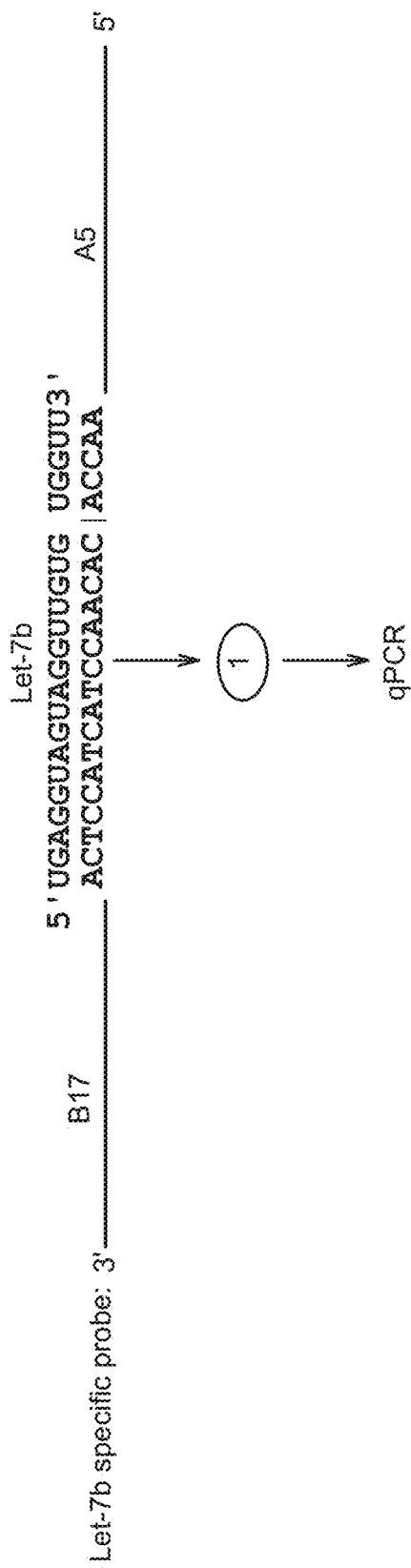
FIGS. 20A and 20B show the temperature dependence of SplintR ligation in detection of let-7b. Probe AS and probe B17 were hybridized to eight different isoforms of let-7 and ligated with SplintR ligase at three different temperatures. (A) The sequence of let-7b and the complementary probes AS and B17 is shown. Three different temperatures, 16° C., 25° C. and 37° C. were used for annealing and ligation (1). (B) The qPCR traces for three different ligation temperatures is shown. The amplified DNA was detected with a double-quenched probe for let-7. The qPCR tracings for the different let-7 isoforms are noted by a single letter at the right of the graph. The correct let-7b tracing is marked with the letter b at the right side of the graph. The tracings of the other let-7 isoforms are also identified by a single letter for each isoform. The reactions for each isoform were done in triplicate.
Figure 20B:
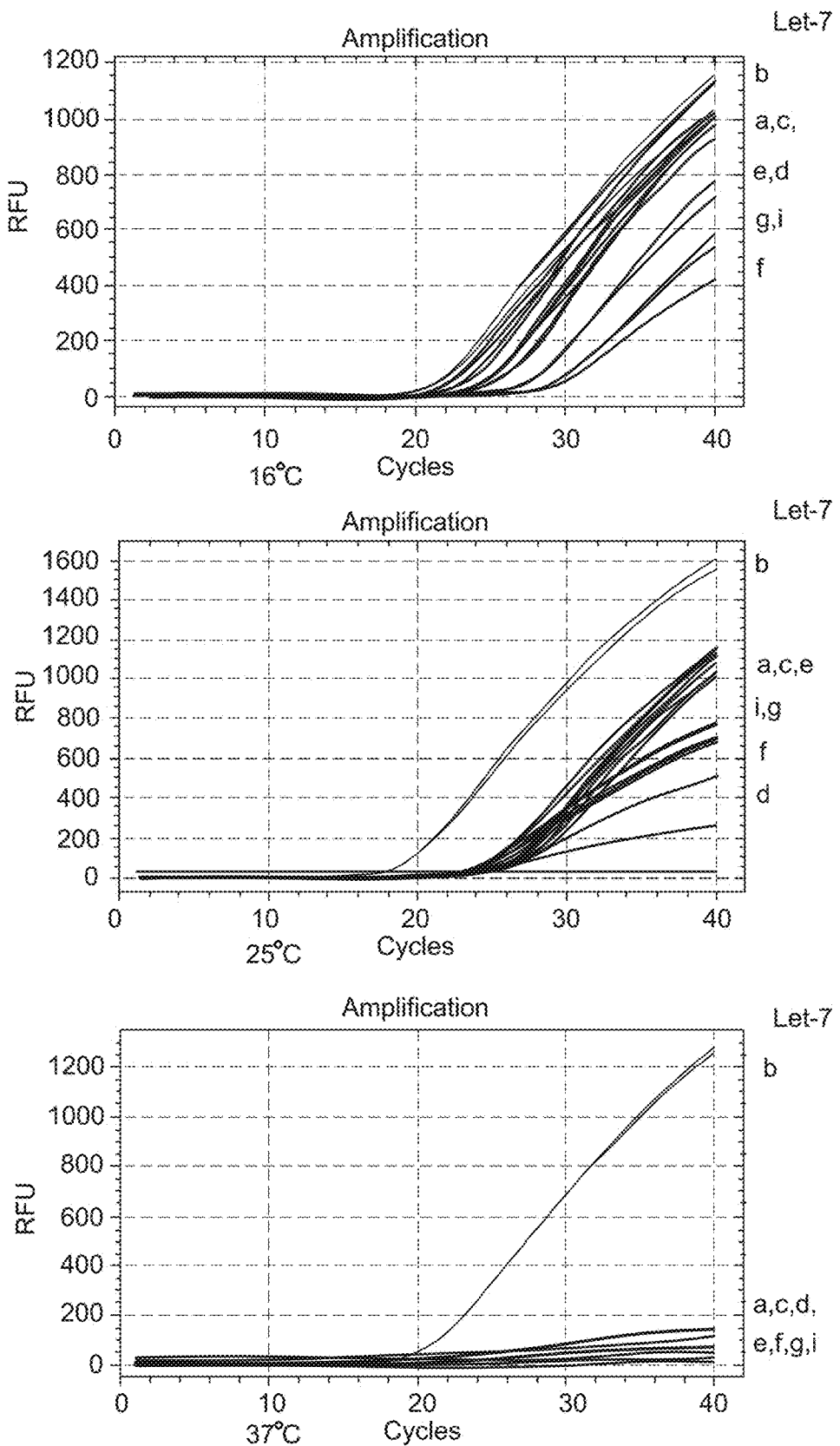

FIGS. 20A and B shows temperature dependence of SplintR ligation in detection of let-7b. Probe A5 and probe B17 were separately hybridized to eight different isoforms of let-7 and ligated with SplintR ligase at three different temperatures. (A) The sequence of let-7b and the complementary probes A5 and B17 is shown. Three different temperatures, 16° C., 25° C. and 37° C. were used for annealing and ligation (1). (B) The qPCR traces for three different ligation temperatures is shown. The amplified DNA was detected with a dual quenched probe that detected all let-7 isoforms. The qPCR tracings for the different let-7 isoforms are noted by a single letter at the right of the graph. The correct let-7b tracing is marked by the letter b. The tracings of the other let-7 isoforms are also marked by a single letter. The reactions for each isoform were done in triplicate.

What is claimed is:

1. A method for detecting a polymorphism in an RNA, comprising:
   (a) hybridizing at least two DNA polynucleotide sequences to a polymorphic sequence in an RNA;
   (b) ligating the at least two DNA polynucleotide sequences to one another using a ligase that has an amino acid sequence that is at least 90% identical to the Chlorella virus PBCV-1 ligase of SEQ ID NO:1, to produce a ligation product, and
   (c) detecting the ligation product of (b), thereby detecting the polymorphic sequence.

2. The method of claim 1, wherein the RNA is of biological origin.

3. The method of claim 1, wherein the RNA is the genome of an RNA virus.

4. The method of claim 1, wherein the RNA is a cellular RNA.

5. The method of claim 4, wherein the cellular RNA is a miRNA, long non-coding RNA, mRNA or tRNA.

6. The method of claim 1, wherein the ligation of step (b) is a done in a buffer comprising 1 μM to 1.5 mM ATP.

7. The method of claim 1, wherein the RNA has a length of at least 10 nucleotides.

8. The method of claim 1, wherein the ligation product of step (b) is circular.

9. The method of claim 1, wherein the ligation product of step (b) is linear.

10. The method of claim 1, wherein the ligase is PBCV-1 ligase.

11. The method of claim 1, wherein the detecting step (c) comprises amplifying the ligation product of step (b).

12. The method of claim 11, wherein the amplifying is done by PCR.

13. The method of claim 11, wherein the amplifying is done by rolling circle amplification.

14. The method of claim 1, wherein the RNA is complementary to at least 8 nucleotides of each of the at least two DNA polynucleotide sequences.

15. The method of claim 1, wherein the detecting is quantitative.

16. The method of claim 1, wherein the ligase that has an amino acid sequence that is at least 95% identical to the Chlorella virus PBCV-1 ligase of SEQ ID NO:1.

* * * * *